US011965019B2

(12) United States Patent
Urosev et al.

(10) Patent No.: US 11,965,019 B2
(45) Date of Patent: Apr. 23, 2024

(54) STABILIZED CHIMERIC FABS

(71) Applicant: ZYMEWORKS BC INC., Vancouver (CA)

(72) Inventors: Dunja Urosev, Vancouver (CA); Yang-Chieh Chou, San Francisco, CA (US)

(73) Assignee: ZYMEWORKS BC INC., Vancouver (CA)

( * ) Notice: Subject to any disclaimer, the term of this patent is extended or adjusted under 35 U.S.C. 154(b) by 65 days.

(21) Appl. No.: 16/624,479

(22) PCT Filed: Jun. 29, 2018

(86) PCT No.: PCT/CA2018/050809
§ 371 (c)(1),
(2) Date: Dec. 19, 2019

(87) PCT Pub. No.: WO2019/000105
PCT Pub. Date: Jan. 3, 2019

(65) Prior Publication Data
US 2020/0308270 A1  Oct. 1, 2020

Related U.S. Application Data

(60) Provisional application No. 62/527,561, filed on Jun. 30, 2017.

(51) Int. Cl.
*C07K 16/24* (2006.01)
*C07K 16/32* (2006.01)

(52) U.S. Cl.
CPC ............ *C07K 16/244* (2013.01); *C07K 16/32* (2013.01); *C07K 2317/24* (2013.01); *C07K 2317/31* (2013.01); *C07K 2317/55* (2013.01); *C07K 2317/92* (2013.01); *C07K 2317/94* (2013.01)

(58) Field of Classification Search
CPC ............ C07K 2317/56; C07K 2317/64; C07K 2317/90
USPC ...................................................... 424/133.1
See application file for complete search history.

(56) References Cited

U.S. PATENT DOCUMENTS

| | | | |
|---|---|---|---|
| 5,208,020 A | 5/1993 | Chari et al. | |
| 5,322,798 A | 6/1994 | Sadowski | |
| 5,341,215 A | 8/1994 | Seher | |
| 5,571,894 A | 11/1996 | Wels et al. | |
| 5,587,458 A | 12/1996 | King et al. | |
| 5,821,333 A | 12/1998 | Carter et al. | |
| 6,037,525 A | 3/2000 | Thompson et al. | |
| 6,177,612 B1 | 1/2001 | Jordan et al. | |
| 6,239,328 B1 | 5/2001 | Thompson | |
| 6,268,125 B1 | 7/2001 | Perkins | |
| 6,289,286 B1 | 9/2001 | Andersson et al. | |
| 6,373,577 B1 | 4/2002 | Braeuer et al. | |
| 6,388,066 B1 | 5/2002 | Bruce et al. | |
| 7,129,062 B2 | 10/2006 | Mermod et al. | |
| 7,259,010 B2 | 8/2007 | Kim et al. | |
| 7,326,567 B2 | 2/2008 | Saha | |
| 7,422,874 B2 | 9/2008 | Kim et al. | |
| 7,947,271 B2 | 5/2011 | Browning et al. | |
| 8,163,888 B2 | 4/2012 | Steeves et al. | |
| 8,329,873 B2 | 12/2012 | Adams et al. | |
| 8,624,003 B2 | 1/2014 | Kellogg et al. | |
| 11,149,094 B2* | 10/2021 | Chiu | C07K 16/468 |
| 11,161,915 B2* | 11/2021 | Urosev | C07K 16/32 |
| 2008/0138860 A1 | 6/2008 | Torikai et al. | |
| 2010/0196265 A1 | 8/2010 | Adams et al. | |
| 2010/0298542 A1 | 11/2010 | Igawa et al. | |
| 2010/0322935 A1 | 12/2010 | Croasdale et al. | |
| 2011/0293613 A1 | 12/2011 | Brinkmann et al. | |
| 2012/0149876 A1 | 1/2012 | Von Kreudenstein et al. | |
| 2012/0316324 A1 | 12/2012 | Adams et al. | |
| 2013/0108622 A1 | 5/2013 | Humphreys | |
| 2013/0243793 A1 | 9/2013 | Lee et al. | |
| 2014/0079691 A1* | 3/2014 | Mcconnell | C07K 16/10 424/133.1 |

(Continued)

FOREIGN PATENT DOCUMENTS

| | | |
|---|---|---|
| CA | 2596925 | 8/2006 |
| WO | 9316185 | 8/1993 |

(Continued)

OTHER PUBLICATIONS

Jordan et al., Proteins, 77: 832-41 (2009).*
IMGT Database "Alignment of alleles: Human IGKC*01" pp. 1-3 (Oct. 16, 20230).*
Extended European Search Report received in the corresponding European Patent Application No. 18823617.8, dated Feb. 24, 2021.
Raheleh Toughiri et al.: 'Comparing domain interactions within antibody Fabs with kappa and lambda light chains', MABS, vol. 8, No. 7, Jul. 25, 2016 (Jul. 25, 2016), pp. 1276-1285.
Natalia Ponomarenko, et al., 'Role of &kgr ;→[lambda] light-chain constant-domain switch in the structure and functionality of A17 reactibody', Acta Crystallographica / D. Section D, Biological Crystallography, vol. 341, No. 3, Mar. 1, 2014 (Mar. 1, 2014) , pp. 807-719.

(Continued)

*Primary Examiner* — Lynn A Bristol
(74) *Attorney, Agent, or Firm* — Kilpatrick Townsend & Stockton LLP

(57) ABSTRACT

Provided herein are stabilized chimeric Fabs derived from a parent chimeric Fab having a lambda light chain. The stabilized chimeric Fabs comprise an immunoglobulin heavy chain polypeptide construct from the parent chimeric Fab, having a CH1 sequence and a VH sequence, as well as a Vlambda-Ckappa chimeric light chain construct. The Vlambda sequence of the chimeric light chain construct corresponds to that of the parent chimeric Fab, and comprises one or more stabilizing amino acid modifications that increase the thermal stability of the stabilized chimeric Fab compared to the parent chimeric Fab. The stabilized Fabs are useful as therapeutic polypeptides, or can be used to prepare antibody constructs in other formats. The stabilized chimeric Fabs may also be useful generally to increase the stability of antibodies having lambda light chains.

25 Claims, 15 Drawing Sheets

Specification includes a Sequence Listing.

(56) References Cited

U.S. PATENT DOCUMENTS

| | | | |
|---|---|---|---|
| 2014/0179574 | A1 | 6/2014 | Seddon et al. |
| 2014/0200331 | A1 | 7/2014 | Corper et al. |
| 2014/0348839 | A1 | 11/2014 | Chowdhury et al. |
| 2015/0086538 | A1 | 3/2015 | Beckmann |

FOREIGN PATENT DOCUMENTS

| | | |
|---|---|---|
| WO | 9733899 | 9/1997 |
| WO | 9734911 | 9/1997 |
| WO | 9923105 | 5/1999 |
| WO | 2006083971 | 8/2006 |
| WO | 2006085518 | 8/2006 |
| WO | 2007109254 | 9/2007 |
| WO | 2010062896 | 6/2010 |
| WO | 2011061119 | 5/2011 |
| WO | 2011117648 | 9/2011 |
| WO | 2011120134 | 10/2011 |
| WO | 2011120135 | 10/2011 |
| WO | 2012031632 | 3/2012 |
| WO | 2012058768 | 5/2012 |
| WO | 2012116453 | 9/2012 |
| WO | 2012163519 | 12/2012 |
| WO | 2013063702 | 5/2013 |
| WO | 2013152860 | 10/2013 |
| WO | 2014012082 | 1/2014 |
| WO | 2014018572 | 1/2014 |
| WO | 2014082179 | 6/2014 |
| WO | 2014150973 | 9/2014 |
| WO | 2014179547 | 11/2014 |
| WO | 2015052230 | 4/2015 |
| WO | 2015181805 | 12/2015 |
| WO | 2017059551 | 4/2017 |

OTHER PUBLICATIONS

Kaneko Mika K. et al., 'Chimeri Anti-Human Podoplanin Antibody NZ-12 of Lambda Light Chain Exerts Higher Antibody-Dependent Cellular Cytotoxicity and Complement-Dependent Cytotoxicity Compared with NZ-8 of Kappa Light Chain', Monoclonal Antibodies in Immunodiagnosis and Immunotherapy, vol. 36, No. 1, Feb. 1, 2017 (Feb. 1, 2017), pp. 25-29.
Thomas Tiller et al., 'A fully synthetic 1-16 human Fab antibody library based on fixed VH/VL framework pairings with favorable biophysical properties', MABS, vol. 5, No. 3, May 1, 2013 (May 1, 2013), pp. 445-470.
International Search Report received in the corresponding PCT Application No. PCT/CA2018/050809, dated Sep. 17, 2018.
Lehmann, et al., Stability engineering of anti-EGFR scFv antibodies by rational design of a lambda-to-kapp swap of the $V^L$ framework wusing a structure-guided approach, mAbs 7:6, 2015, pp. 1058-1071.
Singer M., Berg P., Genes and genomes, in two volumes, vol. 1, Translated from English, Moscow, Mir, 1998, 373 pages, illustrated; see pp. 63-64.
Filippovich, et al., "Biochemical Foundations of Human Life", Textbook for universities. M.: Vlados, 2005, pp. 49-50, 70.
Pakula, et al., "Genetic Analysis of Protein Stability and Function", Annual Reviews of Genetics, vol. 23, No. 1, Dec. 1989, pp. 289-310.
Yarilin, "Fundamentals of Immunology", Textbooks for Medical Students, M.: Medicine, 1999, pp. 172-174.
Nomenclature and Symbolism for Amino, Acids and Peptides, European Journal of Biochemistry, vol. 138, Jan. 1984, pp. 9-37.
Abdiche et al., Determining Kinetics and Affinities of Protein Interactions Using a Parallel Real-time Label-free Biosensor, the Octet, Analytical Biochemistry, vol. 377, No. 2, Jun. 15, 2008, pp. 209-217.
Aldrich et al., EASE Vectors for Rapid Stable Expression of Recombinant Antibodies, Biotechnology Progress, vol. 19, Sep.-Oct. 2003, pp. 1433-1438.

Al-Lazikani et al., Standard Conformations for the Canonical Structures of Immunoglobulins, Journal of Molecular Biology, vol. 273, No. 4, Nov. 7, 1997, pp. 927-948.
Altschul et al., Basic Local Alignment Search Tool, Journal of Molecular Biology, vol. 215, No. 3, Oct. 5, 1990, pp. 403-410.
Altschul et al., Gapped BLAST and PSI-BLAST: A New Generation of Protein Database Search Programs, Nucleic Acids Research, vol. 25, No. 17, Sep. 1, 1997, pp. 3389-3402.
Carlson et al., Cell-free Protein Synthesis: Applications Come of Age, Biotechnology Advances, vol. 30, No. 5, Sep.-Oct. 2012, pp. 1185-1194.
Chen et al., Improving the Ch1-CK Heterodimerization and Pharmacokinetics of 4Dm2m, A Novel Potent CD4-antibody Fusion Protein Against HIV-1, mAbs, vol. 8, No. 4, May-Jun. 2016, pp. 761-774.
Chen et al., Influence of Histidine on the Stability and Physical Properties of a Fully Human Antibody in Aqueous and Solid Forms, Pharmaceutical Research, vol. 20, No. 12, Dec. 2003, pp. 1952-1960.
Chennamsetty et al., Design of Therapeutic Proteins with Enhanced Stability, Proceedings of the National Academy of Sciences of the United States of America, vol. 106, No. 29, Jul. 21, 2009, pp. 11937-11942.
Chothia, The Nature of the Accessible and Buried Surfaces in Proteins, Journal of Molecular Biology, vol. 105, No. 1, Jul. 25, 1976, pp. 1-12.
Chu et al., Inhibition of B Cell Receptor-Mediated Activation of Primary Human B Cells by Coengagement of CD19 and FcgammaRIIb With Fc-engineered Antibodies, Molecular Immunology, vol. 45, No. 15, Sep. 2008, pp. 3926-3933.
Colberre-Garapin et al., A New Dominant Hybrid Selective Marker for Higher Eukaryotic Cells, Journal of Molecular Biology, vol. 105, No. 1, Jul. 25, 1981, pp. 1-14.
Debler et al., Structural Origins of Efficient Proton Abstraction from Carbon by a Catalytic Antibody, Proceedings of the National Academy of Sciences of the United States of America, vol. 102, No. 14, Apr. 5, 2005, pp. 4984-4989.
Demarest et al., Engineering Stability Into *Escherichia coli* Secreted Fabs Leads to Increased Functional Expression, Protein Engineering, Design & Selection, vol. 19, No. 7, Jul. 2006, pp. 325-336.
Denardo et al., Comparison of 1,4,7, 10-tetraazacyclododecane-N,N',N'',N'''-tetraacetic Acid (DOTA)-Peptide-ChL6, A Novel Immunoconjugate with Catabolizable linker, to 2-iminothiolane-2-[p-(bromoacetamido) benzyl]-DOTA-ChL6 in Breast Cancer Xenografts, Clinical Cancer Research, vol. 4, No. 10, Oct. 1998, pp. 2483-2490.
Dong et al., Some New Aspects in Biosensors, Journal of Biotechnology, vol. 82, No. 4, Feb. 2002, pp. 303-323.
Durocher et al., High-level and High-Throughput Recombinant Protein Production by Transient Transfection of Suspension-Growing Human 293-EBNA1 Cells, Nucleic Acids Research, vol. 30, No. 2, Jan. 15, 2002, pp. 1-9.
Edelman et al., The Covalent Structure of an Entire gamma Gimmunoglobulin Molecule, Proceedings of the National Academy of Sciences of the United States of America, vol. 63, No. 1, May 1969, pp. 78-85.
Faelber et al., The 1.85 Å Resolution Crystal Structures of Tissue factor in Complex with Humanized Fab d3h44 and of free humanized Fab d3h44: revisiting the Solvation of Antigen Combining Sites, Journal of Molecular Biology, vol. 313, Issue 1, Oct. 12, 2001, pp. 83-97.
Fenn et al., Crystal Structure of an Anti-Ang2 CrossFab Demonstrates Complete Structural and Functional Integrity of the Variable Domain, PLOS One, vol. 8, No. 4, Apr. 17, 2013, pp. 1-7.
Ferrara et al., Unique Carbohydrate-carbohydrate Interactions are Required for High Affinity Binding Between FcγRIII and Antibodies Lacking Core Fucose, Proceedings of the National Academy of Sciences of the United States of America, vol. 108, No. 31, Aug. 2, 2011, pp. 12669-12674.
Fivash et al., BIAcore for Macromolecular Interaction, Current Opinion in Biotechnology, vol. 9, No. 1, Feb. 1998, pp. 97-101.

(56) References Cited

OTHER PUBLICATIONS

Garber, A Broad Range of Fab stabilities within a Host of Therapeutic IgGs, Biochemical and Biophysical Research Communications, vol. 355, No. 3, Apr. 13, 2007, pp. 751-757.
Ghetie et al., Multiple Roles for the Major Histocompatibility Complex Class I—Related Receptor FcRn, Annual Review of Immunology, vol. 18, 2000, pp. 739-766.
Ghirlando et al., Glycosylation of Human IgG-Fc: Influences on Structure Revealed by Differential Scanning Micro-calorimetry, Immunology Letters, vol. 68, No. 1, May 3, 1999, pp. 47-52.
Glick et al., Molecular Biotechnology: Principles and Applications of Recombinant DNA, ASM Press, Washington, D. C., 2nd edition, 1998.
Gluzman, SV40-transformed Simian Cells Support the Replication of Early SV40 Mutants, Cell, vol. 23, No. 1, Jan. 1981, pp. 175-182.
Gramer et al., Production of Stable Bispecific IgG1 by Controlled Fab-arm Exchange: Scalability from Bench to Large-Scale Manufacturing by Application of Standard Approaches, mAbs, vol. 5, No. 6, Nov.-Dec. 2013, pp. 962-973.
Heider et al., A Novel Fc-Engineered Monoclonal Antibody to CD37 with Enhanced ADCC and High Proapoptotic Activity for Treatment of B-cell Malignancies, Blood, vol. 118, No. 15, Oct. 13, 2011, pp. 4159-4168.
Henikoff et al., Amino Acid Substitution Matrices from Protein Blocks, Proceedings of the National Academy of Sciences of the United States of America, vol. 89, No. 22, Nov. 15, 1992, pp. 10915-10919.
Honegger, Engineering Antibodies for Stability and Efficient Folding, Therapeutic Antibodies. Handbook of Experimental Pharmacology, vol. 181, 2008, pp. 47-68.
Honegger et al., The Influence of the Framework Core Residues on the Biophysical Properties of Immunoglobulin Heavy Chain Variable Domains, Protein Engineering, Design and Selection, vol. 22, No. 3, Mar. 2009, pp. 121-134.
Honegger et al., Yet Another Numbering Scheme for Immunoglobulin Variable Domains: An Automatic Modeling and Analysis Tool, Journal of Molecular Biology, vol. 309, No. 3, Jun. 8, 2001, pp. 657-670.
Ionescu et al., Contribution of Variable Domains to the Stability of Humanized IgG1 Monoclonal Antibodies, Journal of Pharmaceutical Sciences, vol. 97, No. 4, Apr. 2008, pp. 1414-1426.
Jones et al., Replacing the Complementarity-Determining Regions in a Human Antibody with Those from a Mouse, Nature. vol. 321, No. 6069, May 29-Jun. 4, 1986, pp. 522-525.
Krey et al., Structural Basis of HCV Neutralization by Human Monoclonal Antibodies Resistant to Viral Neutralization Escape, PLOS Pathog, vol. 9, No. 5, May 2013, pp. 1-10.
Kabat et al., Identical V Region Amino Acid Sequences and Segments of Sequences in Antibodies of Different Specificities. Relative Contributions of VH And VL Genes, Minigenes, and Complementarity-determining Regions to Binding of Antibody-combining Sites, Journal of Immunology, vol. 147, No. 5, Sep. 1, 1991, pp. 1709-1719.
Klein et al., Progress in Overcoming the Chain Association Issue in Bispecific Heterodimeric IgG Antibodies, mAbs, vol. 4, No. 6, Nov. 1, 2012, pp. 653-663.
Luckow et al., Trends in the Development of Baculovirus Expression Vectors, Bio/Technology, vol. 6, 1988, pp. 47-55.
Lazar et al., Engineered antibody Fc variants with enhanced effector function, Proceedings of the National Academy of Sciences, vol. 103, No. 11, Mar. 14, 2006, pp. 4005-4010.
Lefranc et al., IMGT, the International ImMunoGeneTics Information System, Cold Spring Harbor Protocols, vol. 2011, No. 6, Jun. 1, 2011, pp. 595-603.
Lefranc et al., IMGT®, The International ImMunoGeneTics Information System®, Nucleic Acids Research, vol. 37, Jan. 2009, pp. D1006-D1012.
Lewis et al., Generation of Bispecific IgG Antibodies by Structure-Based Design of an Orthogonal Fab Interface, Nature Biotechnology, vol. 32, No. 2, Feb. 2014, pp. 191-198.
Lowy et al., Isolation of Transforming DNA: Cloning the Hamster Aprt Gene, Cell, vol. 22, No. 3, Dec. 1980, pp. 817-823.
Lu et al., MicroRNA-21 Limits In Vivo Immune Response-Mediated Activation of the IL-12/IFN-γ Pathway, Th1 Polarization, and the Severity of Delayed-Type Hypersensitivity, Journal of Immunology, vol. 187, No. 6, Sep. 15, 2011, pp. 3362-3373.
Miller et al., Stability Engineering of scFvs for the Development of Bispecific and Multivalent Antibodies, Protein Engineering, Design and Selection, vol. 23, No. 7, Jul. 2010, pp. 549-557.
Mcconnell et al., A General Approach to Antibody Thermostabilization, mAbs, vol. 6, No. 5, Sep.-Oct. 2014, pp. 1274-1282.
Mcmahan et al., A Novel IL-1 Receptor, Cloned from B Cells by Mammalian Expression, is Expressed in Many Cell Types, The EMBO Journal, vol. 10, No. 10, Oct. 1991, pp. 2821-2832.
Mizushima et al., Structural Basis for Improved Efficacy of Therapeutic Antibodies on Defucosylation of Their Fc Glycans, Genes Cells, vol. 16, No. 11, Nov. 2011, pp. 1071-1080.
Monsellier et al., Improving the Stability of an Antibody Variable Fragment by a Combination of Knowledge-based Approaches: Validation and Mechanisms, Journal of Molecular Biology, vol. 362, No. 3, Sep. 22, 2006, pp. 580-593.
Moore et al., Engineered Fc Variant Antibodies with Enhanced Ability to Recruit Complement and Mediate Effector Functions, mAbs, Landes Biosciences, vol. 2, No. 2, Mar.-Apr. 2010, pp. 181-189.
Mullett et al., Surface Plasmon Resonance-Based Immunoassays, Methods, vol. 22, No. 1, Sep. 2000, pp. 77-91.
Mulligan et al., Selection for Animal Cells that Express the *Escherichia coli* Gene Coding for Xanthine-guanine Phosphoribosyltransferase, Proceedings of the National Academy of Sciences of the United States of America, vol. 78, No. 4, Apr. 1981, pp. 2072-2076.
Murray et al., Epitope Affinity Chromatography and Biophysical Studies of Monoclonal Antibodies and Recombinant Antibody Fragments, Journal of Chromatographic Science, vol. 40, No. 6, Aug. 2002, pp. 343-349.
Niesen et al., The Use of Differential Scanning Fluorimetry to Detect Ligand Interactions That Promote Protein Stability, Nature Protocols, vol. 2, No. 9, Feb. 2007, pp. 2212-2221.
Nordstrom et al., Anti-tumor Activity and Toxicokinetics Analysis of MGAH22, an anti-HER2 Monoclonal Antibody with Enhanced Fcγ Receptor Binding Properties, Breast Cancer Research, vol. 13, No. 6, 2011, pp. 1-14.
O'Hare et al., Transformation of Mouse Fibroblasts to Methotrexate Resistance by a Recombinant Plasmid Expressing a Prokaryotic Dihydrofolate Reductase, Proceedings of the National Academy of Sciences of the United States of America, vol. 78, No. 3, Mar. 1, 1981, pp. 1527-1531.
International Patent Application No. PCT/CA2018/050809, IPRP dated Jan. 9, 2020.
Pepinsky et al., Improving the Solubility of Anti-LINGO-1 Monoclonal Antibody Li33 by Isotype Switching and Targeted Mutagenesis, Protein Science, vol. 19, No. 5, May 2010, pp. 954-966.
Peterson et al., Enzymatic Cleavage of Peptide-Linked Radiolabels from Immunoconjugates, Bioconjugate Chemistry, vol. 10, No. 4, 1999, pp. 553-557.
Pokkuluri et al., Increasing Protein Stability by Polar Surface Residues: Domain-Wide Consequences of Interactions Within a Loop, Biophysical Journal, vol. 82, No. 1, Jan. 2002, pp. 391-398.
Presta, Antibody Engineering, Current Opinion in Structural Biology, vol. 2, 1992, pp. 593-596.
Raghavan et al., Fc Receptors and Their Interactions with Immunoglobulins, Annual Review of Cell and Developmental Biology, vol. 12, Nov. 1996, pp. 181-220.
Rasmussen et al., Isolation, Characterization and Recombinant Protein Expression in Veggie-Cho: A Sérum-free Cho Host Cell Line, Cytotechnology, vol. 28, Nov. 1998, pp. 31-42.
Rich et al., Advances in Surface Plasmon Resonance Biosensor Analysis, Current Opinion in Biotechnology, vol. 11, No. 1, Feb. 1, 2000, pp. 54-61.
Riechmann et al., Reshaping Human Antibodies for Therapy, Nature, vol. 332, No. 6162, Mar. 1988, pp. 323-327.
Rosenberg et al., The Pharmacology of Monoclonal Antibodies, Edition—Springer-Verlag, vol. 113, 1994, pp. 269-315.

(56) References Cited

OTHER PUBLICATIONS

Rouet et al., Stability Engineering of the Human Antibody Repertoire, FEBS Letters, vol. 588, No. 2, Jan. 21, 2014, pp. 269-277.
Santerre et al., Expression of Prokaryotic Genes for Hygromycin B and G418 Resistance as Dominant-Selection Markers in Mouse L Cells, Gene, vol. 30, No. 1-3, Oct. 1984, pp. 147-156.
Schneider et al., A Reverse Binding Motif That Contributes to Specific Protease Inhibition by Antibodies, Journal of Molecular Biology, vol. 415, No. 4, Jan. 27, 2012, pp. 699-715.
Shields et al., High Resolution Mapping of the Binding Site on Human IgG1 for FcγRI, FcγRII, FcγRIII, and FcRn and Design of IgG1 Variants with Improved Binding to the FcγR, Journal of Biological Chemistry, vol. 276, No. 9, Mar. 2, 2001, pp. 6591-6604.
Smirnova et al., Reactibodies Generated by Kinetic Selection Couple Chemical Reactivity with Favorable Protein Dynamics, Proceedings of the National Academy of Sciences of the United States of America, vol. 108, No. 38, Sep. 6, 2011, pp. 15954-15959.
Stavenhagen et al., Fc Optimization of Therapeutic Antibodies Enhances their Ability to Kill Tumor Cells in Vitro and Controls Tumor expansion in Vivo via Low-Affinity Activating Fcγ Receptors, Cancer Research, vol. 67, No. 18, Sep. 15, 2007, pp. 8882-8890.
Steinwand et al., The Influence of Antibody Fragment Format on Phage Display based Affinity Maturation of IgG, MAbs, vol. 6, No. 1, Jan.-Feb. 2014, pp. 204-218.
Stewart et al., A Variant Human IgG1-Fc Mediates Improved ADCC, Protein Engineering Design & Selection, vol. 24, No. 9, Sep. 2011, pp. 671-678.
Strop et al., Generating Bispecific Human IgG1 and IgG2 Antibodies from any Antibody Pair, Journal of Molecular Biology, vol. 420, No. 3, Jul. 13, 2012, pp. 204-219.
Summers et al., A Manual of Methods for Baculovirus Vectors and Insect Cell Culture Procedures, Texas Agricultural Experiment Station, Apr. 30, 1987.
Szybalska et al., Genetics of Human Cell Line. IV. DNA-mediated Heritable Transformation of a Biochemical Trait, Proceedings of the National Academy of Sciences of the United States of America, vol. 48, No. 12, Dec. 15, 1962, pp. 2026-2034.
Takahashi et al., Expression of MUC1 on Myeloma Cells and Induction of HLA-Unrestricted CTL Against MUC1 from a Multiple Myeloma Patient, Journal of Immunology, vol. 153, No. 5, Sep. 1, 1994, pp. 2102-21209.
Wigler et al., Transfer of Purified Herpes Virus Thymidine Kinase Gene to Cultured Mouse Cells, Cell, vol. 11, No. 1, May 1977, pp. 223-232.
Wigler et al., Transformation of Mammalian Cells with an Amplifiable Dominant-acting Gene, Proceedings of the National Academy of Sciences of the United States of America, vol. 77, No. 6, Jun. 1980, pp. 3567-3570.
Wu et al., Structure-based Engineering of a Monoclonal Antibody for Improved Solubility, Protein Engineering Design & Selection, vol. 23, No. 8, Aug. 2010, pp. 643-651.
Zamyatnin, Protein Volume in Solution, Progress in Biophysics and Molecular Biology, vol. 24, 1972, pp. 107-123.
Zimmerman et al., A Triglycine Linker Improves Tumor Uptake and Biodistributions of 67-Cu-Labeled Anti-Neuroblastoma MAb chCE7 F(ab')2 Fragments, Nuclear Medicine and Biology, vol. 26, No. 8, Nov. 1999, pp. 943-950.
Zuberbuhler et al., A General Method for the Selection of High-Level scFv and IgG Antibody Expression by Stably Transfected Mammalian Cells, Protein Engineering, Design and Selection, vol. 22, No. 3, Mar. 2009, pp. 169-174.

* cited by examiner

```
CAT-2200   WT     NFMLTQPHSVSESPGKTVTISCTRSSGSLANYYVQWYQQRPGSSPTIVIFANNQRPSGVP
CAT-2200   Vλ-Cκ  NFMLTQPHSVSESPGKTVTISCTRSSGSLANYYVQWYQQRPGSSPTIVIFANNQRPSGVP
                  ************************************************************

CAT-2200   WT     DRFSGSIDSSSNSASLTISGLKTEDEADYYCQTYDPYSVVFGGGTKLTVL GQPKAAPSVT
CAT-2200   Vλ-Cκ  DRFSGSIDSSSNSASLTISGLKTEDEADYYCQTYDPYSVVFGGGTKLTVL RTVAAPSVF
                  **************************************************  *  ****

CAT-2200   WT     LFPPSSEELQANKATLVCLISDFYPGAVTVAWKADSSPVKAG-VETTTPSKQSNNKYAAS
CAT-2200   Vλ-Cκ  IFPPSDEQLKSGTASVVCLLNNFYPREAKVQWKVDNALQSGNSQESVTEQDSKDSTYSLS
                  :***** *:*.:.*:*** *::*:**.**.**..: *.*. .::*.*::.*::.*::*

CAT-2200   WT     SYLSLTPEQWKSHRSYSCQVTHEG--STVEKTVAPTECS  (SEQ ID NO:8)
CAT-2200   Vλ-Cκ  STLTLSKADYEKHKVYACEVTHQGLSSPVTKSFNRGEC-  (SEQ ID NO:9)
                  * *:*:  : :.::* *:.***:*  * *.*.  .*
```

Variable domain-CAT-2200 (dashed box)
Constant domain (solid box)

SEQUENCE LISTING

<160> NUMBER OF SEQ ID NOS: 32

<210> SEQ ID NO 1
<211> LENGTH: 226
<212> TYPE: PRT
<213> ORGANISM: Artificial Sequence
<220> FEATURE:
<223> OTHER INFORMATION: H3 heavy chain Fab

<400> SEQUENCE: 1

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr
225

<210> SEQ ID NO 2
<211> LENGTH: 217
<212> TYPE: PRT
<213> ORGANISM: Artificial Sequence
<220> FEATURE:
<223> OTHER INFORMATION: H3 light chain (lambda)

<400> SEQUENCE: 2

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
            35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 3
<211> LENGTH: 218
<212> TYPE: PRT
<213> ORGANISM: Artificial Sequence
<220> FEATURE:
<223> OTHER INFORMATION: H3 V(lambda)-C(kappa) chimeric light chain

<400> SEQUENCE: 3

Gln Ser Ala Leu Thr Gln Pro Ala Ser Val Ser Gly Ser Pro Gly Gln
1               5                   10                  15

-continued

Ser Ile Thr Ile Ser Cys Thr Gly Thr Ser Ser Asp Val Gly Gly Tyr
                20                  25                  30

Asn Phe Val Ser Trp Tyr Gln Gln His Pro Gly Lys Ala Pro Lys Leu
            35                  40                  45

Met Ile Tyr Asp Val Ser Asp Arg Pro Ser Gly Val Ser Asp Arg Phe
 50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Thr Lys Val Thr Val Leu Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 240
<212> TYPE: PRT
<213> ORGANISM: Artificial Sequence
<220> FEATURE:
<223> OTHER INFORMATION: EP6b_B01 heavy chain Fab

<400> SEQUENCE: 4

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ala Asn
                20                  25                  30

Ser Tyr Tyr Gly Val Trp Val Arg Gln Ser Pro Gly Lys Gly Leu Glu
            35                  40                  45

Trp Val Gly Ser Ile Ala Tyr Arg Gly Asn Ser Asn Ser Gly Ser Thr
 50                  55                  60

Tyr Tyr Asn Pro Ser Leu Lys Ser Arg Ala Thr Val Ser Val Asp Ser
65                  70                  75                  80

Ser Lys Asn Gln Val Ser Leu Arg Leu Thr Ser Val Thr Ala Ala Asp
                85                  90                  95

Thr Ala Leu Tyr Tyr Cys Ala Arg Arg Gln Leu Leu Asp Asp Gly Thr
            100                 105                 110

Gly Tyr Gln Trp Ala Ala Phe Asp Val Trp Gly Gln Gly Thr Met Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

```
Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240
```

```
<210> SEQ ID NO 5
<211> LENGTH: 216
<212> TYPE: PRT
<213> ORGANISM: Artificial Sequence
<220> FEATURE:
<223> OTHER INFORMATION: EP6b_B01 light chain (lambda)

<400> SEQUENCE: 5
```

```
Gln Ser Val Leu Thr Gln Pro Pro Ser Val Ser Glu Ala Pro Arg Gln
1               5                   10                  15

Thr Val Thr Ile Ser Cys Ser Gly Asn Ser Ser Asn Ile Gly Arg Tyr
            20                  25                  30

Pro Val Asn Trp Tyr Gln Gln Leu Pro Gly Lys Ala Pro Lys Leu Leu
            35                  40                  45

Ile Tyr Ser Asp Asn Leu Arg Phe Ser Gly Val Pro Asp Arg Phe Ser
    50                  55                  60

Gly Ser Lys Ser Gly Thr Thr Ala Ser Leu Ala Ile Arg Asp Leu Leu
65                  70                  75                  80

Ser Glu Asp Glu Ala Asp Tyr Tyr Cys Ser Thr Trp Asp Asp Thr Leu
                85                  90                  95

Glu Gly Trp Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215
```

```
<210> SEQ ID NO 6
<211> LENGTH: 217
<212> TYPE: PRT
<213> ORGANISM: Artificial Sequence
<220> FEATURE:
<223> OTHER INFORMATION: EP6b_B01 V(lambda)-C(kappa) chimeric light
      chain

<400> SEQUENCE: 6
```

Gln Ser Val Leu Thr Gln Pro Pro Ser Val Ser Glu Ala Pro Arg Gln
1               5                   10                  15

Thr Val Thr Ile Ser Cys Ser Gly Asn Ser Ser Asn Ile Gly Arg Tyr
            20                  25                  30

Pro Val Asn Trp Tyr Gln Gln Leu Pro Gly Lys Ala Pro Lys Leu Leu
        35                  40                  45

Ile Tyr Ser Asp Asn Leu Arg Phe Ser Gly Val Pro Asp Arg Phe Ser
    50                  55                  60

Gly Ser Lys Ser Gly Thr Thr Ala Ser Leu Ala Ile Arg Asp Leu Leu
65                  70                  75                  80

Ser Glu Asp Glu Ala Asp Tyr Tyr Cys Ser Thr Trp Asp Asp Thr Leu
                85                  90                  95

Glu Gly Trp Val Phe Gly Gly Gly Thr Lys Val Thr Val Leu Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 7
<211> LENGTH: 226
<212> TYPE: PRT
<213> ORGANISM: Artificial Sequence
<220> FEATURE:
<223> OTHER INFORMATION: CAT-2200 heavy chain Fab

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

```
Cys Leu Val Lys Asp Tyr Phe Pro Gln Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr
225
```

<210> SEQ ID NO 8
<211> LENGTH: 216
<212> TYPE: PRT
<213> ORGANISM: Artificial Sequence
<220> FEATURE:
<223> OTHER INFORMATION: CAT-2200 light chain (lambda)

<400> SEQUENCE: 8

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ser Pro Thr Ile Val
            35                  40                  45

Ile Phe Ala Asn Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
            85                  90                  95

Tyr Ser Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215
```

<210> SEQ ID NO 9
<211> LENGTH: 217
<212> TYPE: PRT
<213> ORGANISM: Artificial Sequence
<220> FEATURE:
<223> OTHER INFORMATION: CAT-2200 V(lambda)-C(kappa) chimeric light
      chain

```
<400> SEQUENCE: 9

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 10
<211> LENGTH: 227
<212> TYPE: PRT
<213> ORGANISM: Artificial Sequence
<220> FEATURE:
<223> OTHER INFORMATION: Pertuzumab heavy chain Fab

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Thr Asp Tyr Thr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
                130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr
225

<210> SEQ ID NO 11
<211> LENGTH: 214
<212> TYPE: PRT
<213> ORGANISM: Artificial Sequence
<220> FEATURE:
<223> OTHER INFORMATION: Pertuzumab light chain (kappa)

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 225
<212> TYPE: PRT
<213> ORGANISM: Artificial Sequence
<220> FEATURE:
<223> OTHER INFORMATION: D3H44 heavy chain Fab
```

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ala Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr
225

<210> SEQ ID NO 13
<211> LENGTH: 214
<212> TYPE: PRT
<213> ORGANISM: Artificial Sequence
<220> FEATURE:
<223> OTHER INFORMATION: D3H44 light chain (kappa)

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Lys Ser Tyr
            20                  25                  30

Leu Asn Trp Tyr Gln Gln Lys Pro Gly Lys Ala Pro Lys Val Leu Ile
        35                  40                  45

Tyr Tyr Ala Thr Ser Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 227
<212> TYPE: PRT
<213> ORGANISM: Artificial Sequence
<220> FEATURE:
<223> OTHER INFORMATION: IgG1 Fc

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 681
```

<212> TYPE: DNA
<213> ORGANISM: Artificial Sequence
<220> FEATURE:
<223> OTHER INFORMATION: IgG1 Fc

<400> SEQUENCE: 15

```
gataagaccc acacctgccc tccctgtcca gctccagaac tgctgggagg acctagcgtg    60
ttcctgtttc ccctaagcc aaaagacact ctgatgattt ccaggactcc cgaggtgacc    120
tgcgtggtgg tggacgtgtc tcacgaggac cccgaagtga agttcaactg gtacgtggat    180
ggcgtggaag tgcataatgc taagacaaaa ccaagagagg aacagtacaa ctccacttat    240
cgcgtcgtga gcgtgctgac cgtgctgcac caggactggc tgaacgggaa ggagtataag    300
tgcaaagtca gtaataaggc cctgcctgct ccaatcgaaa aaaccatctc taaggccaaa    360
ggccagccaa gggagcccca ggtgtacaca ctgccaccca gcagagacga actgaccaag    420
aaccaggtgt ccctgacatg tctggtgaaa ggcttctatc ctagtgatat tgctgtggag    480
tgggaatcaa atggacagcc agagaacaat tacaagacca cacctccagt gctggacagc    540
gatggcagct tcttcctgta ttccaagctg acagtggata atctcgatg gcagcagggg    600
aacgtgttta gttgttcagt gatgcatgaa gccctgcaca atcattacac tcagaagagc    660
ctgtccctgt ctcccggcaa a    681
```

<210> SEQ ID NO 16
<211> LENGTH: 678
<212> TYPE: DNA
<213> ORGANISM: Artificial Sequence
<220> FEATURE:
<223> OTHER INFORMATION: H3 heavy chain Fab

<400> SEQUENCE: 16

```
caggtccagc tgcaggaatc tggcggagga ctggtcaaac ctggaggctc tctgagactg    60
tcatgtgctg ctagtggctt tactttcagc tcctactgga tgtcttgggt gcgacaggcc    120
cccggcaagg gactggagtg ggtcgcaaac atcaatagag acggatctgc cagttactat    180
gtggatagcg tcaagggccg gttcaccatt tcaagagacg atgctaaaaa cagcctgtat    240
ctgcagatga acagcctgag ggccgaagac acagctgtgt actattgcgc acgcgatcgc    300
ggcgtgggat atttcgatct gtggggccgc ggaaccctgg tgaccgtctc atctgctagc    360
actaaggggc cttccgtgtt tccactggct ccctctagta atccacctc tggaggcaca    420
gctgcactgg gatgtctggt gaaggattac ttccctgaac cagtcacagt gagttggaac    480
tcaggggctc tgacaagtgg agtccatact tttcccgcag tgctgcagtc aagcggactg    540
tactccctgt cctctgtggt caccgtgcct agttcaagcc tgggcaccca gacatatatc    600
tgcaacgtga atcacaagcc atcaaataca aaagtcgaca gaaaggtgga accaaaaagc    660
tgcgataaaa cccataca    678
```

<210> SEQ ID NO 17
<211> LENGTH: 651
<212> TYPE: DNA
<213> ORGANISM: Artificial Sequence
<220> FEATURE:
<223> OTHER INFORMATION: H3 light chain (lambda)

<400> SEQUENCE: 17

```
cagagcgcac tgactcagcc tgcttccgtg tccggctccc ctgggcagag tattacaatc    60
tcatgcactg gcacctcatc cgacgtgggc gggtacaact ttgtcagctg gtatcagcag    120
```

-continued

| | |
|---|---|
| cacccaggca aggcccccaa actgatgatc tacgacgtgt ccgatcggcc ttccggggtc | 180 |
| tctgacagat tctccggatc taagagtggc aataccgcca gcctgatcat ttccgggctg | 240 |
| caggcagacg atgaggccga ttactattgc agctcctatg gatctagttc aacacatgtg | 300 |
| atcttcggag gcgggaccaa ggtgacagtc ctggggcagc ctaaagcggc ccctctgtg | 360 |
| actctgtttc ccctagctc cgaggaactg caggctaaca aggcaactct ggtgtgtctg | 420 |
| attagcgact ctacccagg agctgtgacc gtcgcctgga aggctgattc tagtcccgtg | 480 |
| aaagcaggcg tcgagaccac aactcctagt aagcagtcaa caacaagta cgcagcctca | 540 |
| agctatctgt ctctgacacc cgaacagtgg aaaagtcaca ggtcatatag ctgccaggtg | 600 |
| actcacgagg gctcaactgt ggagaaaacc gtcgcaccaa ccgaatgttc c | 651 |

<210> SEQ ID NO 18
<211> LENGTH: 654
<212> TYPE: DNA
<213> ORGANISM: Artificial Sequence
<220> FEATURE:
<223> OTHER INFORMATION: H3 V(lambda)-C(kappa) chimeric light chain

<400> SEQUENCE: 18

| | |
|---|---|
| cagagcgcac tgactcagcc tgcatccgtg tccgggtccc ctgggcagag cattactatt | 60 |
| tcatgtactg gaacttcttc agacgtgggc gggtacaact tcgtgtcctg gtatcagcag | 120 |
| caccccggca aggcacctaa actgatgatc tacgacgtga cgatcgacc aagcggggtc | 180 |
| tccgacagat tttctggaag taaatcaggc aataccgcct ctctgatcat tagtgggctg | 240 |
| caggccgacg atgaggctga ttactattgc agctcctatg gatctagtag cacccatgtc | 300 |
| attttcggag gcggaacaaa ggtcaccgtc ctgagaaccg tggcggcgcc cagtgtcttc | 360 |
| atttttcccc ctagcgacga acagctgaag tctgggacag ccagtgtggt ctgtctgctg | 420 |
| aacaacttct accctcgcga ggctaaagtg cagtggaagg tcgataacgc actgcagtcc | 480 |
| ggaaattctc aggagagtgt gactgaacag gactcaaaag atagcaccta ttccctgtca | 540 |
| agcacactga ctctgagcaa ggccgactac gagaagcata agtgtatgc ttgtgaagtc | 600 |
| acccaccagg ggctgagttc accagtcaca aaatcattca acagagggga gtgc | 654 |

<210> SEQ ID NO 19
<211> LENGTH: 720
<212> TYPE: DNA
<213> ORGANISM: Artificial Sequence
<220> FEATURE:
<223> OTHER INFORMATION: EP6b_B01 heavy chain Fab

<400> SEQUENCE: 19

| | |
|---|---|
| cagctgcagc tgcaggaaag cgggcctggg ctggtgaaac cttccgaaac actgtccctg | 60 |
| acttgtactg tgagcggggc atcaattagt gccaactcat actatggcgt gtgggtccga | 120 |
| cagagtccag gaaagggact ggagtgggtg gggtccatcg cctacagagg aaacagtaat | 180 |
| tcaggcagca catactataa ccctagcctg aagtccaggg ctactgtgag cgtggacagc | 240 |
| tccaaaaatc aggtgtcact gcgcctgact agcgtcaccg ccgctgatac cgccctgtac | 300 |
| tattgcgctc ggagacagct gctggacgat ggacaggat accagtgggc agccttcgac | 360 |
| gtgtggggac aggggacaat ggtgactgtc tctagtgcta gcaccaaggg gccaagcgtg | 420 |
| ttcccactgg cacccctcaag caaatccacc tctggaggaa cagctgcact gggatgcctg | 480 |
| gtgaaggatt atttccccga acctgtgact gtctcttgga atagtggggc actgacttct | 540 |
| ggagtgcaca ccttttccgc cgtcctgcag tcctctggac tgtactccct gagttcagtg | 600 |

```
gtcacagtgc ctagctcctc tctgggcacc cagacataca tctgtaacgt gaaccataag    660
ccatcaaaca ctaaagtcga caagaaggtg gagccaaagt cctgtgacaa gacccataca    720
```

<210> SEQ ID NO 20
<211> LENGTH: 648
<212> TYPE: DNA
<213> ORGANISM: Artificial Sequence
<220> FEATURE:
<223> OTHER INFORMATION: EP6b_B01 light chain (lambda)

<400> SEQUENCE: 20

```
cagagcgtcc tgactcagcc tcctccgtg tccgaagcac ctcggcagac tgtgactatc     60
tcatgttctg gcaactcatc aaatatcgga aggtacccag tgaactggta tcagcagctg    120
cccggcaagg cacctaaact gctgatctac agtgacaatc tgcggttctc aggggtcccc    180
gatcggttca gcggctccaa gtctgggacc acagccagcc tggctattcg ggacctgctg    240
tccgaggacg aagccgatta ctattgcagt acctgggacg ataccctgga aggatgggtc    300
ttcggcggcg gcacaaaagt caccgtcctg ggcagccaa aggcggcgcc cagtgtcaca    360
ctgtttcccc ctagctccga ggaactgcag gctaacaaag caacactggt gtgtctgatc    420
agcgacttct accctggagc tgtgactgtc gcctggaagg ctgattctag tccagtgaaa    480
gcaggcgtcg agaccacaac tccctctaag cagagtaaca caagtacgc agcctcaagc    540 tatctgtcac tgaccccaga acagtggaag agccaccgga gctattcctg ccaggtcact    600
cacgaaggct ccactgtcga gaaaccgtc gctcccaccg aatgttca              648
```

<210> SEQ ID NO 21
<211> LENGTH: 651
<212> TYPE: DNA
<213> ORGANISM: Artificial Sequence
<220> FEATURE:
<223> OTHER INFORMATION: EP6b_B01 V(lambda)-C(kappa) chimeric light
      chain

<400> SEQUENCE: 21

```
cagagcgtcc tgactcagcc tccttccgtg tccgaggcac ccgccagac cgtgactatc     60 tcatgttccg gcaactcctc aaatatcgga aggtacccag tgaactggta tcagcagctg    120
cccggcaagg cacctaaact gctgatctac agtgacaatc tgcggttctc aggggtcccc    180
gatcggttca gcggctccaa gtctgggacc acagccagcc tggctattcg ggacctgctg    240
tccgaggacg aagccgatta ctattgcagt acctgggatg ataccctgga aggatgggtc    300
tttggaggag gaactaaagt caccgtgctg agaaccgtgg cggcgcccag tgtcttcatt    360 tttccccta gcgacgaaca gctgaagtct gggacagcca gtgtggtctg tctgctgaac    420
aacttctacc ctagagaggc taaagtgcag tggaaggtcg ataacgcact gcagtccgga    480
aattctcagg agagtgtgac tgaacaggac tcaaaagata gcacctattc cctgtcaagc    540
acactgactc tgagcaaggc cgactacgag aagcataaag tgtatgcttg tgaagtcacc    600 caccagggg tgagttcacc agtcacaaaa tcattcaaca gaggggagtg c             651
```

<210> SEQ ID NO 22
<211> LENGTH: 678
<212> TYPE: DNA
<213> ORGANISM: Artificial Sequence
<220> FEATURE:
<223> OTHER INFORMATION: CAT-2200 heavy chain Fab

<400> SEQUENCE: 22

```
gaggtgcagc tgctggaatc tggggggggc ctggtgcagc ctgggggggtc cctgagactg      60 tcatgtgctg ccagcgggtt tactttcagc tcctacgcta tgtcctgggt gcgacaggca     120
cccgggaagg gactggagtg ggtctctgca atcagtgggt caggcgggag tacttactat     180
gccgacagcg tgaagggacg gttcactatc tcaagagata cagcaagaa caccctgtat      240 ctgcagatga acagcctgag agcagaagac acagccgtgt actattgcgc agggatctg      300 atccacggag tcactcgcaa ttggggccag gggactctgg tgaccgtctc tagtgctagc     360
acaaaggggc cctctgtgtt tccactggcc ccctcaagca aaagcacatc cggaggaact     420
gcagctctgg gatgtctggt gaaggactac ttcccccagc ctgtgaccgt ctcttggaac     480
agtggagccc tgaccagcgg cgtgcacaca tttcctgctg tcctgcagtc ctctggcctg     540
tactccctga gttcagtggt cacagtgcct agctcctctc tggggaccca gacatatatt     600
tgcaacgtga atcataaacc aagcaacact aaggtcgaca gaaagtgga gcccaagagc      660 tgtgataaaa ctcatacc                                                   678

<210> SEQ ID NO 23
<211> LENGTH: 648
<212> TYPE: DNA
<213> ORGANISM: Artificial Sequence
<220> FEATURE:
<223> OTHER INFORMATION: CAT-2200 light chain (lambda)

<400> SEQUENCE: 23
aactttatgc tgactcagcc ccactccgtg tccgagagcc ctggcaaaac tgtgactatt      60
tcatgtaccc gatcatctgg aagcctggcc aactactatg tgcagtggta ccagcagagg     120
ccaggcagct cccccactat cgtgattttc gctaacaatc agcggccttc cggcgtccca     180
gacagatttt ccgggtctat cgattctagt tcaaatagtg catcactgac tatttccggg     240
ctgaagaccg aggacgaagc cgattactat tgccagacct acgacccta ttctgtggtc      300 ttcggcgggg gaaccaagct gacagtgctg ggacagccaa agcggcgcc cagtgtcaca      360 ctgtttcccc ctagctccga ggaactgcag gctaacaaag caacactggt gtgtctgatc     420
agcgacttct accctggagc tgtgactgtc gcctggaagg ctgattctag tccagtgaaa     480
gcaggcgtcg agaccacaac tcccctctaag cagagtaaca acaagtacgc agcctcaagc    540
tatctgtcac tgaccccaga acagtggaag agccaccgga gctattcctg ccaggtcact     600
cacgaaggct ccactgtcga gaaaaccgtc gctcccaccg aatgttca                  648

<210> SEQ ID NO 24
<211> LENGTH: 651
<212> TYPE: DNA
<213> ORGANISM: Artificial Sequence
<220> FEATURE:
<223> OTHER INFORMATION: CAT-2200 V(lambda)-C(kappa) chimeric light
      chain

<400> SEQUENCE: 24
aactttatgc tgacacagcc tcactctgtg agtgagtcac ccggaaagac cgtcacaatc      60
tcttgcacta ggagctccgg cagcctggca aactactatg tgcagtggta ccagcagcgg     120
cccgggtcta gtcctaccat cgtgattttc gccaacaatc agcgaccatc cggagtccca     180
gaccggttca gcgggtccat cgattcaagc tccaattctg ccagtctgac tattagcggc     240 ctgaaaccg aggacgaagc tgattactat tgtcagacat acgatccata tagcgtggtc      300
tttggcggag gaactaagct gaccgtgctg agaaccgtgg cggcgcccag tgtcttcatt     360
```

```
tttcccccta gcgacgaaca gctgaagtct gggacagcca gtgtggtctg tctgctgaac        420
aacttctacc ctagagaggc taaagtgcag tggaaggtcg ataacgcact gcagtccgga        480
aattctcagg agagtgtgac tgaacaggac tcaaaagata gcacctattc cctgtcaagc        540
acactgactc tgagcaaggc cgactacgag aagcataaag tgtatgcttg tgaagtcacc        600
caccaggggc tgagttcacc agtcacaaaa tcattcaaca gaggggagtg c                651
```

<210> SEQ ID NO 25
<211> LENGTH: 681
<212> TYPE: DNA
<213> ORGANISM: Artificial Sequence
<220> FEATURE:
<223> OTHER INFORMATION: Pertuzumab heavy chain Fab

<400> SEQUENCE: 25

```
gaagtgcagc tggtcgaatc tggaggagga ctggtgcagc caggagggtc cctgcgcctg         60
tcttgcgccg ctagtggctt cacttttacc gactacacca tggattgggt gcgacaggca        120
cctggaaagg gcctggagtg ggtcgccgat gtgaacccaa atagcggagg ctccatctac        180
aaccagcggt tcaagggccg gttcaccctg tcagtggacc ggagcaaaaa caccctgtat        240
ctgcagatga atagcctgcg agccgaagat actgctgtgt actattgcgc ccggaatctg        300
gggccctcct tctactttga ctattggggg cagggaactc tggtcaccgt gagctccgcc        360
tccaccaagg gaccttctgt gttcccactg gctccctcta gtaaatccac atctggggga        420
actgcagccc tgggctgtct ggtgaaggac tacttcccag cccgtcac agtgtcttgg         480 aacagtggcg ctctgacttc tggggtccac acctttcctg cagtgctgca gtcaagcggg        540
ctgtacagcc tgtcctctgt ggtcaccgtg ccaagttcaa gctgggaac acagacttat         600 atctgcaacg tgaatcacaa gccatccaat acaaaagtcg acaagaaagt ggaacccaag        660
tcttgtgata aacccatac a                                                   681
```

<210> SEQ ID NO 26
<211> LENGTH: 642
<212> TYPE: DNA
<213> ORGANISM: Artificial Sequence
<220> FEATURE:
<223> OTHER INFORMATION: Pertuzumab light chain (kappa)

<400> SEQUENCE: 26

```
gatattcaga tgacccagtc cccaagctcc ctgagtgcct cagtgggcga ccgagtcacc         60
atcacatgca aggcttccca ggatgtgtct attggagtcg catggtacca gcagaagcca        120
ggcaaagcac ccaagctgct gatctatagc gcctcctacc ggtataccgg cgtgccctct        180
agattctctg gcagtgggtc aggaacagac tttactctga ccatctctag tctgcagcct        240
gaggatttcg ctacctacta ttgccagcag tactatatct acccatatac ctttggccag        300
gggacaaaag tggagatcaa gaggactgtg gccgctccct ccgtcttcat tttccccct         360 tctgacgaac agctgaaaag tggcacagcc agcgtggtct gtctgctgaa caatttctac        420
cctcgcgaag ccaaagtgca gtggaaggtc gataacgctc tgcagagcgg caacagccag        480
gagtctgtga ctgaacagga cagtaaagat tcaacctata gcctgtcaag cacactgact        540
ctgagcaagg cagactacga gaagcacaaa gtgtatgcct gcgaagtcac acatcagggg        600
ctgtcctctc ctgtgactaa gagctttaac agaggagagt gt                           642
```

<210> SEQ ID NO 27

```
<211> LENGTH: 700
<212> TYPE: DNA
<213> ORGANISM: Artificial Sequence
<220> FEATURE:
<223> OTHER INFORMATION: D3H44 heavy chain Fab

<400> SEQUENCE: 27
gaggtccagc tggtcgagtc tggaggagga ctggtgcagc caggagggag cctgcgactg    60
tcctgcgccg cttctggctt caacatcaag gaatactata tgcactgggt gagacaggca   120
ccaggcaaag gactggagtg ggtgggcctg atcgaccctg aacaggggaa caccatctac   180
gacccaaagt ttcaggatcg ggccactatt agtgctgaca actcaaaaaa taccgcatat   240
ctgcagatga acagcctgag gcagaggat acagccgtgt actattgcgc ccgggacact   300
gcagcctact tcgattattg gggacagggc acactggtca ctgtgagctc cgctagcact   360
aagggggcctt ccgtgtttcc actggctccc tctagtaaat ccacctctgg aggcacagct   420
gcactgggat gtctggtgaa ggattacttc cctgaaccag tcacagtgag ttggaactca   480
ggggctctga caagtggagt ccatactttt ccgcagtgc tgcagtcaag cggactgtac   540
tccctgtcct ctgtggtcac cgtgcctagt tcaagcctgg gcacccagac atatatctgc   600
aacgtgaatc acaagccatc aaatacaaaa gtcgacaaga agtggagcc caagagctgt   660
gataaaactc atacctgccc accttgtccg gcgccagaac                         700

<210> SEQ ID NO 28
<211> LENGTH: 642
<212> TYPE: DNA
<213> ORGANISM: Artificial Sequence
<220> FEATURE:
<223> OTHER INFORMATION: D3H44 light chain (kappa)

<400> SEQUENCE: 28
gacatccaga tgacccagtc ccctagctcc ctgtccgcct ctgtgggcga cagggtgacc    60
atcacatgcc gggccagcag agatatcaag tcctacctga actggtatca gcagaagccc   120
ggcaaggccc ctaaggtgct gatctactat gccacatctc tggccgaggg agtgccaagc   180
cgcttcagcg gctccggctc tggaaccgac tacaccctga caatctctag cctgcagcca   240
gaggatttcg ccacatacta ttgtctgcag cacggcgagt ctccctggac ctttggccag   300
ggcacaaagg tggagatcaa gcggaccgtg gcggcgccca gtgtcttcat tttccccct   360
agcgacgaac agctgaagtc tggacagcc agtgtggtct gtctgctgaa caacttctac   420
cctagagagg ctaaagtgca gtggaaggtc gataacgcac tgcagtccgg aaattctcag   480
gagagtgtga ctgaacagga ctcaaaagat agcacctatt ccctgtcaag cacactgact   540
ctgagcaagg ccgactacga gaagcataaa gtgtatgctt gtgaagtcac ccaccagggg   600
ctgagttcac cagtcacaaa atcattcaac agagggagt gc                       642

<210> SEQ ID NO 29
<211> LENGTH: 217
<212> TYPE: PRT
<213> ORGANISM: Homo sapiens
<220> FEATURE:
<223> OTHER INFORMATION: IgG1 Fc sequence 231-447

<400> SEQUENCE: 29

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                 70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 30
<211> LENGTH: 10
<212> TYPE: PRT
<213> ORGANISM: Artificial Sequence
<220> FEATURE:
<223> OTHER INFORMATION: Upper IgG1 hinge

<400> SEQUENCE: 30

Glu Pro Lys Ser Cys Asp Lys Thr His Thr
1               5                   10

<210> SEQ ID NO 31
<211> LENGTH: 107
<212> TYPE: PRT
<213> ORGANISM: Artificial Sequence
<220> FEATURE:
<223> OTHER INFORMATION: C(kappa) (CH1) domain of IGKC*01

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
 65                 70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys

```
                100             105

<210> SEQ ID NO 32
<211> LENGTH: 5
<212> TYPE: PRT
<213> ORGANISM: Artificial Sequence
<220> FEATURE:
<223> OTHER INFORMATION: Lower IgG1 hinge

<400> SEQUENCE: 32

Cys Pro Pro Cys Pro
1               5
```

STABILIZED CHIMERIC FABS

The instant application contains a Sequence Listing which has been submitted via EFS-Web and is hereby incorporated by reference in its entirety. Said ASCII copy, created on Jun. 27, 2018, is named 2018-06-27 (097993-1092280 (001610WO)) Sequence Listing.txt, and is 45 bytes in size.

BACKGROUND

Antibodies find use in many applications, including as research tools, as diagnostics and, of course as therapeutics, all of which require the manufacture of antibodies in large quantities. Physical properties of antibodies, such as thermal stability, can affect the manufacturability of antibodies. For example, antibodies with low thermal stability, or those that aggregate are difficult to manufacture and store.

Naturally occurring antibodies and those that have been artificially generated (for example by phage display, or recombinant engineering) exhibit a range of thermal stabilities, with artificially generated antibodies often having a level of thermal stability that makes them difficult to manufacture (McConnell et al. (2014) mAbs: 6:1274-1282). Moreover, it has been suggested that in antibodies identified from a synthetic Fab library, the average melting temperature of antibodies containing variable domains from lambda light chains was lower than that of antibodies containing variable domains from kappa light chains (Tiller et al. (2013) Mabs 5:3, 445-470).

Chimeric Fabs comprising chimeric light chains can be constructed for several purposes. For example, chimeric Fabs can be generated upon conversion of phage display-generated scFvs into Fab format to obtain an antibody in a naturally occurring format. Additionally, mouse-human chimeric antibodies can be constructed for reducing the immunogenicity of mouse antibodies in humans. Chimeric Fabs may comprise a variable lambda domain and constant kappa domain (Vlambda-Ckappa) or a variable kappa domain and a constant lambda domain (Vkappa-Clambda). Chimeric Fabs having a chimeric light chain often exhibit a decrease in thermal stability relative to a Fab comprising the parent lambda light chain.

Thus, there is a need to increase the thermal stability of chimeric Fabs, as well as that of antibodies having lambda light chains, in order to improve their manufacturability.

BRIEF SUMMARY

The present disclosure provides stabilized chimeric Fabs. In one aspect, there is provided a stabilized chimeric Fab or chimeric heterodimer comprising: a first immunoglobulin heavy chain polypeptide construct (H1) comprising a heavy chain constant domain 1 (CH1) sequence and a heavy chain variable domain (VH) sequence, and a first chimeric immunoglobulin light chain polypeptide construct (L1) comprising a kappa light chain constant domain (Ckappa) sequence and a lambda light chain variable domain (Vlambda) sequence, the Vlambda sequence comprising one or more stabilizing amino acid modifications that increase the thermal stability of the chimeric heterodimer compared to a corresponding wild-type chimeric heterodimer without the stabilizing amino acid substitutions, wherein H1 and L1 form a first Fab region that binds to a first epitope.

In another aspect, there is provided an antibody construct comprising: a first heterodimer, wherein the first heterodimer is the stabilized chimeric Fab or chimeric heterodimer described herein, and a scaffold, wherein at least one of H1 and L1 of said first heterodimer is linked with or without a linker to the scaffold.

In another aspect, there is provided a pharmaceutical composition comprising the stabilized chimeric Fab or chimeric heterodimer, or the antibody construct described herein, and a pharmaceutically acceptable carrier.

In another aspect, there is provided a polynucleotide or set of polynucleotides encoding the stabilized chimeric Fab or chimeric heterodimer, or the antibody construct described herein.

In another aspect, there is provided a vector or set of vectors comprising one or more of the polynucleotides or sets of polynucleotides described herein.

In another aspect, there is provided an isolated cell comprising the polynucleotide, the set of polynucleotides, the vector, or the set of vectors described herein.

In another aspect, there is provided a method of preparing the stabilized chimeric Fab or chimeric heterodimer, or the antibody construct described herein, comprising the steps of: obtaining a host cell comprising a polynucleotide or set of polynucleotides encoding the chimeric heterodimer or antibody construct; culturing the host cell in a host cell culture under conditions that allow expression of the chimeric heterodimer or antibody construct, and collecting the chimeric heterodimer or antibody construct from the host cell culture.

In another aspect, there is provided a chimeric light chain polypeptide construct comprising a kappa light chain constant domain (Ckappa) sequence and a lambda light chain variable domain (Vlambda) sequence, the Vlambda sequence comprising one or more stabilizing amino acid substitutions that increases the thermal stability of a chimeric heterodimer comprising the chimeric light chain.

In another aspect, there is provided a pharmaceutical composition comprising the chimeric light chain polypeptide construct described herein, and a pharmaceutically acceptable carrier.

In another aspect, there is provided a polynucleotide encoding the chimeric light chain polypeptide construct described herein.

In another aspect, there is provided a method of increasing the thermal stability of an antibody comprising a lambda immunoglobulin light chain and an immunoglobulin heavy chain, the method comprising: preparing a Vlambda-Ckappa chimeric light chain comprising the Vlambda sequence of the antibody, and a Ckappa sequence from an antibody having a kappa light chain, wherein the Vlambda sequence comprises one or more stabilizing amino acid modifications, and expressing the Vlambda-Ckappa chimeric light chain with the immunoglobulin heavy chain to obtain an antibody with increased thermal stability.

In another aspect, there is provided a method of treating cancer, autoimmune disease, an inflammatory disorder or an infectious disease in a subject comprising administering an effective amount of a chimeric heterodimer or antibody construct described herein to a subject or patient.

In another aspect, the use of an effective amount of a chimeric heterodimer or an antibody construct described herein in the treatment of cancer, autoimmune disease, an inflammatory disorder or an infectious disease in a subject is provided. In one embodiment, use of a chimeric heterodimer or an antibody construct described herein in the preparation of a medicament for the treatment of cancer, autoimmune disease, an inflammatory disorder or an infectious disease is provided. In another embodiment, a chimeric heterodimer or antibody construct described herein for use in the treatment of cancer, autoimmune disease, an inflammatory disorder or an infectious disease in a subject is provided.

BRIEF DESCRIPTION OF THE DRAWINGS

FIG. 2 shows the sequence of an exemplary Vlambda-Ckappa chimeric light chain construct, for the antibody CAT-2200. The WT lambda light chain sequence corresponding to CAT-2200 (from PDB entry 2VXS, chain L) is aligned with the Vlambda-Ckappa chimeric light chain construct based on the CAT-2200 antibody to highlight the differences between the two constructs. Vlambda-Ckappa chimeric light chain construct is composed of the lambda variable domain sequence of CAT-2200 terminating at residue L106A and kappa constant domain sequence corresponding to IGKC*01 starting at position R108. An asterisk (*) indicates positions which have a single conserved residue; a colon (:) indicates conservation between groups of strongly similar properties; a period (.) indicates conservation between group of weakly similar properties; and no consensus symbol indicates very different residues, as referenced on the EMBL-EBI website.

FIG. 3A depicts a schematic representation of a Fab. The region corresponding to the boxed area has been magnified in FIGS. 3B to 3D. FIG. 3B highlights hot spot residues 83, 85 and 105 at the Vkappa-Ckappa interface (D3H44 antibody, PDB:1jpt). FIG. 3C depicts the Vlambda-Clambda interface (CAT-2200 antibody, PDB:2 Arm), also highlighting residues 83, 85 and 105. FIG. 3D depicts an unoptimized Vlambda-Ckappa interface (antibody S4, PDB: 3nps), again highlighting residues 83, 85 and 105.

FIG. 6A shows the thermal stability of stabilized chimeric Fabs based on the CAT-2200 lambda antibody; and FIG. 6B shows the thermal stability of stabilized chimeric Fabs based on the H3 lambda antibody. The change in Tm (measured by DSF) of the stabilized chimeric Fab compared to that of the respective parent chimeric Fab is plotted for number of theme designs.

FIGS. 10A, 10C, and 10E show the UPLC-SEC profiles for the wild-type lambda Mab at days 0, 20, and 30, respectively. FIGS. 10B, 10D, and 10F show the UPLC-SEC profiles for a stabilized Mab having stabilizing amino acid modifications corresponding to design 37 at days 0, 20 30, respectively.

DETAILED DESCRIPTION

Figure 1:
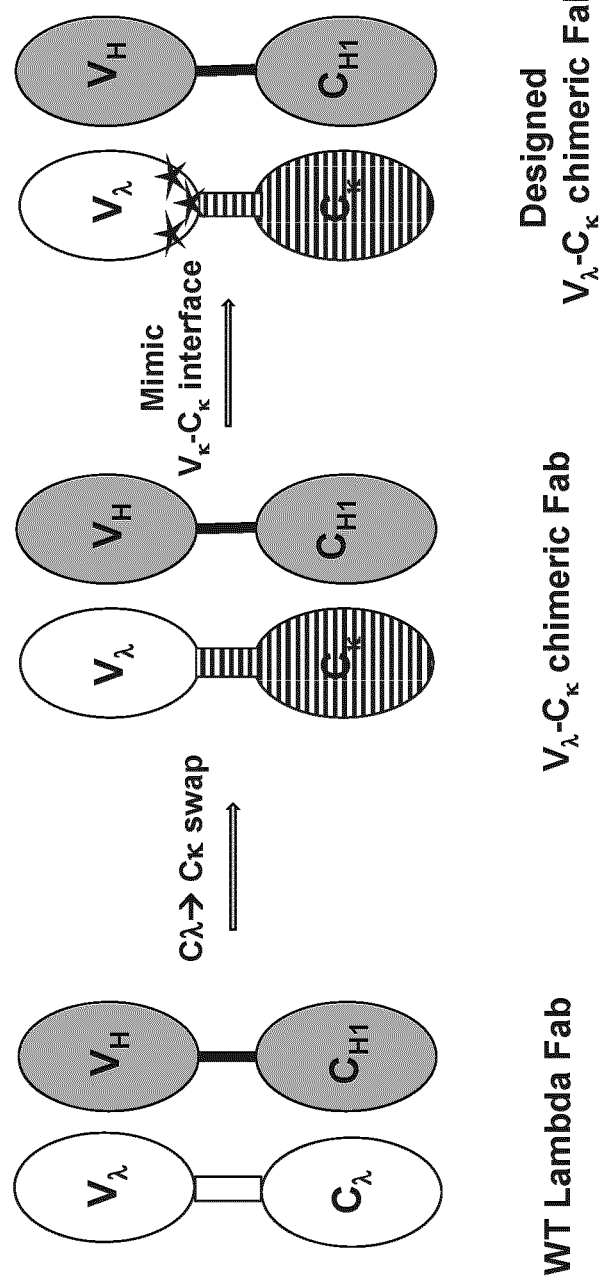
FIG. 1 depicts a schematic representation of a Vlambda-Ckappa chimeric Fab and the engineering approach taken to improve thermal stability of the Vlambda-Ckappa chimeric Fab. A WT (wild-type) lambda Fab (also referred to as a parent lambda Fab) is shown, having a wild-type heavy chain Fab sequence (VH and CH1 domains, grey fill) and a wild-type lambda light chain (white fill). This parent lambda Fab can be engineered into a parent chimeric Fab (Vlambda-Ckappa chimeric Fab) by swapping the Clambda sequence of the parent lambda light chain with a Ckappa sequence to form a Vlambda-Ckappa chimeric light chain construct. Thus, the Vlambda-Ckappa chimeric light chain construct comprises a Vlambda sequence from the parent lambda Fab (white fill) fused to a Ckappa sequence (hashed fill). The thermal stability of the parent chimeric Fab can be increased by introducing mutations in the Vlambda sequence to mimic the interface observed between variable kappa and constant kappa domains (Vkappa-Ckappa), resulting in improved compatibility of the Vlambda-Ckappa interface. This stabilized chimeric Fab is depicted in FIG. 1 as "designed Vlambda-Ckappa chimeric Fab," where star symbols represent the stabilizing amino acid modifications (also referred to as a stability optimization design). Parent chimeric Fabs are also referred to herein as "wild-type chimeric heterodimers".
Figure 3A:
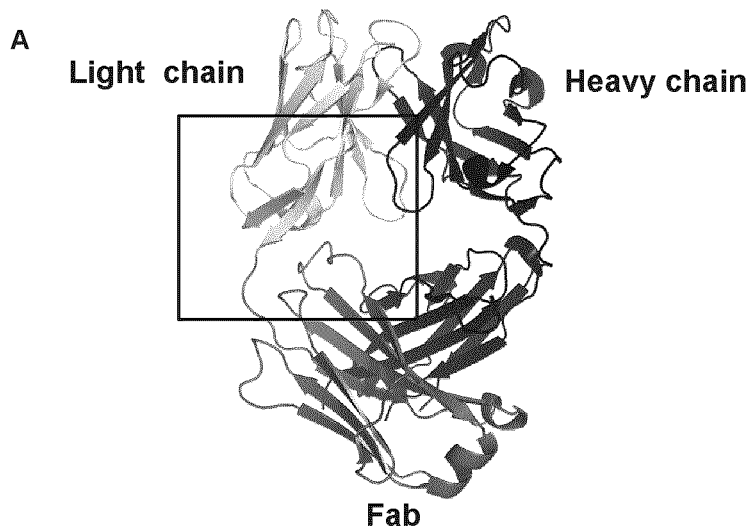
FIG. 3A-3D depicts ribbon diagrams of the variable domain-constant domain interface in the light chain.
Figure 3B:
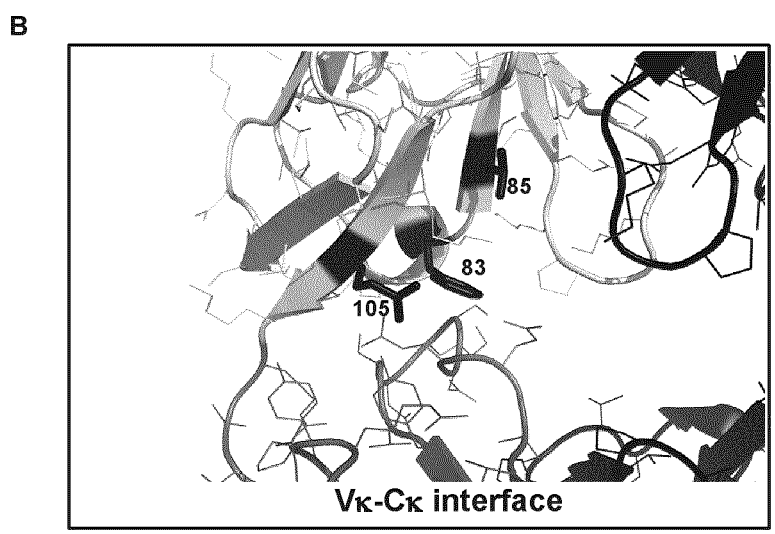
Figure 3C:
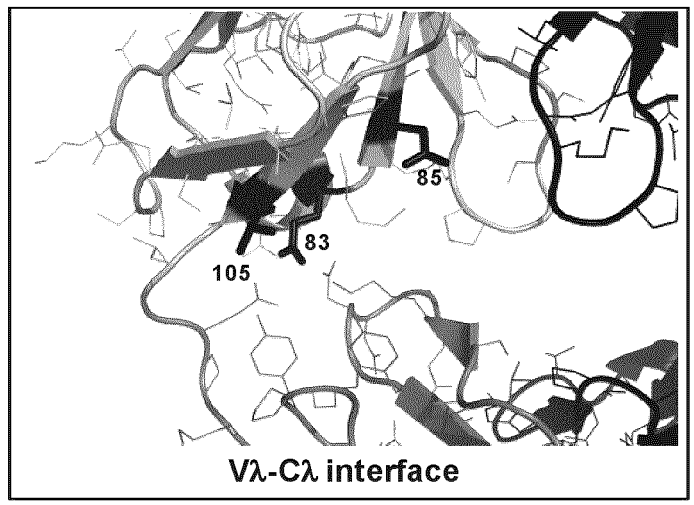
Figure 3D:
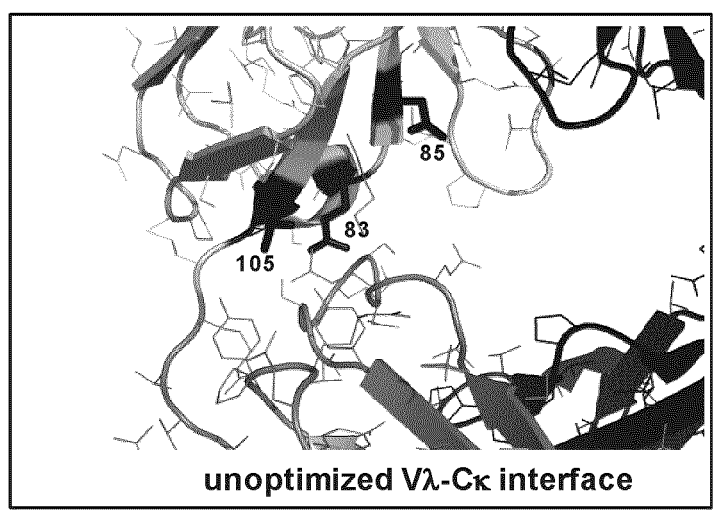

Chimeric Fabs are Fabs that comprise a chimeric light chain. In the context of the present disclosure, chimeric Fabs may comprise a chimeric light chain construct having a light chain variable domain sequence from a lambda light chain (Vlambda sequence) and a light chain constant domain sequence from a kappa light chain (Ckappa sequence). Such chimeric light chains are referred to herein as Vlambda-Ckappa chimeric light chains (Vlambda-Ckappa chimeric light chains). In many cases, chimeric Fabs with a Vlambda-Ckappa chimeric light chain can exhibit a decrease in thermal stability compared to a parent Fab comprising a wild-type lambda light chain. Furthermore, many antibodies having lambda light chains exhibit thermal stability that is decreased compared to antibodies having kappa light chains. A decrease in thermal stability can lead to difficulties in manufacturing antibodies containing such chimeric Fabs in the necessary quantity, and with the necessary quality required for therapeutic antibody development.

Provided herein are stabilized chimeric Fabs comprising a modified Vlambda-Ckappa chimeric light chain construct and a heavy chain comprising a VH and a CH1 domain. The modified Vlambda-Ckappa chimeric light chain construct comprises a Vlambda sequence comprising one or one or more stabilizing amino acid modifications that increase the thermal stability of the chimeric Fab. In some embodiments, the stabilizing amino acid modifications are at one or more amino acid residues at the interface between the Vlambda and Ckappa domains. In some embodiments, the stabilized chimeric Fab can exhibit a thermal stability that is even greater than that of a corresponding wild-type Fab having a wild-type lambda light chain (wild-type lambda Fab). The stabilizing amino acid modifications are transferable across different antibody systems and have little or no impact on the ability of the stabilized chimeric Fab to bind antigen. When Vlambda-Ckappa chimeric light chain constructs having the stabilizing amino acid modifications are present in the context of an antibody in a Mab format, the stabilizing amino acid modifications do not affect the ability of the antibody to bind to Fc gamma receptors or FcRn.

The stabilized chimeric Fabs are useful as therapeutic polypeptides, or can be used to prepare antibody constructs in other formats, including the Mab format or other antibody formats where a Vlambda-Ckappa chimeric light chain is present. The stabilized chimeric Fabs may also be useful generally to increase the stability of antibodies having lambda light chains. In this context, the parent lambda antibody can be prepared with Vlambda-Ckappa chimeric light chain constructs including the stabilizing amino acid modifications to increase thermal stability.

Definitions

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±1%, 2%, 3%, 4%, 5%, 6%, 7%, 8%, 9% or 10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or immunoglobulin constructs derived from various combinations of the structures and substituents described herein are disclosed by the present application to the same extent as if each single chain polypeptide or stabilized chimeric Fab were set forth individually. Thus, selection of particular components to form individual single chain polypeptides or stabilized chimeric Fabs is within the scope of the present disclosure.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

In the present application, amino acid names and atom names (e.g. N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985). The term "amino acid residue" is primarily intended to indicate an amino acid residue contained in the group consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "nucleotide sequence" or "nucleic acid sequence" is intended to indicate a consecutive stretch of two or more nucleotide molecules. The nucleotide sequence can be of genomic, cDNA, RNA, semisynthetic or synthetic origin, or any combination thereof.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing a nucleic acid sequence into a cell.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refer to compounds that have the same basic chemical structure as a naturally occurring amino acid, i.e., a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as alanine, ornithine, etc.; and chemically synthesized compounds having properties known in the art to be characteristic of amino acids. Examples of non-naturally occurring amino acids include, but are not limited to, N-methyl amino acids (e.g. methyl alanine), D-amino acids, histidine-like amino acids (e.g., 2-amino-histidine, hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the stabilized chimeric Fabs described herein can be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids are referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that may be considered conservative substitutions for one another:

1. Alanine (A), Glycine (G);
2. Aspartic acid (D), Glutamic acid (E);
3. Asparagine (N), Glutamine (Q);
4. Arginine (R), Lysine (K);
5. Isoleucine (I), Leucine (L), Methionine (M), Valine (V);
6. Phenylalanine (F), Tyrosine (Y), Tryptophan (W); and
7. Serine (S), Threonine (T), Cysteine (C); (see, e.g., Creighton, Proteins: Structures and Molecular Properties (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" or "substantially similar" if they have a percentage of amino acid residues or nucleotides that are the same (i.e., at least about 50%, 55%, 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the stabilized chimeric Fabs described herein, including homologs from species other than human, can be obtained by a process comprising the steps of screening a library under stringent hybridization conditions with a labeled probe having a polynucleotide sequence of the stabilized chimeric Fabs described herein or a fragment thereof, and isolating full-length cDNA and genomic clones containing said polynucleotide sequence. Such hybridization techniques are well known to the skilled artisan.

Examples of an algorithm that is suitable for determining percent sequence identity and sequence similarity are the BLAST™ and BLAST™ 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST™ analyses is publicly available through the National Center for Biotechnology Information (see the internet at www.ncbi.nlm.nih.gov). Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. Examples of algorithm parameters for the BLASTN program (for nucleotide sequences) are wordlength (W) of 11, an expectation (E) of 10, M=5, N=-4 and a comparison of both strands. For amino acid sequences, examples of algorithm parameters for the BLASTP program are wordlength of 3, expectation (E) of 10, and the BLOSUM62 scoring matrix (see Henikoff and Henikoff, *Proc. Natl. Acad. Sci. USA* 89:10915, 1989).

A derivative, or a variant of a polypeptide is said to share "homology" or be "homologous" with the peptide if the amino acid sequences of the derivative or variant has at least 50% identity over a sequence that is 100 amino acids in length from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

As used herein, an "isolated" polypeptide or construct means a construct or polypeptide that has been identified and separated and/or recovered from a component of its natural cell culture environment. Contaminant components of its natural environment are materials that would typically interfere with diagnostic or therapeutic uses for the stabilized chimeric Fab or antibody constructs comprising the stabilized chimeric Fab, and can include enzymes, hormones, and other proteinaceous or non-proteinaceous solutes.

In certain embodiments, as used herein, "isolated" antibody constructs describe antibody constructs, including stabilized chimeric Fabs, that have been identified and separated and/or recovered from a component of its natural cell culture environment. For example, stabilized chimeric Fab described herein comprises a heavy chain Fab sequence and a Vlambda-Ckappa chimeric light chain construct (a heterodimer) or "isolated" heterodimer that has been identified and separated and/or recovered from a component of its natural cell culture environment. Contaminant components of its natural environment are materials that would interfere with diagnostic or therapeutic uses for the heterodimer or antibody constructs, and can include enzymes, hormones, and other proteinaceous or non-proteinaceous solutes.

The stabilized chimeric Fabs and antibody constructs comprising same can be purified to substantial homogeneity. The phrases "substantially homogeneous", "substantially homogeneous form" and "substantial homogeneity" are used to indicate that the correctly paired product is substantially devoid of by-products originating from undesired polypeptide combinations (e.g. homodimers or mispaired heterodimers). In one embodiment, a purified stabilized chimeric Fab is substantially devoid of light chain dimers. In one embodiment, in the context of a bispecific antibody construct, where H1 (heavy chain 1), L1 (light chain 1), H2 (heavy chain 2), and L2 (light chain 2) are expressed, the correctly paired product is a heterodimer pair comprising correctly paired H1L1 and H2L2 (H1L1H2L2). In some embodiments, in the context of a bispecific antibody construct, where H1, L1, H2, and L2 are expressed, the correctly paired product can comprise additional products that exhibit correct pairing in at least one Fab region such as, for example, H1L1H2L1 or H1L2H2L2, or where "half antibodies" are produced, H1L1 or H2L2 (see FIG. 11). Expressed in terms of purity, in one embodiment, substantial homogeneity means that the amount of completely mispaired by-products does not exceed 20%, for example is below 10%, below 5%, below 1%, or below 0.5% of the total LC-MS intensity from all species present in the mixture, wherein the percentages reflect results from Mass Spectrometric analysis.

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

As used herein, the terms "antibody" and "immunoglobulin" or "antibody construct" are used interchangeably. An "antibody construct" refers to a polypeptide substantially encoded by an immunoglobulin gene or immunoglobulin genes, or one or more fragments thereof, which specifically bind an analyte (eptitope or antigen). The recognized immunoglobulin genes include the kappa, lambda, alpha, gamma, delta, epsilon and mu constant region genes, as well as the myriad immunoglobulin variable region genes. Light chains are classified as either kappa or lambda Heavy chains are classified as gamma, mu, alpha, delta, or epsilon, which in turn define the immunoglobulin classes, IgG, IgM, IgA, IgD, and IgE, respectively. Further, the antibody can belong to one of a number of subtypes, for instance, the IgG can belong to the IgG1, IgG2, IgG3, or IgG4 subclasses. Antibodies comprising a kappa light chain are referred to herein as "kappa antibodies," while antibodies comprising a lambda light chain are referred to herein as "lambda antibodies."

An exemplary immunoglobulin (antibody) structural unit is composed of two pairs of polypeptide chains, each pair having one immunoglobulin "light" (about 25 kD) and one immunoglobulin "heavy" chain (about 50-70 kD). This type of immunoglobulin or antibody structural unit is considered to be "naturally occurring," and is also referred to herein as a "Mab" format. The term "light chain" includes a full-length light chain and fragments thereof having sufficient variable domain sequence to confer binding specificity. A full-length light chain includes a variable domain, VL, and a constant domain, CL. The variable domain of the light chain is at the amino-terminus of the polypeptide. Light chains include kappa chains and lambda chains. The term "heavy chain" includes a full-length heavy chain and fragments thereof having sufficient variable region sequence to confer binding specificity. A full-length heavy chain includes a variable domain, VH, and three constant domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any class, including IgG (including IgG1, IgG2, IgG3 and IgG4 subclasses), IgA (including IgA1 and IgA2 subclasses), IgM, IgD and IgE. The term "variable region" or "variable domain" refers to a portion of the light and/or heavy chains of an antibody generally responsible for antigen recognition, typically including approximately the amino-terminal 120 to 130 amino acids in the heavy chain (VH) and about 100 to 110 amino terminal amino acids in the light chain (VL).

A "complementarity determining region" or "CDR" is an amino acid sequence that contributes to antigen-binding specificity and affinity. "Framework" regions (FR) can aid in maintaining the proper conformation of the CDRs to promote binding between the antigen-binding region and an antigen. Structurally, framework regions can be located in antibodies between CDRs. The variable regions typically exhibit the same general structure of relatively conserved framework regions (FR) joined by three hyper variable regions, CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), unless stated otherwise.

A "multispecific antibody construct" or "multispecific antibody" is one that targets or binds to more than one distinct antigen or epitope. A "bispecific," "dual-specific" or "bifunctional" antibody construct or antibody is a species of multispecific antibody construct that targets or binds to two different antigens or epitopes. In general, a bispecific antibody construct can have two different antigen-binding domains. The two antigen-binding domains of a bispecific antibody construct or antibody will bind to two different epitopes, which can reside on the same or different molecular targets. In one embodiment, the bispecific antibody construct is in a naturally occurring format. In other words, the bispecific antibody construct has the same format as a naturally occurring IgG, IgA, IgM, IgD, or IgE antibody.

Antibody heavy chains pair with antibody light chains and meet or contact one another at one or more "interfaces." An "interface" includes one or more "contact" amino acid residues in a first polypeptide that interact with one or more "contact" amino acid residues of a second polypeptide, or with one or more contact residues from additional polypeptides, where the first polypeptide, second polypeptide, or additional polypeptides meet or contact each other. For example, an interface exists between the VH and CH1 domains of a heavy chain, between the VL and CL domains of a light chain, between two CH3 domains of a dimerized Fc region, between the CH1 domain of the heavy chain and CL domain of the light chain, and between the VH domain of the heavy chain and the VL domain of the light chain. The "interface" can be derived from an IgG antibody and for example, from a human IgG1 antibody. Alternatively, an interface includes one or more contact amino acid residues from one portion of a polypeptide that interact with one or more contact residues from a different portion of the same polypeptide. For example, an interface exists between the variable domain and the constant domain of a light chain.

By "contact amino acid residues" is meant amino acid residues minimally comprising two residues that exhibit at least one type of non-covalent bonding (e.g. van der waals, hydrogen bonding etc.) to one another.

A Fab (also referred to as fragment antigen-binding) contains the constant domain (CL) of the light chain and the first constant domain (CH1) of the heavy chain along with the variable domains VL and VH on the light and heavy chains respectively. A heavy chain Fab sequence is a truncated heavy chain comprising VH and CH1 domains. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region. The term "Fab format" is meant to include antibody constructs such as Fabs and Fab' fragments. The light chain portions of constructs in the Fab format may include, but are not limited to kappa light chains, lambda light chains, or chimeric light chains, or combinations thereof. The heavy chain portions of constructs in the Fab format may include, but are not limited to heavy chains derived from IgG, IgM, IgA, IgE, or IgD classes.

A "single-chain Fv" or "scFv" includes the VH and VL domains of an antibody, wherein these domains are present in a single polypeptide chain. In one embodiment, the scFv polypeptide further comprises a polypeptide linker between the VH and VL domains which enables the scFv to form the desired structure for antigen-binding. For a review of scFvs see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

An antibody in "Mab format" refers to an antibody that has a structure similar to a naturally occurring antibody. In other words, antibodies in Mab format may have two full length heavy chains and two full length light chains. The light chains may include, but are not limited to, kappa light chains, lambda light chains, or chimeric light chains or combinations thereof. The heavy chain portions of constructs in the Mab format may include, but are not limited to heavy chains derived from IgG, IgM, IgA, IgE, or IgD classes. Antibodies in Mab format are bivalent and may be monospecific or bispecific.

The term "amino acid modifications" as used herein includes, but is not limited to, amino acid insertions, deletions, substitutions, chemical modifications, physical modifications, and rearrangements.

The amino acid residues for the immunoglobulin heavy and light chains may be numbered according to several conventions including Kabat (as described in Kabat and Wu, 1991; Kabat et al, Sequences of proteins of immunological interest. 5th Edition—US Department of Health and Human Services, NIH publication no. 91-3242, p 647 (1991)), IMGT (as set forth in Lefranc, M.-P., et al. IMGT®, the international ImMunoGeneTics information system® Nucl. Acids Res, 37, D1006-D1012 (2009), and Lefranc, M.-P., IMGT, the International ImMunoGeneTics Information System, Cold Spring Harb Protoc. 2011 Jun. 1; 2011(6)), 1JPT (as described in Katja Faelber, Daniel Kirchhofer, Leonard Presta, Robert F Kelley, Yves A Muller, The 1.85 A resolution crystal structures of tissue factor in complex with humanized Fab d3h44 and of free humanized Fab d3h44: revisiting the solvation of antigen combining sites1, Journal of Molecular Biology, Volume 313, Issue 1, Pages 83-97,) and EU (according to the EU index as in Kabat referring to the numbering of the EU antibody (Edelman et al., 1969, Proc Natl Acad Sci USA 63:78-85)). Kabat numbering is used herein for the VH, CH1, CL, and VL domains unless otherwise indicated. EU numbering is used herein for the CH3 and CH2 domains, and the hinge region unless otherwise indicated. The AHo numbering system (described in Honegger, A. and Pluckthun, A., Yet another numbering scheme for immunoglobulin variable domains: An automatic modeling and analysis tool, J. Mol. Biol, 309(2001) 657-670) and Chothia numbering system (Al-Lazikani B, Lesk A M, Chothia C, Standard conformations for the canonical structures of immunoglobulins J. Mol. Biol, 273 (1997) 927-948) may also be used to identify amino acid residues in the variable domains of the immunoglobulin heavy and light chains.

The identification of amino acid substitutions at specific amino acid residues or positions may be denoted and abbreviated in many formats, as is known in the art. For example, the use of underscore "_" or slash "/" may be used to separate the individual amino acid substitutions of a combination of amino acid substitutions. As an illustrative example, the combination of amino acid substitutions 83V, 85T, and 105E, may also be represented as 83V_85T_105E, or as 83V/85T/105E. These three types of formats are used interchangeably in this disclosure.

Chimeric Fabs and Stabilized Chimeric Fabs

Provided herein are stabilized chimeric Fabs comprising a modified Vlambda-Ckappa chimeric light chain construct and a heavy chain comprising a VH and a CH1 domain. The modified Vlambda-Ckappa chimeric light chain construct comprises a Vlambda sequence comprising one or one or more stabilizing amino acid modifications that increase the thermal stability of the chimeric Fab. The term "chimeric Fab" or "chimeric heterodimer" as used herein, refers to a Fab having a heavy chain comprising a CH1 domain sequence and a VH domain sequence, and a chimeric immunoglobulin light chain polypeptide (Vlambda-Ckappa chimeric light chain) construct, wherein the heavy chain sequence and the Vlambda-Ckappa chimeric light chain construct form a Fab region that binds to an epitope. A "heavy chain Fab sequence" refers to the fragment of an immunoglobulin heavy chain including the CH1 domain sequence and the VH domain sequence. A chimeric Fab is typically the starting point for engineering stabilized chimeric Fabs. Thus, stabilized chimeric Fabs are based on parent chimeric Fabs which have been engineered to include one or more stabilizing amino acid modifications that increase the thermal stability of the chimeric Fab.

In one embodiment, the parent chimeric Fab may comprise sequences derived from a parent antibody having a lambda light chain (a parent lambda antibody). In these embodiments, the parent chimeric Fab comprises a heavy chain Fab sequence from a parent lambda antibody as well as a Vlambda-Ckappa chimeric light chain construct having a Vlambda sequence from the parent lambda antibody and a Ckappa sequence from a kappa light chain. A parent chimeric Fab is also referred to as a wild-type chimeric heterodimer without the one or more stabilizing amino acid modifications.

Parent Lambda Antibodies

A number of lambda antibodies are known in the art, and are suitable as parent lambda antibodies, as long as they comprise a naturally occurring lambda light chain structure. "Naturally occurring light chain structure" as used herein means a light chain structure having lambda VL and CL domains. In one embodiment, the parent lambda antibody is a naturally occurring antibody. In another embodiment, the parent lambda antibody is an engineered lambda antibody. An engineered antibody is one that comprises one or more modifications that alter the polypeptide sequence or functional properties of the antibody. Functional properties that may be altered include, but are not limited to, antigen-binding, effector function, thermal stability, heavy chain pairing and/or light chain pairing in the context of bispecific antibodies. The parent lambda antibody may also be engineered to improve its pharmacokinetic/pharmacodynamic profile and decrease immunogenicity. These functional properties may be altered by one or more amino acid modifications in the polypeptide sequence of the parent antibody. Suitable methods of altering these functional properties are known in the art, some of which are described elsewhere herein.

In one embodiment, the parent lambda antibody is a mouse, human or humanized antibody. "Humanized" forms of non-human (e.g., rodent) antibodies are antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody can comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also can comprise at least a portion of an immunoglobulin constant region (Fc), typically that of a human immunoglobulin. For further details, see Jones et al., *Nature* 321:522-525 (1986); Riechmann et al., *Nature* 332:

323-329 (1988); and Presta, *Curr. Op. Struct. Biol.* 2:593-596 (1992). Thus, in some embodiments, the parent chimeric antibody comprises mouse, human, or humanized heavy chain Fab sequences, or Vlambda sequences.

In some embodiments, the parent chimeric Fab comprises a Vlambda-Ckappa chimeric light chain construct having a Vlambda sequence from a human or humanized lambda antibody, and a Ckappa sequence. The sequence of an exemplary Vlambda-Ckappa chimeric light chain construct is provided in FIG. 2, and aligned against the sequence of the lambda light chain of the parent antibody.

The interface between the mouse VL domain and CL domain of the mouse lambda light chain is very similar to the interface between the human VL domain and CL domain of the human lambda light chain, and the interface between the mouse VL domain and CL domain of the mouse kappa light chain is very similar to the interface between the human VL domain and CL domain of the human kappa light chain. Thus, it is contemplated that the stabilizing amino acid modifications described herein can also be applied to a parent chimeric Fab comprising a Vlambda-Ckappa chimeric light chain construct having a Vlambda sequence from a mouse parent lambda antibody, and a Ckappa sequence from a human kappa antibody. Thus, in one embodiment, the stabilized chimeric Fab comprises a chimeric Fab comprising a Vlambda-Ckappa chimeric light chain construct having a Vlambda sequence from a mouse lambda antibody, and a Ckappa sequence from a human kappa antibody.

The CL and VL domains of lambda antibodies comprise light chains belonging to different germlines. In one embodiment, the VL domain of the parent lambda antibody is selected from the human germline subgroups IGLV1, IGLV2, IGLV3, IGLV4, IGLV5, IGLV6, IGLV7, IGLV8, IGLV9, IGLV10 or IGLV11. In one embodiment, the VL domain of the parent lambda antibody is selected from the human germline subgroups IGLV1, IGLV2 or IGLV6.

Lambda antibodies may also comprise heavy chain domains belonging to different germlines. In one embodiment, the parent lambda antibody comprises a heavy chain with a VH domain selected from the human VH domain germline subgroups IGHV1, IGHV2, IGHV3, IGHV4, 1GHV5, IGHV6 or IGHV7. In one embodiment, the parent lambda antibody comprises a heavy chain with a VH domain from human VH domain germline subgroups IGHV1, IGHV3 or IGHV4. In one embodiment, the parent lambda antibody comprises a heavy chain with a VH domain from human VH domain germline subgroups IGHV3 or IGHV4. In another embodiment, the parent lambda antibody has a heavy chain with a J segment selected from the human J segment germline genes IGHJ1, IGHJ2, IGHJ3, IGHJ4, IGHJ5, or IGHJ6. In one embodiment, the parent lambda antibody has a heavy chain with a CH1 domain selected from the human CH1 domain germline subgroups IGHG1, IGHG2, IGHG3, or IGHG4. In one embodiment, the parent lambda antibody has a heavy chain with a human CH1 domain from germline subgroup IGHG1.

In one embodiment, the parent lambda antibody is a therapeutic antibody. Non-limiting examples of suitable therapeutic antibodies comprising a lambda light chain and the antigens they bind to are identified in Table A below:

TABLE A

Exemplary therapeutic antibodies comprising a lambda light chain

| Antibody | Antigens |
| --- | --- |
| avelumab | Programmed Cell Death 1 Ligand 1 |
| belimumab | B-cell activating factor |
| bimagrumab | activin receptor MB |

TABLE A-continued

Exemplary therapeutic antibodies comprising a lambda light chain

| Antibody | Antigens |
| --- | --- |
| briakinumab | Interleukin 12 |
| brontictuzumab | Notch1 |
| cixutumumab | Insulin-like Growth Factor 1 Receptor |
| drozitumab | Cytokine Death Receptor 5 |
| evolocumab | Proprotein Convertase Subtilisin/Kexin Type 9 |
| exbivirumab | Hepatitis B virus surface antigen |
| fezakinumab | Interleukin 22 |
| galiximab | CD80 |
| guselkumab | Interleukin 23 p19 |
| lexatumumab | Cytokine Death Receptor 5 |
| mapatumumab | TRAIL Receptor-1 |
| mavrilimumab | Granulocyte-macrophage colony-stimulating factor receptor subunit alpha |
| narnatumab | Ron Receptor |
| orticumab | Oxidized LDL |
| otelixizumab | CD3 T-Cell Co-Receptor |
| rafivirumab | Rabies virus glycoprotein |
| raxibacumab | Anthrax Protective antigen |
| seribantumab | Receptor tyrosine-protein kinase erbB-3 |
| tesidolumab | Complement component 5 |
| tezepelumab | Thymic Stromal Lymphopoietin |
| tralokinumab | Interleukin 13 |
| vantictumab | Frizzled receptor |

In one embodiment, the parent chimeric Fab comprises a heavy chain Fab sequence and a Vlambda sequence from one of the antibodies listed in Table A.

The amino acid sequences of the antibodies listed in Table A, and other suitable parent antibodies, therapeutic or otherwise, can be easily obtained from publications describing these antibodies, and/or databases such as TABS, PDB, GenBank™, all of which are accessible on the internet.

Examples of other suitable parent lambda antibodies are the CAT-2200 antibody, the H3 antibody, and the EP6b_B01 antibody. The sequences of these antibodies are known in the art and provided in Table 2. For example, the amino acid sequence of the CAT-2200 antibody (binding to IL-17) can be found in PDB entry 2VXS 9, the amino acid sequences of the H3 (binding to HER3) can be found in U.S. Pat. No. 8,329,873; and the amino acid sequences of EP6b_B01 (binding to Fas) can be found in PDB entry 3THM.

scFvs

As indicated above, in some embodiments, parent chimeric Fabs can be derived from scFvs. Parent chimeric Fabs derived from scFvs can often be generated as a result of screening scFv phage display libraries to identify binders of interest. Methods of converting scFvs to Fabs are known in the art and described, for example in Steinwand et al. (2014) in Mabs 6:204, and Zuberbuhler et al. (2009) in Protein Engineering, Design & Selection 22: 169-174. In one embodiment, the parent chimeric Fab may be constructed directly from the sequences of an scFv. In another embodiment, the parent chimeric Fab may be derived from a Fab that has been converted from an scFv.

Many suitable scFvs are known in the art, as described in Smirnov et al. (2011) Proc. Natl. Acad. Sci. USA. 108: 15954 (describing reactibodies), or in Niemi. et al, (2010) J. Mol. Recognit. 24: 209-219; Schneider et al. (2012) J. Mol. Biol. 415: 699-715; and Fenn (2013) Plos One 8: e61953-e61953, describing antibodies originally identified as scFvs. In one embodiment, a parental chimeric Fab can be prepared from a therapeutic scFv, for example from blinatumomab, efungumab, pexelizumab, solitomab, and others. Parental chimeric Fabs can be constructs based on the VL and VH sequences of the scFv, and fused to the CH1 and Ckappa domains of a kappa antibody. In these embodiments, the parent chimeric Fab comprises a Vlambda-Ckappa chimeric light chain construct having a Vlambda sequence from an scFv and a Ckappa sequence from a kappa light chain, while the heavy chain Fab sequence comprises a VH domain from the scFv and a CH1 domain. Suitable CH1 domain sequences can be selected from the human CH1 domains from IgG, IgD, IgE, IgM, or IgA classes. In one embodiment, the CH1 domain sequences are selected from the CH1 domain germline subgroups IGHG1, IGHG2, IGHG3, or IGHG4. Suitable Ckappa sequences are described below.

Ckappa Sequences

The polypeptide sequence of the Vlambda-Ckappa chimeric light chain construct can be generated by fusing the VL domain (Vlambda) sequence of the lambda light chain of the parent antibody with the sequence of a suitable Ckappa constant domain. Suitable Ckappa constant domain sequences are those selected from the CL germline alleles IGKC*01, IGKC*02, IGKC*03, IGKC*04, or IGKC*05. In one embodiment, the Ckappa constant domain sequence is from germline subgroup IGKC*01. The amino acid sequences of these Ckappa constant domains are readily available from the IMGT database noted above.

In some embodiments, the parent chimeric Fab may be a chimeric Fab known or described in the art. For example, the parent chimeric Fab may be the chimeric Fab described in Ponomarenko et al. (2014) in Act Crystallographica D70: 708-719.

In some embodiments, the parent chimeric Fab has a thermal stability that is the same as that of the Fab from the parent lambda antibody. In some embodiments, the parent chimeric Fab has a thermal stability that is at least 10° C. lower than that of the Fab from the parent lambda antibody. In some embodiments, the parent chimeric Fab has a thermal stability that is at least 5° C. lower than that of the Fab from the parent lambda antibody.

Stabilizing Amino Acid Modifications

The term "stabilized chimeric Fab" as used herein refers to a chimeric Fab or chimeric heterodimer wherein the Vlambda sequence of the Vlambda-Ckappa chimeric light chain construct comprises one or more stabilizing amino acid modifications that increase the thermal stability of the parent chimeric Fab. Thus, in one embodiment, a stabilized chimeric Fab comprises an immunoglobulin heavy chain polypeptide construct comprising a heavy chain constant domain 1 (CH1) sequence and a heavy chain variable domain (VH) sequence (heavy chain Fab sequence), and a Vlambda-Ckappa chimeric light chain construct comprising one or more stabilizing amino acid modifications in the Vlambda sequence that increase the thermal stability of the parent chimeric Fab, wherein the heavy chain Fab sequence and the Vlambda-Ckappa chimeric light chain construct form a Fab region that binds to an epitope. Stabilized chimeric Fabs are engineered from parent chimeric Fabs and are essentially parent chimeric Fabs comprising one or more stabilizing amino acid modifications described herein.

The term "thermal stability" is a property often assessed for antibodies by measuring the Tm or melting temperature of an Fab region, either isolated or in an antibody construct. The thermal stability of Fabs can be measured using a number of known methods as described elsewhere herein.

The stabilizing amino acid modifications described here have been identified by examining the structures of naturally occurring light chains in the Fab format (i.e. paired with a heavy chain fragment having VH and CH1 domains) and comparing these structures to those of Vlambda-Ckappa chimeric Fabs. Comparison of these structures led to the identification of amino acid residues in the variable lambda domain that can be modified to mimic the interface observed between Vkappa-Ckappa domains resulting in improved compatibility of the Vlambda-Ckappa interface in stabilized chimeric Fabs.

In one embodiment, the stabilized chimeric Fab comprises stabilizing amino acid modifications in the Vlambda sequence at amino acid residues in the interface between the Vlambda and Ckappa domains of the Vlambda-Ckappa chimeric light chain construct. The positions at which stabilizing amino acid modifications occur are identified according to the Kabat numbering system, unless otherwise indicated.

In one embodiment, the stabilized chimeric Fab comprises one or more stabilizing amino acid modifications in the Vlambda sequence of the Vlambda-Ckappa chimeric light chain construct. In one embodiment, the stabilized chimeric Fab comprises two or more stabilizing amino acid modifications in the Vlambda sequence of the Vlambda-Ckappa chimeric light chain construct. In one embodiment, the stabilized chimeric Fab comprises three or more stabilizing amino acid modifications in the Vlambda sequence of the Vlambda-Ckappa chimeric light chain construct. In one embodiment, the stabilized chimeric Fab comprises four or more stabilizing amino acid modifications in the Vlambda sequence of the Vlambda-Ckappa chimeric light chain construct.

Stabilizing amino acid modifications may be at the interface between the Vlambda and Ckappa domains of the Vlambda-Ckappa chimeric Fab light chain. In one embodiment, the stabilizing amino acid modifications may be at an amino acid residue that is not considered to be at the interface of the Vlambda and Ckappa domains of the Vlambda-Ckappa chimeric light chain construct.

In some embodiments, the stabilized chimeric Fab comprises one or more stabilizing amino acid modifications at the interface between the Vlambda and Ckappa domains of the Vlambda-Ckappa chimeric light chain construct. Non-limiting examples of such amino acid residues are found at positions 80, 83, 105, and 106 of the Vlambda sequence. In one embodiment, the stabilized chimeric Fab comprises a stabilizing amino acid modification in the Vlambda sequence at residue 83. In one embodiment, the stabilized chimeric Fab comprises a stabilizing amino acid modification in the Vlambda sequence at residue 105. In one embodiment, the stabilized chimeric Fab comprises a stabilizing amino acid modification in the Vlambda sequence at residue 106. In one embodiment, the stabilized chimeric Fab comprises a stabilizing amino acid modification in the Vlambda sequence at residue 80.

The stabilized chimeric Fab may comprise a stabilizing amino acid modification in the Vlambda sequence at an amino acid residue that is not at the interface. In one embodiment, the stabilized chimeric Fab comprises a stabilizing amino acid modification at residue 85 in the Vlambda sequence.

In some embodiments, the stabilized chimeric Fab may include a combination of stabilizing amino acid modifications in the Vlambda sequence at two amino acid residues. In some embodiments, the stabilized chimeric Fab may include a combination of stabilizing amino acid modifications at residues 83 and 85; 83 and 106; 105 and 106; 105 and 106A; 83 and 105; 85 and 105; or 85 and 106. In one embodiment, the stabilized chimeric Fab may comprise a combination of stabilizing amino acid modifications at residues 83 and 85; at residues 83 and 106; at residues 105 and 106A; or at residues 83 and 105.

In other embodiments, the stabilized chimeric Fabs may include a combination of stabilizing amino acid modifications in the Vlambda sequence at three amino acid residues. In certain embodiments, the stabilized chimeric Fab may include a combination of stabilizing amino acid modifications at residues 83, 85, and 105; at residues 83, 105, and 106A; at residues 83, 85, and 106; at residues 83, 105, and 106; or at residues 85, 105, and 106. In some embodiments, the stabilized chimeric Fab may include a combination of stabilizing amino acid modifications at residues 83, 85, and 105, or at residues 83, 105, and 106A.

In other embodiments, the stabilized chimeric Fabs may include a combination of stabilizing amino acid modifications in the Vlambda sequence at four or more amino acid residues. Thus, in some embodiments, the stabilized chimeric Fab may include a combination of stabilizing amino acid modifications at residues 83, 85, 105, and 106; at residues 80, 83, 105, and 106A; at residues 80, 83, 85 and 105; at residues 80, 83, 85 and 105; at residues 80, 85, 105 and 106; at residues 80, 83, 105 and 106; or at residues 83, 105, 106, and 106A.

In yet other embodiments, the stabilized chimeric Fabs may include a combination of stabilizing amino acid modifications in the Vlambda sequence at residues 80, 83, 85, 105, and 106A; at residues 80, 83, 105, 106 and 106A; at residues 83, 85, 105, 106 and 106A; at residues 80, 83, 85, 105, 106; or at residues 80, 83, 85, 105, 106 and 106A.

As indicated above, the amino acid positions at which stabilizing amino acid modifications occur are described herein according to the Kabat numbering system. However, these amino acid positions can also be identified according to alternative numbering systems. For example, the following table identifies selected specific amino acid positions in the Vlambda domain according to Kabat, IMGT, AHo, and EU numbering systems.

TABLE A1

Selected Vlambda domain amino acids numbered according to Kabat, IMGT, AHo, and Chothia numbering systems Numbering system

| Kabat | IMGT | AHo | Chothia |
|-------|------|-----|---------|
| 80    | 96   | 98  | 80      |
| 83    | 99   | 101 | 83      |
| 85    | 101  | 103 | 85      |
| 105   | 125  | 146 | 105     |
| 106   | 126  | 147 | 106     |
| 106A  | 127  | 148 | 106A    |

Amino Acid Substitutions

Amino acid residues can be grouped according to properties of their side chains, such as hydrophobicity, polarity, side chain volume and/or size. Examples of hydrophobic amino acid residues include leucine, isoleucine, valine, methionine, proline, alanine, phenylalanine, cysteine and tryptophan. Examples of polar non-charged amino acid residues include glutamine, asparagine, serine, threonine, histidine and tyrosine. Examples of negatively charged amino acid residues include glutamic acid and aspartic acid. Examples of positively charged amino acid residues include lysine and arginine. The side chain volumes of amino acid residues have been measured and are known in the art as shown in Table 1 of U.S. Pat. No. 5,821,333, reproduced in Table B below:

TABLE B

Properties of amino acid residues
Properties of Amino Acid Residues

| Amino Acid | One-Letter Abbreviation | MASS[a] (daltons) | VOLUME[b] (Angstrom$^3$) | Accessible Surface Area[c] (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 11.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from Handbook of Chemistry and Physics, 43rd ed. Cleveland, Chemical Rubber Publishing Co., 1961.
[b]Values from A. A. Zamyatnin, Prog. Biophys. Mol. Biol. 24: 107-123, 1972.
[c]Values from C. Chothia, J. Mol. Biol. 105: 1-14, 1975. The accessible surface area is defined in FIGS. 6-20 of this reference.

The stabilized chimeric Fabs may comprise stabilizing amino acid modifications at each residue as described below. In one embodiment, the amino acid at position 83 of the stabilized chimeric Fab comprises substitution with a hydrophobic amino acid. In some embodiments, the amino acid at position 83 of the stabilized chimeric Fab comprises substitution with a hydrophobic amino acid selected from F, L, I, V, or A. In some embodiments, the amino acid at position 83 of the stabilized chimeric Fab comprises substitution with a hydrophobic amino acid selected from F, I, V, or A. In one embodiment, the amino acid at position 83 of the stabilized chimeric Fab comprises substitution with a polar non-charged amino acid. Based on structural assessment of the immediate surrounding environment for position 83, additional amino acid substitutions at this position are contemplated that could be compatible in this position and would provide contacts across the relatively non-rigid variable and constant domain interface in the chimeric light chain, and thus improve thermostability. These additional amino acids include polar non-charged amino acids of suitable size and geometry, such as S, N, H, Q or T. Thus, in some embodiments, the amino acid at position 83 of the stabilized chimeric Fab comprises substitution with a polar non-charged amino acid selected from S, T, H, N or Q. In other embodiments, the stabilized chimeric Fab comprises the polar non-charged amino acid substitution 83S, 83N, 83H or 83Q. In one embodiment, the stabilized chimeric Fab comprises the amino acid substitution 83A, 83F, 83I, 83V, 83L or 83T.

In one embodiment, the amino acid at position 85 of the stabilized chimeric Fab comprises substitution with a hydrophobic amino acid. In one embodiment, the amino acid at position 85 of the stabilized chimeric Fab comprises substitution with a hydrophobic amino acid selected from 85V or 85A. In one embodiment, the amino acid at position 85 of the stabilized chimeric Fab comprises substitution with a hydrophobic amino acid selected from 85V. Structural assessment of the suitability of additional amino acid substitutions, in the context of the immediate surrounding environment of position 85 indicated that polar non-charged amino acids of suitable size and geometry, such as T, S, H, N, Q and Y, could indirectly contribute to the overall compatibility of the interface between variable and constant domain in the chimeric light chain, and thus be expected to contribute to the improvement in thermostability. Thus, in one embodiment, the amino acid at position 85 of the stabilized chimeric Fab may be substituted with a polar non-charged amino acid. In one embodiment, the stabilized chimeric Fab comprises amino acid substitution 85T, 85S, 85H, 85N, 85Q, or 85Y. In other embodiments, the stabilized chimeric Fab comprises substitution with a polar non-charged amino acid selected from 85S, 85H, or 85Q. In one embodiment, the stabilized chimeric Fab comprises amino acid substitution 85T, 85V, 85N, 85A, or 85Y.

In one embodiment, the amino acid at position 105 of the stabilized chimeric Fab comprises substitution with an amino acid that is negatively charged. In one embodiment, the amino acid at position 105 of the stabilized chimeric Fab comprises the negatively charged amino acid substitution 105E or 105D. The structural assessment of the suitability of additional amino acid substitutions than E in this position, in the context of immediate surrounding environment indicated that polar non-charged amino acids such as N or Q, could provide similar interactions across the variable and constant domain interface in the chimeric light chain as those of 105E and thus could also contribute to improved thermostability. Thus, in one embodiment, the amino acid at position 105 of the stabilized chimeric Fab comprises substitution with a polar non-charged amino acid. In one embodiment, the amino acid at position 105 of the stabilized chimeric Fab comprises the polar non-charged amino acid substitution 105N or 105Q.

In some embodiments, the amino acid at position 106 of the stabilized chimeric Fab comprises substitution with a hydrophobic amino acid. In one embodiment, the hydrophobic amino acid substitution at position 106 of the stabilized chimeric Fab is selected from 106I, 106L, or 106M. In one embodiment, the hydrophobic amino acid substitution at position 106 of the stabilized chimeric Fab is 106I.

In some embodiments, residue 80 of the stabilized chimeric Fab comprises substitution with an amino acid that is hydrophobic. In certain embodiments, the stabilized chimeric Fab comprises a hydrophobic amino acid substitution selected from 80A, 80P, or 80V. In certain embodiments, the stabilized chimeric Fab comprises a hydrophobic amino acid substitution selected from 80A or 80P. Based on the structural assessment of the suitability of other amino acid substitutions in this position, in the context of immediate surrounding environment, polar non-charged amino acids such as S, N or Q could lead to similar interactions at the variable and constant domain interface in the chimeric light chain as those of 80A and 80P, and thus be expected to have a similar minor contribution to improved thermostability. Thus, in some embodiments, residue 80 of the stabilized chimeric Fab comprises substitution with an amino acid that is polar and non-charged. In certain embodiments, the stabilized chimeric Fab comprises a polar non-charged amino acid substitution selected from 80S, 80N, or 80Q.

One of skill in the art would understand that multiple combinations of the amino acid positions and substitutions described herein can be used to increase the stability of chimeric Fabs compared to the parent chimeric Fab. A representative number of such combinations has been described and tested in the examples, but the disclosure is not limited to these alone. For example, it is contemplated that for the combination of amino acid positions described in this disclosure, the amino acid substitutions described for each position may be employed, and each combination of position(s) and substitutions is herein described.

Thus, in additional embodiments, the stabilized chimeric Fab comprises an amino acid substitution or combination of amino acid substitutions selected from those described in Table 3. In other embodiments, the stabilized chimeric Fab comprises the amino acid substitutions 83L and 85T; 83L and 85V; 83L and 105E; 83L and 106I; 83L, 85V and 105E; 83L, 85T and 105E; 83L, 85T, 105E and 106I; or 83L, 85V, 105E and 106I . In still other embodiments, the stabilized chimeric Fab comprises the amino acid substitutions 83S and 85T; 83S and 85V; 83S and 105E; 83S and 106I; 83S, 85V and 105E; 83S, 85T and 105E; 83S, 85T, 105E and 106I; or 83S, 85V, 105E and 106I. In some embodiments, the stabilized chimeric Fab comprises the amino acid substitutions 83T and 85T; 83T and 85V; 83T and 105E; 83T and 106I; 83T, 85V and 105E; 83T, 85T and 105E; 83T, 85T, 105E and 106I; or 83T, 85V, 105E and 106I. In additional embodiments, the stabilized chimeric Fab comprises the amino acid substitutions 83A and 85S; 83A, 85S and 105E; 83A, 85S, 105E and 106I; 83I and 85S; 83I, 85S and 105E; 83I, 85S, 105E and 106I; 83V and 85S; 83V, 85S and 105E; 83V, 85S, 105E and 106I; 83F and 85S; 83F, 85S and 105E; or 83F, 85S, 105E and 106I. In further embodiments, the stabilized chimeric Fab comprises the amino acid substitutions 83A and 105D; 83A, 85T and 105D; 83A, 85V and 105D; 83I and 105D; 83I, 85T and 105D; 83I, 85V and 105D; 83V and 105D; 83V, 85T and 105D; 83V, 85V and 105D; 83F and 105D; 83F, 85T and 105D; or 83F, 85V and 105.

In some embodiments, the stabilized chimeric Fab comprises the amino acid substitutions 83F and 85V; 83V and 85V; 83I and 85V; 83A and 85V; 85T and 105E; 85V and 105E; 83F and 85T; 85V and 105E; 83V and 85T; 85V and 105E; 83I and 85T; 85V and 105E; 83A and 85T; or 85V and 105E.

Increased Stability

The thermal stability of the stabilized chimeric Fab is compared to that of the parent chimeric Fab to determine the increase in stability exhibited by the stabilized chimeric Fab relative to the parent chimeric Fab. In one embodiment, thermal stability is measured by differential scanning calorimetry (DSC). In another embodiment, thermal stability is measured by differential scanning fluorimetry (DSF). In some embodiments, the stabilized chimeric Fab may exhibit an increase in thermal stability of greater than 15° C. relative to the parent chimeric Fab. In some embodiments, stabilized chimeric Fabs comprising one or more stabilizing amino acid modifications may exhibit an increase in thermal stability of about 15° C. relative to the parent chimeric Fab. In some embodiments, stabilized chimeric Fabs comprising one or more stabilizing amino acid modifications may exhibit an increase in thermal stability of about 10° C. relative to the parent chimeric Fab. In some embodiments, stabilized chimeric Fabs comprising one or more stabilizing amino acid modifications may exhibit an increase in thermal stability of about 9, 8, 7, 6, 5, 4, 3, 2, or 1° C. relative to the parent chimeric Fab.

In some embodiments, stabilized chimeric Fabs comprising one or more stabilizing amino acid modifications may exhibit an increase in thermal stability of about 10, 9, 8, 7, 6, 5, 4, 3, 2, or 1° C. relative to the Fab of the parent lambda antibody. In some embodiments, stabilized chimeric Fabs comprising one or more stabilizing amino acid modifications may exhibit an increase in thermal stability of about 10, 9, 8, 7, 6, 5, 4, 3, 2, or 1° C. relative to the Fab of the parent lambda antibody, as measured by differential scanning calorimetry. In some embodiments, stabilized chimeric Fabs comprising one or more stabilizing amino acid modifications may exhibit an increase in thermal stability of about 10, 9, 8, 7, 6, 5, 4, 3, 2, or 1° C. relative to the Fab of the parent lambda antibody, as measured by differential scanning fluorimetry.

Effect on Antigen-Binding

A stabilized chimeric Fab comprising one or more stabilizing amino acid modifications is able to bind to the epitope on the target antigen with an affinity that is similar to that of the parent chimeric antibody, or that of the parent lambda antibody. Thus, in one embodiment, the stabilized chimeric Fab is able to bind to the epitope on the target antigen with an affinity that is within about 10-fold that of the parent lambda antibody. In other embodiments, the stabilized chimeric Fab is able to bind to the epitope on the target antigen with an affinity that is within about 5-fold that of the parent lambda antibody. In still other embodiments, the stabilized chimeric Fab is able to bind to the epitope on the target antigen with an affinity that is within about 2.5-fold that of the parent lambda antibody. In one embodiment, the affinity of the stabilized chimeric Fab is measured using surface plasmon resonance (SPR) as described elsewhere herein.

Transferability

The stabilizing amino acid modifications can be engineered into parental chimeric Fabs other than those specifically described in the Examples. Because the majority of the amino acid residues at the interface between the variable and constant domains in the lambda light chain are highly conserved, the effect of the stabilizing amino acid modifications described here is expected to be transferable, in general to most parental chimeric Fab and Mab systems. Thus, the stabilizing amino acid modifications can increase the stability of chimeric Fabs comprising a Vlambda-Ckappa chimeric light chain, in general.

Additional Optional Modifications

In some embodiments, the stabilized chimeric Fabs described herein can be further modified (i.e., by the covalent attachment of various types of molecules) such that covalent attachment does not interfere with the ability of the stabilized chimeric Fab to bind to the epitope of the target antigen. Such modifications include, for example, but not by way of limitation, glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc.

In one embodiment, the stabilized chimeric Fabs comprise one or more modification that can potentially decrease the immunogenicity of the Fab. In one embodiment, the stabilized chimeric Fab comprises amino acid modification at residue 106A, according to Kabat. In one embodiment, the stabilized chimeric Fab comprises the amino acid substitution 106AK.

In other embodiments, the stabilized chimeric Fabs described herein can be conjugated (directly or indirectly) to a therapeutic agent or drug moiety that modifies a given biological response. In certain embodiments, a stabilized chimeric Fab is conjugated to a drug, e.g., a toxin, a chemotherapeutic agent, an immune modulator, or a radioisotope. Several methods of preparing ADCs (antibody-drug conjugates or antibody construct drug conjugates) are known in the art and are described in U.S. Pat. No. 8,624,003 (pot method), 8,163,888 (one-step), and 5,208,020 (two-step method) for example. In some embodiments, the drug is selected from a maytansine, auristatin, calicheamicin, or derivative thereof. In other embodiments, the drug is a maytansine selected from DM1 and DM4.

In some embodiments, the stabilized chimeric Fab is conjugated to a cytotoxic agent. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32, and Lu177), chemotherapeutic agents, and toxins such as small molecule toxins or enzymatically active toxins of bacterial, fungal, plant or animal origin, including fragments and/or variants thereof.

Therapeutic agents or drug moieties are not to be construed as limited to classical chemical therapeutic agents. For example, the drug moiety can be a protein or polypeptide possessing a desired biological activity. Such proteins can include, for example, a toxin such as abrin, ricin A, Onconase (or another cytotoxic RNase), pseudomonas exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, in an alternate embodiment, the stabilized chimeric Fab can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

In some embodiments, the immunoglobulin heavy and light chains of the stabilized chimeric Fab are expressed as fusion proteins comprising a tag to facilitate purification and/or testing etc. As referred to herein, a "tag" is any added series of amino acids which are provided in a protein at either the C-terminus, the N-terminus, or internally that contributes to the identification or purification of the protein. Suitable tags include but are not limited to tags known to those skilled in the art to be useful in purification and/or testing such as albumin binding domain (ABD), His tag, FLAG tag, glutathione-s-transferase, hemagglutinin (HA) and maltose binding protein. Such tagged proteins can also be engineered to comprise a cleavage site, such as a thrombin, enterokinase or factor X cleavage site, for ease of removal of the tag before, during or after purification.

Molecular Formats

The stabilized chimeric Fabs are useful as Fabs, and may also be incorporated into other molecular formats, or antibody constructs. Suitable molecular formats include the following non-limiting examples: stabilized chimeric Fabs linked with or without linkers to polypeptides such as albumin or fragments thereof, effector peptides, toxins, extracellular proteins, ligand-binding domains of cytokines, and the like. Exemplary, non-limiting antibody constructs may be designed by fusing the stabilized chimeric Fabs to other polypeptides such as Fabs, chimeric or otherwise, scFvs, domain antibodies, or naturally occurring antibodies. The heavy chain Fab sequence and/or the Vlambda-Ckappa chimeric light chain construct of the stabilized chimeric Fabs may be linked with or without linkers to other polypeptides. The stabilized chimeric Fabs may be fused to these other polypeptides at their N- or C-termini. The stabilized chimeric Fab may also be engineered as a single chain Fab. Such single chain Fabs are described in International Patent Publication No. WO 2014/018572, U.S. Patent Publication Nos. 2011/0293613 and 2010/0322935A1.

In some embodiments, the stabilized chimeric Fab can be linked directly or indirectly to a scaffold. Thus, in one embodiment, an antibody construct comprises at least one stabilized chimeric Fab, linked to a scaffold. Suitable scaffolds and modifications of same are known in the art and exemplary scaffolds and modifications of same are described below.

Scaffolds

The stabilized chimeric Fab can be linked to a scaffold, for example a peptide, polypeptide, polymer, nanoparticle or other chemical entity. The heavy chain Fab sequence or the Vlambda-Ckappa chimeric light chain construct of the stabilized chimeric Fab may be linked to a scaffold by either their N- or C-termini. In one embodiment, the scaffold is an albumin polypeptide, or split albumin polypeptide. Examples of suitable split albumin polypeptides are described in International Patent Publication Nos. WO 2012/116453 and WO 2014/012082.

In another embodiment, the stabilized chimeric Fab can be linked to a scaffold that is an immunoglobulin Fc (Fc), or portion thereof. In some embodiments, the Fc comprises at least one or two CH3 domain sequences. In some embodiments, the Fc further comprises at least one or two CH2 domain sequences. In some embodiments, the stabilized chimeric Fab is coupled, with or without one or more linkers, to the Fc. In some embodiments, the Fc is a human Fc. In some embodiments, the Fc is a human IgG or IgG1 Fc. In some embodiments, the Fc is a heterodimeric Fc. In some embodiments, an Fc is a single polypeptide. In some embodiments, an Fc is multiple peptides, e.g., two polypeptides.

In some embodiments, the Fc comprises one or more amino acid modifications in at least one of the CH3 domain sequences. Amino acid modifications can be made to the immunoglobulin Fc in order to drive preferential pairing between heterodimeric CH3 domain sequences relative to homodimeric CH3 domain sequences. These amino acid modifications are also referred to herein as heavy chain pairing designs. Such amino acid modifications are known in the art and include, for example, those described in US Patent Publication No. 2012/0149876. Alternate strategies for driving preferential pairing between heterodimeric CH3 domain sequences relative to homodimeric CH3 sequences including, for example, "knobs into holes," charged residues with ionic interactions, and strand-exchange engineered domain (SEED) technologies can also be employed. The latter strategies have been described in the art and are reviewed in Klein et al. supra. Further discussion of Fc domains follows below.

In some aspects, Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

In some aspects, the antibody construct comprises a stabilized chimeric Fab linked with or without a linker to a heterodimeric Fc comprising a modified CH3 domain that has been asymmetrically modified. The heterodimeric Fc can comprise two heavy chain constant domain polypeptides: a first heavy chain polypeptide and a second heavy chain polypeptide, which can be used interchangeably provided that Fc comprises one first heavy chain polypeptide and one second heavy chain polypeptide. Generally, the first heavy chain polypeptide comprises a first CH3 sequence and the second heavy chain polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table X provides the amino acid sequence of the human IgG1 Fc sequence, corresponding to amino acids 231 to 447 of the full-length human IgG1 heavy chain. The CH3 sequence comprises amino acid 341-447 of the full-length human IgG1 heavy chain.

Typically, an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table X. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE X

| | |
|---|---|
| Human IgG1 Fc sequence 231-447 (EU-numbering, SEQ ID NO: 29 | APELLGGPSVFLFPPKPKDTLMISRT PEVTCVVVDVSHEDPEVKFNWYVDGV EVHNAKTKPREEQYNSTYRWSVLTVL HQDWLNGKEYKCKVSNKALPAPIEKT ISKAKGQPREPQVYTLPPSRDELTKN QVSLTCLVKGFYPSDIAVEWESNGQP ENNYKTTPPVLDSDGSFFLYSKLTVD KSRWQQGNVFSCSVMHEALHNHYTQK SLSLSPGK |

TABLE X -continued

| Variant IgG1 Fc sequence (231-447) | Chain | Mutations |
|---|---|---|
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

In some embodiments, the Fc can comprise one or more amino acid modifications in at least one of the CH2 domain sequences. A number of mutations in the heavy chain sequence of the Fc are known in the art for selectively altering the affinity of the antibody Fc for different Fcgamma receptors. In some embodiments, the Fc comprises one or more modifications to alter binding of Fc-gamma receptors to the antibody construct.

The CH2 domain corresponds to amino acids 231-340 of the sequence shown in Table X. Exemplary, non-limiting amino acid modifications that alter the ability of the Fc of the antibody construct to bind to Fc-gamma receptors are listed below: S298A/E333A/K334A, S298A/E333A/K334A/K326A (Lu Y. Vernes J M, Chiang N, et al. J immunol Methods. 2011 Feb. 28; 365(1-2):132-41); F243L/R292P/Y300L/V305I/P396L, F243L/R292P/Y300L/L235V/P396L (Stavenhagen J B, Gorlatov S. Tuaillon N, et al. Cancer Res. 2007 Sep. 15; 67(18):8882-90; Nordstrom J L, Gorlatov S, Zhang W, et al. Breast. Cancer Res. 2011 Nov. 30:13(6): R123); F243L: (Stewart R, Thom G, Levens M, et al. Protein Eng Des Sel. 2011 September; 24(9):671-8), S298A/E333A/K334A (Shields R L, Namenuk A K, Hong K, et al. J Biol Chem. 2001 Mar. 2; 276(9):6591-604); S239D/I332E/A330L, S239D/I332E (Lazar G A, Dang W, Karki S, et al. Proc Natl Acad Sci USA. 2006 Mar. 14; 103(11): 4005-10); S239D/S267E, S267E/L328F (Chu S Y, Vostiar I, Karki S. et al. Mol Immunol. 2008 September; 45(15):3926-33): S239D/D265S/S298A/I332E, S239E/S298A/K326A/A327H, G237F/S298A/A330L/I332E, S239D/I332E/S298A, S239D/K326E/A330L/I332E/S298A, G236A/S239D/D270L/I332 E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) describes additional modifications to the Fc that affect binding of the Fc to Fc-gamma receptors on page 283.

In one embodiment, an antibody construct comprises a stabilized chimeric Fab and a dimeric Fc wherein the dimeric Fc comprises the amino acid modifications L234A, L235A, and D265S.

Additional Modifications to Improve Effector Function.

In some embodiments, the Fc of an antibody construct comprising a stabilized Fab described herein can be modified to improve its effector function. Such modifications are known in the art and include afucosylation, or engineering of the affinity of the Fc portion of antibodies towards an activating receptor, mainly FCGR3a for ADCC, and towards C1q for CDC. The following Table Y summarizes various designs reported in the literature for effector function engineering.

TABLE Y

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Thus, in one embodiment, an antibody construct comprises a stabilized chimeric Fab and a dimeric Fc that comprises one or more amino acid modifications as noted in the above table that confer improved effector function. In another embodiment, the antibody construct can be afucosylated to improve effector function.

FcRn Binding and PK Parameters

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport. Thus, in one embodiment, the Fc comprises one or more amino acid modifications that alter or promote the ability of the Fc to bind FcRn. Antibody constructs comprising a stabilized chimeric Fab and an Fc, can bind to FcRn.

Linkers

Stabilized chimeric Fabs can be operatively coupled to a scaffold as described herein. For example, antibody constructs comprising a stabilized chimeric Fab can be operatively coupled to an Fc as described herein. One of skill in the art would understand that multiple configurations and methods for coupling antibody constructs comprising a stabilized chimeric Fab are possible, all of which fall within the scope of the disclosure. In some aspects, the Fc is coupled to the stabilized chimeric Fab with or without one or more linkers. In some aspects, the Fc is directly coupled to the stabilized chimeric Fab. In some aspects, the Fc is coupled to the stabilized chimeric Fab by one or more linkers. In some aspects, Fc is coupled to the heavy chain of the stabilized chimeric Fab by a linker. In some aspects, the Fc is coupled to the chimeric light chain of the stabilized chimeric Fab by a linker.

In some aspects, the one or more linkers are one or more polypeptide linkers. In some aspects, the one or more linkers comprise one or more antibody hinge regions. In some aspects, the one or more linkers comprise one or more IgG1 hinge regions.

In some embodiments, the stabilized chimeric Fab can be incorporated into an antibody construct that is a monovalent antibody construct, i.e. has only one antigen-binding domain. These monovalent antibody constructs may comprise a stabilized chimeric Fab, and a scaffold. In one embodiment, the scaffold is an Fc region.

In other embodiments, the stabilized chimeric Fab can be incorporated into an antibody construct that is a multispecific antibody construct. In certain embodiments, the stabilized chimeric Fab can be incorporated into an antibody construct that is a bispecific antibody construct. In one embodiment, a bispecific antibody construct can comprise a stabilized chimeric Fab, and a second Fab, the second Fab comprising an immunoglobulin light chain construct and an immunoglobulin heavy chain construct. In certain embodiments, the second Fab is also a stabilized chimeric Fab.

In the context of bispecific antibody constructs comprising a stabilized chimeric Fab, a second Fab, and an Fc scaffold, additional amino acid modifications can be engineered into the bispecific antibody construct in order to facilitate the preparation of the bispecific antibody construct. For example, heavy chain pairing designs and/or light chain pairing designs can be engineered into the bispecific antibody construct in order to promote pairing of the heavy and light chains to form the desired bispecific antibody. Examples of heavy chain pairing designs are described elsewhere herein. Examples of light chain pairing designs are known in the art and described, for example, in International Patent Publication Nos. WO 2014/082179. WO 2015/181805, and WO 2017/059551.

Methods of Preparing Stabilized Chimeric Fabs

As described above, the stabilized chimeric Fabs described herein comprise a heavy chain comprising a CH1 domain sequence and a VH domain sequence (heavy chain Fab sequence), and a chimeric immunoglobulin light chain polypeptide (Vlambda-Ckappa chimeric light chain) construct, wherein the heavy chain Fab sequence and the Vlambda-Ckappa chimeric light chain construct form a Fab region that binds to an epitope on a target antigen. The Vlambda sequence of the Vlambda-Ckappa chimeric light chain construct comprises one or more stabilizing amino acid modifications that increase the thermal stability of the stabilized chimeric Fab relative to the parent chimeric Fab.

Accordingly, there are typically two polypeptide sequences that make up the stabilized chimeric Fab: a heavy chain Fab sequence and a Vlambda-Ckappa chimeric light chain construct. In some embodiments, antibody constructs comprising stabilized chimeric Fabs can be prepared as monospecific bivalent antibodies, or as bispecific antibodies. In these embodiments, there are typically four distinct polypeptide sequences, two immunoglobulin heavy chain polypeptide sequences (including sequences that make up the Fc region) or fragments thereof and two immunoglobulin light chain polypeptide sequences, at least one of which is a Vlambda-Ckappa chimeric light chain construct. All of these polypeptide sequences are referred to as immunoglobulin heavy and light chain polypeptides and can readily be prepared using recombinant DNA technology as known in the art. Standard techniques such as, for example, those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Short Protocols in Molecular Biology (Ausubel et al., John Wiley and Sons, New York, 4th ed., 1999); and Glick and Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression.

The polynucleotide and amino acid sequences of the immunoglobulin heavy and light chains of the parent lambda antibodies or kappa light chain sequences that make up the stabilized chimeric Fab are either known in the art or can be readily determined using nucleic acid and/or protein sequencing methods.

Accordingly, also provided are polynucleotides or a set of polynucleotides encoding the heavy chain Fab sequence and Vlambda-Ckappa chimeric Fab light chain construct of the stabilized chimeric Fab. In one embodiment, there is provided a polynucleotide that encodes the Vlambda-Ckappa chimeric light chain construct of the stabilized chimeric Fab. Such polynucleotides include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The polynucleotides include full-length genes or cDNA molecules as well as a combination of fragments thereof.

The polynucleotides encoding the engineered immunoglobulin heavy and light chain polypeptides described herein can be prepared by site specific mutagenesis of nucleotides in the DNA encoding the polypeptide, using cassette or PCR mutagenesis or other techniques well known in the art, to produce DNA encoding the engineered immunoglobulin heavy and light chain polypeptides, and thereafter expressing the recombinant DNA in cell culture as outlined herein. However, polynucleotides encoding the engineered immunoglobulin heavy and light chain polypeptides may also be prepared by in vitro gene synthesis using established techniques.

As will be appreciated by those in the art, due to the degeneracy of the genetic code, an extremely large number of polynucleotides may be made, all of which encode the engineered immunoglobulin heavy and light chain polypeptides described herein. Thus, having identified a particular amino acid sequence, those skilled in the art could make any number of different polynucleotides, by simply modifying the sequence of one or more codons in a way which does not change the amino acid sequence of the encoded protein.

Also provided are expression systems and constructs in the form of plasmids, expression vectors, transcription or expression cassettes which comprise at least one polynucleotide as above. Also provided are host cells comprising such expression systems or constructs.

Typically, expression vectors used in the host cells will contain sequences for plasmid maintenance and for cloning and expression of exogenous nucleotide sequences. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the polynucleotide encoding the polypeptide to be expressed, and a selectable marker element. The vector can be multicistronic i.e. expressing two or more of the polynucleotides encoding the immunoglobulin heavy and light chains of the stabilized chimeric Fab, or the stabilized chimeric Fab can be expressed by a set of vectors, each vector expressing one or more of the polynucleotides. The antibody construct can also be expressed using a set of vectors comprising a combination of multicistronic vectors and vectors that comprise a single polynucleotide encoding one of the immunoglobulin heavy and light chains.

In some embodiments, the vector may contain a "tag"-encoding sequence, i.e., an oligonucleotide molecule located at the 5' or 3' end of the polypeptide coding sequence; the oligonucleotide sequence encodes polyHis (such as hexa-His), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as peptidase cleavage.

Vectors typically contain a promoter that is recognized by the host organism and operably linked to the polynucleotide encoding the polypeptide. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known.

Suitable promoters for use with yeast hosts, bacterial hosts, and insect hosts are well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

The vector may contain one or more elements that facilitate expression when the vector is integrated into the host cell genome. Examples include an EASE element (Aldrich et al. 2003 Biotechnol Prog. 19:1433-38) and a matrix attachment region (MAR). MARs mediate structural organization of the chromatin and may insulate the integrated vector from "position" effects. Thus, MARs are particularly useful when the vector is used to create stable transfectants.

A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

After the vector has been constructed and the polynucleotide has been inserted into the proper site of the vector, the completed vector may be inserted into a suitable host cell for amplification and/or polypeptide expression. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. The host cells can be transfected transiently or the host cells can be transfected stably. These methods and other suitable methods are well known to the skilled artisan, and are set forth, for example, in Sambrook et al., 2001, supra.

For long-term, high-yield production of recombinant proteins, stable expression is often preferred. For example, cell lines that stably express the engineered heavy and light chains of the stabilized chimeric Fab can be prepared. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA or polynucleotide, engineered cells are allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems can be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

A host cell, when cultured under appropriate conditions, produces the stabilized chimeric Fab that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product can be used.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides described herein. In general, host cells are transformed with a recombinant expression vector that comprises DNA encoding the stabilized chimeric Fab. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, C127 cells, 3T3 cells (ATCC CCL 163), Chinese hamster ovary (CHO) cells, or their derivatives such as Veggie CHO and related cell lines which grow in serum-free media (Rasmussen et al., 1998, Cytotechnology 28: 31), HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces strains, Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides.

If the stabilized chimeric Fab is produced in yeast or bacteria, it may be desirable to modify the product produced therein, for example by phosphorylation or glycosylation of the appropriate sites, in order to obtain a functional product. Such covalent attachments can be accomplished using known chemical or enzymatic methods. The antibody construct can also be produced by operably linking the set of polynucleotides to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac™ kit), and such methods are well known in the art, as described in Summers and Smith, Texas Agricultural Experiment Station Bulletin No. 1555 (1987), and Luckow and Summers, Bio/Technology 6:47 (1988). Appropriate cloning and expression vectors for use with bacterial, fungal, yeast, and mammalian cellular hosts are described by Pouwels et al. (Cloning Vectors: A Laboratory Manual, Elsevier, New York, 1985).

In certain embodiments, cell-free protein expression systems can be utilized to co-express polypeptides (e.g., heavy and light chain polypeptides) from the set of polynucleotides without the use of living cells. Instead, all components needed to transcribe DNA to RNA and translate the RNA to protein (e.g. ribosomes, tRNAs, enzymes, cofactors, amino acids) are provided in solution for use in vitro. In certain embodiments, the in vitro expression requires (1) the genetic template (mRNA or DNA) encoding the heavy and light chain polypeptides and (2) a reaction solution containing the necessary transcriptional and translational molecular machinery. In certain embodiments, cell extracts substantially supply components of the reaction solution, for instance: RNA polymerases for mRNA transcription, ribosomes for polypeptide translation, tRNA, amino acids, enzymatic cofactors, an energy source, and cellular components essential for proper protein folding. Cell-free protein expression systems can be prepared using lysates derived from bacterial cells, yeast cells, insect cells, plant cells, mammalian cells, human cells or combinations thereof. Such cell lysates can provide the correct composition and proportion of enzymes and building blocks required for translation. In some embodiments, cell membranes are removed to leave only the cytosolic and organelle components of the cell.

Several cell-free protein expression systems are known in the art as reviewed in Carlson et al. (2012) Biotechnol. Adv. 30:1185-1194. For example, cell-free protein expression systems are available based on prokaryotic or eukaryotic cells. Examples of prokaryotic cell-free expression systems include those from *E. coli*. Eukaryotic cell-free protein expression systems are available based on extracts from rabbit reticulocytes, wheat germ, and insect cells, for example. Such prokaryotic and eukaryotic cell-free protein expression systems are commercially available from companies such as Roche, Invitrogen, Qiagen, and Novagen. One skilled in the art would readily be able to select suitable cell-free protein expression systems that would produce polypeptides (e.g., heavy chain and light chain polypeptides) that are capable of pairing with each other. Further, the cell-free protein expression system can also be supplemented with chaperones (e.g. BiP) and isomerases (e.g. disulphide isomerase) to improve the efficiency of IgG folding.

Co-Expression of Heavy Chains and Light Chains

The engineered immunoglobulin heavy chains and light chains of the stabilized chimeric Fab described herein can be co-expressed in mammalian cells, as noted above. In one embodiment, the immunoglobulin heavy chains and immunoglobulin light chains of the stabilized chimeric Fab are co-expressed in a host cell. Thus, in the case of a bispecific antibody construct comprising at least one stabilized chimeric Fab, a second Fab and an Fc scaffold, two immunoglobulin heavy chains (H1 and H2) and two immunoglobulin light chains (L1 and L2) are co-expressed in a host cell to form an H1L1 pair that binds to a first epitope and an H2L2 pair that binds to a second epitope. However, alternate methods of producing bispecific antibody constructs that do not rely on the use of a single clonal or transient cell line expressing all four chains are also known in the art (Gramer, et al. (2013) mAbs 5, 962; Strop et al. (2012) J Mol Biol 420, 204.). These methods rely on a post-production arm exchange under redox conditions of the two pairs of light and heavy chain involved in the formation of bispecific antibody (Redox production). In this approach the H1L1 and H2L2 heterodimers can be expressed in two different cell lines to independently produce the two heterodimers. Subsequently, the two heterodimers are mixed under select redox conditions to achieve re-association of the two unique heavy chain H1 and H2 to form the bispecific antibody construct comprising H1L1H2L2.

In some embodiments the amount of desired bispecific antibody resulting from co-expression of two unique heavy chains and two unique light chains is increased by amino acid modifications in the CH3 domains of the two heavy chains that promote preferential pairing between H1 and H2 as described elsewhere herein. In some embodiments, the amount of desired bispecific antibody resulting from co-expression of two unique heavy chains and two unique light chains is increased by amino acid modifications in the CH1 and CL domains and/or in the VH and VL domains of these chains which promote preferential pairing between heavy and light chains. Examples of the latter amino acid modifications are described in International Publication Nos. WO2014/082179 and WO2015/181805.

Although preferential pairing is driven mainly by the incorporation of the amino acid modifications in the CH1/CL and/or VH/VL domains into the immunoglobulin heavy and light chain polypeptides, the amount of correctly-paired heterodimers may further be optimized by varying the ratio of the polynucleotides encoding each polypeptide to each other, as shown in the Examples.

Testing of Stabilized Chimeric Fabs

The affinity of each stabilized chimeric Fab for its respective antigen can be tested as described below. The thermal stability of each stabilized chimeric Fab can also be tested as described below.

Thermal Stability

The thermal stability of the stabilized chimeric Fabs can be determined according to methods known in the art. The melting temperature of each stabilized chimeric Fab is indicative of its thermal stability. The melting temperature of the stabilized chimeric Fab can be measured using techniques such as differential scanning calorimetry (Chen et al (2003) Pharm Res 20:1952-60; Ghirlando et al (1999) Immunol Lett 68:47-52), and differential scanning fluorimetry (Niesen et al. (2007) Nature Protocols 2(9): 2212-21). The latter methods provide a measure of thermal stability in terms of "melting temperature" or Tm. Alternatively, the thermal stability of the stabilized chimeric Fab can be measured using circular dichroism (Murray et al. (2002) J. Chromatogr Sci 40:343-9). In one embodiment, the thermal stability of the stabilized chimeric Fab, or antibodies comprising the stabilized chimeric Fab is measured by differential scanning calorimetry (DSC). In one embodiment, the thermal stability of the stabilized chimeric Fab, or antibodies comprising the stabilized chimeric Fab is measured by differential scanning fluorimetry (DSF). In one embodiment, the thermal stability of the stabilized chimeric Fab, or antibodies comprising the stabilized chimeric Fab is measured by DSC or DSF.

Affinity for Antigen

The binding affinity of the stabilized chimeric Fabs for their respective antigens and the off-rate of the interaction can be determined by competitive binding assays according to methods well known in the art. One example of a competitive binding assay is a radioimmunoassay comprising the incubation of labeled antigen (e.g., 3H or 125I with a molecule of interest (e.g., stabilized chimeric Fabs of described here) in the presence of increasing amounts of unlabeled antigen, and the detection of the molecule bound to the labeled ligand. The affinity of the stabilized chimeric Fabs for the antigen and the binding off-rates can be determined from the saturation data by Scatchard analysis.

The kinetic parameters for binding of a stabilized chimeric Fab described herein to an antigen can also be determined using surface plasmon resonance (SPR) based assays known in the art (e.g., Biacore™ kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of assessing the ability of a stabilized chimeric Fab to bind to antigen. Other methods known in the art, including FACS and bio-layer interferometry (BLI, described in Determining Kinetics and Affinities of Protein Interactions Using a Parallel Real-time Label-free Biosensor, the Octet®. Abdiche, Y. N.; Malashock, D. S.; Pinkerton, A; Pons, J. Analytical Biochemistry, 2008, 377(2), 209-217), may also be used to measure affinity. In one embodiment, the ability of a stabilized chimeric Fab or antibody comprising a stabilized chimeric Fab to bind to target antigen is measured by SPR. In one embodiment, the affinity of a stabilized chimeric Fab or antibody comprising a stabilized chimeric Fab towards its target antigen is measured by SPR.

Pharmaceutical Compositions

Also provided herein are pharmaceutical compositions comprising the stabilized chimeric Fabs or antibody constructs described herein. Such compositions comprise a therapeutically effective amount of the stabilized chimeric Fab, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the stabilized chimeric Fab or antibody constructs comprising a stabilized Fab are formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a therapeutic protein can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Uses

As described above, the stabilized chimeric Fabs and antibody constructs comprising stabilized chimeric Fabs are obtained from one or more parent antibodies. Accordingly, they can be used in the treatment or prevention of the same diseases, disorders, or infections in a subject that the parent antibody or combination of parent antibodies is used for. In one embodiment, the subject is a mammal. In one embodiment, the subject is a human.

In another embodiment, the stabilized chimeric Fabs and antibody constructs comprising stabilized chimeric Fabs described herein can also be utilized in combination with other therapeutic agents known in the art for the treatment or prevention of a cancer, autoimmune disease, inflammatory disorders or infectious diseases in a subject. In a specific embodiment, the stabilized chimeric Fabs and antibody constructs comprising stabilized chimeric Fabs described herein can be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The stabilized chimeric Fabs and antibody constructs comprising stabilized chimeric Fabs described herein can also be utilized in combination with one or more drugs used to treat a disease, disorder, or infection such as, for example anti-cancer agents, anti-inflammatory agents or anti-viral agents.

In another embodiment, the stabilized chimeric Fabs can be used in the preparation of antibody constructs of varying formats, as described herein. In certain embodiments, the stabilized chimeric Fabs can be used in the preparation of bispecific antibody construct. An example of such use is described in Example 14.

In yet another embodiment, the stabilized chimeric Fabs can be used in a method to increase the stability of a lambda antibody (i.e. a parent lambda antibody comprising an immunoglobulin heavy chain and a lambda light chain), or lambda Fab in cases where this is desirable. For example, in order to increase the stability of a parent lambda antibody, a Vlambda-Ckappa chimeric light chain comprising the Vlambda sequence of the parent lambda antibody and a Ckappa sequence can be prepared, wherein the Vlambda sequence comprises one or more of the stabilizing amino acid modifications described herein. The Vlambda-Ckappa chimeric light chain can then be used to prepare an antibody comprising the Vlambda sequence. For example, the Vlambda-Ckappa chimeric light chain may be co-expressed with the immunoglobulin heavy chain to obtain a chimeric antibody with increased thermal stability compared to the parent lambda antibody. Alternatively, the Vlambda-Ckappa chimeric light chain may be co-expressed with an immunoglobulin heavy chain fragment comprising VH and CH1 domains to obtain a chimeric Fab with increased stability compared to the parent lambda Fab.

EXAMPLES

Below are examples of specific embodiments for making and using the stabilized chimeric Fabs described herein. The examples are offered for illustrative purposes only, and are not intended to limit the scope of the disclosure in any way. Efforts have been made to ensure accuracy with respect to numbers used (e.g., amounts, temperatures, etc.), but some experimental error and deviation should, of course, be allowed for.

The constructs and methods described herein can be prepared and carried out employing, unless otherwise indicated, conventional methods of protein chemistry, biochemistry, recombinant DNA techniques within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols. A and B(1992).

EXAMPLES

Example 1: Amino Acid Conservation and Structure-Guided Design at the Vlambda and Ckappa Interface in the Vlambda-Ckappa Chimera Light Chain In many cases, it has been observed that Fabs containing chimeric light chains (chimeric Fabs) exhibit a drop in thermal stability compared to Fabs containing a wild-type light chain. Therefore, a structure-guided and amino acid conservation-guided approach was primarily used to engineer solutions for improving the thermal stability of Fabs containing a chimeric light chain, the chimeric light chain composed of a variable lambda domain and a constant kappa domain. This type of chimeric light chain is referred to herein as a Vlambda-Ckappa chimeric light chain (VL-CK chimeric light chain), and a chimeric Fab containing this type of chimeric light chain is referred to herein as a VL-CK chimeric Fab. A representation of a VL-CK chimeric Fab is shown in FIG. 1. The sequence of a representative VL-CK chimeric light chain compared to that of a wild-type lambda Fab (CAT-2200) is shown in FIG. 2.

Structure-guided analysis was primarily performed on representative X-ray crystal structures of human or humanized Fabs containing kappa light chains and on human or humanized Fabs containing lambda light chains, as well as on the few available Fabs containing a Vlambda-Ckappa chimeric light chain. Representative kappa and lambda Fab structures were identified in the following way. Analysis of the inter-domain contacts of the variable:constant domain interface in the light chain was performed on a set of non-redundant lambda and kappa human/humanized Fab structures found in the Monoclonal Antibodies Database hosted by IMGT® using an in silico tool which provided an analysis of the number of residues in contact at the interface of interest, as well as a per residue analysis of the number of contacting residues. This analysis determined that there was a different distribution of number of contacts at the variable:constant interface in lambda Fab light chains compared to the distribution in kappa Fabs. The Fabs of antibodies D3H44 and CAT-2200 were chosen as kappa Fab representative and lambda Fab representative, respectively, for analysis. These Fabs displayed an average number of interface contacts at the variable:constant domain interface for kappa and lambda Fab structures, respectively. A visual analysis of the variable:constant interface in light chains of these representative kappa and lambda Fab structures was then carried out to identify important residues at such interfaces. Together with the visual analysis of few available Vlambda-Ckappa Fab structures, it was further used to identify any incompatibilities in variable:constant interface in chimeric light chain. The above analysis was aided by residue conservation analysis and per residue contact analysis obtained with the in silico tool. Residue conservation analysis was performed for the variable:constant domain light chain interface by performing sequence alignments of non-redundant human and humanized kappa and lambda sequences (IMGT database) to identify most common residue type in the positions of interest (important residues) at the interface.

The above analysis highlighted differences at the variable:constant domain interface of kappa light chains compared to lambda light chains, and led to the hypothesis that suboptimal compatibility in the chimeric interface between the Vlambda and Ckappa domains of the chimeric light chain was likely related to the observed decrease in thermal stability of Fabs containing chimeric light chain. Several hot spot residues at the Vlambda:Ckappa interface were identified, including positions 83, 85 and 105 (numbered according to Kabat, and as shown in Table 1 and FIG. 3). Throughout the examples, amino acid positions in the Fab region are identified according to the Kabat numbering system, unless otherwise indicated. Several sets of amino acid substitutions (referred to as "designs") in the variable domain of the Vlambda-Ckappa chimeric light chain were proposed to improve the compatibility of the Vlambda-Ckappa interface by mimicking the interface observed between variable kappa and constant kappa domains (Vkappa-Ckappa), as shown in FIG. 1, and thus improve the thermal stability of the respective chimeric Fabs. Hence, chimeric Fab variants comprised a heavy chain that was not modified to improve thermal stability and a Vlambda-Ckappa chimera light chain including amino acid substitutions proposed to improve thermal stability of the VL-CK chimeric Fab.

Three representative VL-CK chimeric Fab test systems were chosen for evaluation of the designs. These test systems met the following criteria: a) ability to be produced with sufficient yield to enable practical testing, b) exhibition of decreased thermal stability in VL-CK chimeric Fab format compared to the Fab of the parental wild-type antibody, c) ability to bind antigen with affinity comparable to that of parental wild-type antibody, and d) coverage of distinct human frameworks (specifically, human VH and lambda VL subgroups). The representative VL-CK chimeric Fabs contained chimeric light chains having a Vlambda domain from the following antibodies: CAT-2200 Fab (anti-IL17; hIGHV3, hIGLV6), H3 (anti-HER3; hIGHV3, hIGLV2) and EP6b_B01 (anti-Fas; hIGHV4, hIGLV1). The Vlambda-Ckappa chimeric light chain construct was composed of the lambda variable domain sequence terminated at position L106A and the kappa constant domain sequence corresponding to IGKC*01 (one of the most common human kappa allele sequences) starting at position R108. FIG. 2 provides an example of a chimeric light chain sequence, in this case for the CAT-2200 Fab. For reference, Table 1 provides the numbering of amino acids for the light chain variable domains for CAT-2200, H3 and EP6b_B01, according to Kabat.

Example 2: Stability Optimization Designs

Based on the analysis described in Example 1, a number of designs were proposed to improve the thermal stability of VL-CK chimeric Fabs. Amino acid substitutions at the hotspot positions 83, 85 and 105 in the Vlambda domain and at other secondary positions were selected to introduce the most conserved amino acid type at those positions in kappa variable domains (e.g 83F) as well as less conserved amino acid types (for example, 83V/83I/83A). As a primary hotspot, amino acid substitutions at position 83 define what are referred to in the examples as 'design themes,' for example, '83F theme,' '83V theme,' '83I theme,' or '83A theme.' A total of 39 designs were proposed for testing, as shown in Table 3. The amino acid substitutions introduced in the VL-CK chimeric light chains for improving thermal stability are herein referred to as "stability optimization designs," or simply "designs." As noted elsewhere, the amino acid positions substituted in the designs are identified throughout the application using the Kabat numbering system. Table 1 provides a reference for the Kabat numbering of variable domains for the CAT-2200, H3, and EP6b_B01 lambda light chains.

The 39 stability optimization designs listed in Table 3 were tested for their ability to improve the stability of VL-CK chimeric Fabs as described in the following examples.

Example 3: Preparation of Control Constructs and Constructs with Stability Optimization Designs The stability optimization designs were tested in Fab format and in Mab format, both of which are monospecific formats in this example, based on the parent antibodies CAT-2200, H3 and EP6b_B01 (note that EP6b_B01 system was not tested in Mab format). The Fab format was used as a simplified system in which to test the initial rounds of designs. Selected designs were subsequently tested in the context of a full-sized antibody, in Mab format.

Constructs in the Fab format included a truncated heavy chain comprising CH1 and VH domains and a parental lambda light chain (wild-type Fab controls), or a VL-CK chimeric light chain (VL-CK chimeric Fabs), wherein the truncated heavy chain and the Vlambda domain of the VL-CK chimeric light chain are from the parent antibody, and the Ckappa domain of the VL-CK chimeric light chain is the kappa constant domain sequence corresponding to IGKC*01. Constructs in the Fab format, with stability optimization designs in the VL-CK chimeric light chain are referred to as "designed chimeric Fabs" (see FIG. 1 for a representation of this type of construct).

Figure 4:
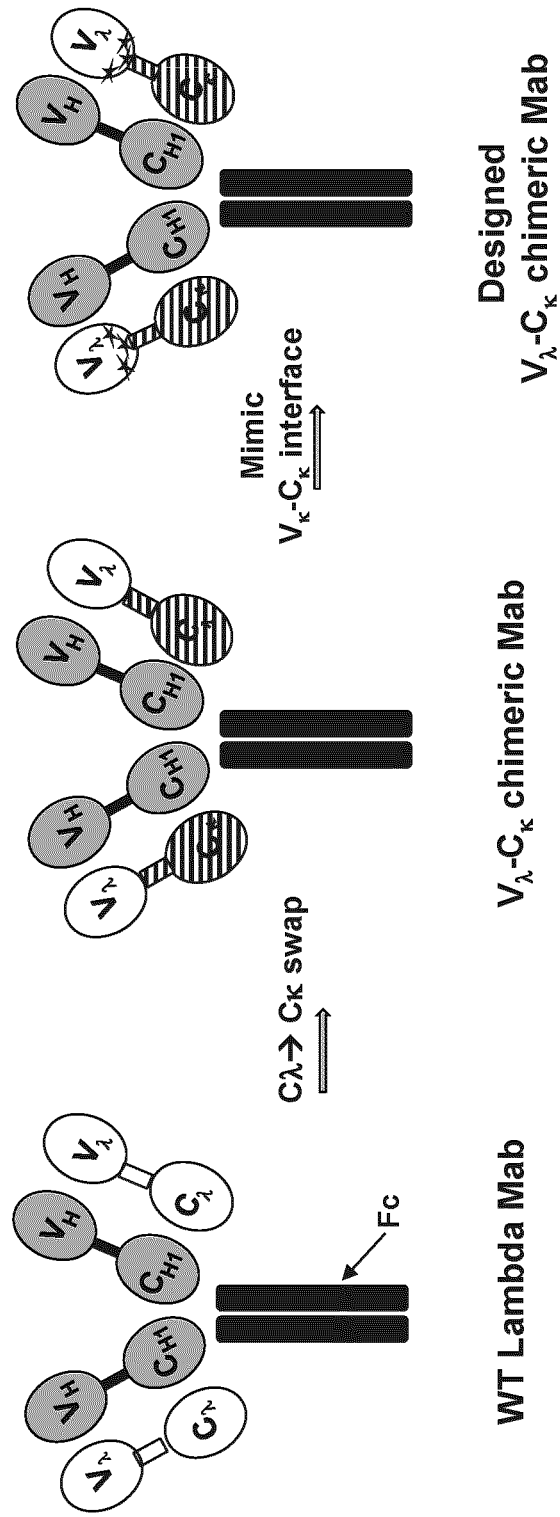
FIG. 4 portrays an analogous schematic to that in FIG. 1, applied to the Mab format, depicting a WT lambda Mab, a Vlambda-Ckappa chimeric Mab and a designed Vlambda-Ckappa chimeric Mab (also referred to as a stabilized Mab), where star symbols denote the presence of a stability optimization design.

Constructs in the Mab format had two identical full-length heavy chains corresponding to the parent antibody, and two identical parental lambda light chains (wild-type Mab controls) or two identical VL-CK chimeric light chains where the Vlambda domain of each VL-CK chimeric light chain is from the parent antibody, and the Ckappa domain is the kappa constant domain sequence corresponding to IGKC*01 (chimeric Mabs). Constructs in the Mab format, with stability optimization designs in the VL-CK chimeric light chain are referred to as "designed chimeric Mabs." FIG. 4 provides exemplary structures of these Mab constructs.

Preparation of Constructs in Fab Format

Two types of Fab format controls were used for the evaluation of the designs. "Wild-type" lambda Fab constructs based on the parent antibodies CAT-2200, H3 and EP6b_B01 contained a truncated unmodified heavy chain (having VH and CH1 domains) and a wild-type lambda light chain from the parent antibody. Chimeric Fab constructs contained unmodified truncated heavy chains and a VL-CK chimeric light chain with the parental Vlambda domain and Ckappa domain with sequence corresponding to IGKC*01. FIG. 1 depicts representations of a wild-type lambda Fab construct (WT lambda Fab) and of a chimeric Fab construct ($V_\lambda$-$C_\kappa$ chimeric Fab).

The truncated heavy chain, wild-type light chain, and VL-CK chimeric light chain of the CAT-2200 parent antibody were prepared as follows. The protein sequences of the CAT-2200 Fab light chain (2VXS chain L, SEQ ID NO:8) and truncated heavy chain (2VXS chain H, SEQ ID NO:7) including the upper IgG1 hinge 'EPKSCDKTHT' (SEQ ID NO:30) were taken from the PDB entry 2VXS 9, reverse translated to DNA, codon optimized for mammalian expression, and gene synthesized (SEQ ID NOs: 23 and 22, respectively). The Vlambda-Ckappa chimera light chain was composed of the CAT-2200 Vlambda domain sequence, terminated at the position L106A, and the Ckappa domain sequence corresponding to IGKC*01, from position R108 of the Ckappa sequence, as shown in FIG. 2. The protein sequence for the CAT-2200 Vlambda-Ckappa chimera light chain is set forth in SEQ ID NO: 9 and the DNA sequence is set forth in SEQ ID NO: 24.

The truncated heavy chain, wild-type light chain, and VL-CK chimeric light chain of the H3 parent antibody were prepared as follows. The protein sequence of the H3 antibody VL domain was obtained from SEQ ID NO: 4, residues 156-267 of U.S. Pat. No. 8,329,873 and the protein sequence of the VH domain of this antibody was obtained from SEQ ID NO:4, residues 23-140 of the same patent. The VH domain sequence was appended to the CH1 domain sequence of IGHG1*01 (SEQ ID NO:31) to obtain a protein sequence for the truncated heavy chain for the Fab (SEQ ID NO:1), including the upper IgG1 hinge 'EPKSCDKTHT' (SEQ ID NO:30). The VL domain sequence was appended to the lambda CL sequence of IGLC2 to obtain a protein sequence for a "wild-type" light chain for the H3 antibody (SEQ ID NO:2). These sequences were reverse translated to DNA, codon optimized for mammalian expression, and gene synthesized (SEQ ID NO:17 for the light chain and SEQ ID NO:16, for the truncated heavy chain). The protein sequence for the H3 Vlambda-Ckappa chimera light chain was obtained as described for the CAT-2200 antibody, and the resulting amino acid sequence is set forth in SEQ ID NO:3. The DNA sequence encoding the H3 VL-CK chimeric light chain is set forth in SEQ ID NO: 18.

The truncated heavy chain, wild-type light chain, and VL-CK chimeric light chain of the EP6b_B01 parent antibody were prepared as follows. The protein sequences of the EP6b_B01 Fab light chain (3THM chain L, SEQ ID NO:5) and heavy chain (3THM chain H, excluding the C-terminal 10xHis-tag sequence, SEQ ID NO:4) including the upper IgG1 hinge 'EPKSCDKTHT' (SEQ ID NO:30) were taken from PDB entry 3THM, reverse translated to DNA, codon optimized for mammalian expression, and gene synthesized (SEQ ID NOs: 20 and 19, respectively). The protein sequence for the EP6bB01 Vlambda-Ckappa chimera light chain was obtained as described for the CAT-2200 antibody and is set forth in SEQ ID NO:6. The DNA sequence encoding the EP6b_B01 VL-CK chimeric light chain is set forth in SEQ ID NO: 21.

The polypeptide and DNA sequences of the above noted antibody heavy chains, light chains, and VL-CK chimeric light chains are provided in Table 2.

Light chain amino acid substitutions corresponding to the stability optimization designs of designed chimeric Fabs were generated in VL-CK chimeric light chain DNA sequences, primarily by site-directed mutagenesis (Braman J, Papworth C & Greener A., Methods Mol. Biol. (1996) 57:31-44).

Light chain vector inserts, consisting of a 5'-EcoRI cut site—HLA-A signal peptide—wild-type light chain or VL-CK chimeric light chain sequences—'TGA or TAA stop'—BamH1 cutsite-3', were ligated into a pTT5 vector (Durocher Y et al., Nucl. Acids Res. 2002; 30, No. 2 e9) to produce light chain expression vectors. The resulting light chain expression vectors were sequenced to confirm correct reading frame and sequence of the coding DNA. Likewise, heavy chain vector inserts, consisting of a 5'-EcoR1 restriction site—HLA-A signal peptide—heavy chain sequence (terminating at T238 (Kabat numbering)—'TGA or TAA stop'—BamH1 cutsite-3', were ligated into a pTT5 vector to produce heavy chain expression vectors. The resulting heavy chain expression vectors were also sequenced to confirm correct reading frame and sequence of the coding DNA.

Preparation of Constructs in Mab Format

As for the Fab format, two analogous types of Mab format controls were used for the evaluation of the designs: "Wild-type" lambda Mab constructs based on the parent antibodies CAT-2200, H3 and EP6b_B01, contained full-length unmodified heavy chains and light chains from the parent antibody. Chimeric Mab constructs contained an unmodified heavy chain and chimeric light chain.

The protein sequences for wild-type light chains and VL-CK chimeric light chains for each Mab control construct were obtained as described for the constructs in Fab format. The sequence for the full-length heavy chain of the CAT-2200 antibody was obtained from PDB entry 2VXS, corresponding to the short heavy chain as described in section 'Preparation of constructs in Fab format', followed by appending the sequence of the lower IgG1 hinge ('CPPCP', SEQ ID NO:32), CH2 and CH3 domains (SEQ ID No. 15 in Table 2). This sequence was reverse translated to DNA, codon optimized for mammalian expression, and gene synthesized. The protein sequence for the full-length heavy chain of the H3 antibody in a similar manner, based on the H3 heavy chain sequence.

Light chain and chimeric light chain vectors for creating Mab contracts were prepared in the same manner as for Fab constructs, with light chain amino acid substitutions corresponding to the stability optimization designs being generated as described above. Heavy chain vector inserts, consisting of a 5'-EcoR1 restriction site—HLA-A signal peptide—heavy chain clone terminating at G446 (EU numbering) of CH3—'TGA or TAA stop'—BamH1 cutsite-3', were ligated into a pTT5 vector to produce heavy chain expression vectors. As described above, the resulting heavy chain expression vectors were also sequenced to confirm correct reading frame and sequence of the coding DNA.

Example 4: Expression and Purification of Designed Chimeric Fabs and Designed Chimeric Mabs The heavy and light chains of control Fab and Mab constructs, as well as designed chimeric Fab and designed chimeric Mab constructs were expressed in 50 or 200 ml cultures of CHO-3E7 cells. CHO-3E7 cells, at a density of $1.7$-$2 \times 10^6$ cells/ml, were cultured at 37° C. in FreeStyle™ F17 medium (Gibco cat #A-1383501) supplemented with 4 mM glutamine (Hiclone cat #SH30034.01) and 0.1% KoliphorP188 (Sigma #K4894). A total volume of 50 or 200 ml was transfected with a total of 50 or 200 µg DNA (e.g. for the case of 200 µl, 100 µg of Fab/Mab DNA and 100 µg of GFP/AKT/stuffer DNA) using PEI-pro respectively (Polyplus cat #115-375) at a DNA:PEI ratio of 1:2.5 or PEI-max (Polyscience cat: 24765) at a DNA:PEI ratio of 1:4. Twenty-four hours after the addition of the DNA-PEI mixture, 0.5 mM valproic acid (final concentration) and 1% w/v Tryptone (final concentration) were added to the cells (+antibiotic 1× from Hi-clone cat #SV30079) which were then transferred to 32° C. and incubated for 7 days prior to harvesting.

Fab Construct Purification

Control and designed chimeric Fab constructs were purified from clarified supernatant (following cell harvest) by affinity capture using IgG-CH1 CaptureSelect™ (Life Technologies™, Catalog No.: 194-320-005) by batch or mixed batch:column chromatography. Supernatants were diluted to 20-25% clarified supernatant in equilibration buffer (Dulbecco's phosphate buffered saline (DPBS) without Calcium, Magnesium, and phenol red (HyClone™#SH30028.02)) or in some instances directly incubated with mixing for 16 hours with IgG-CH1 CaptureSelect™ (previously equilibrated with the equilibration buffer) at 4° C. The resin containing bound proteins was either poured into Econo columns (Bio-Rad) or it was collected by centrifugation and transferred to a 96 well-fritted plate. Both methods included wash step with equilibration buffer, followed by elution step performed with 100 mM glycine HCl pH 2.6-2.7 and immediate neutralization of the eluted samples to pH 6.0-7.0 using 10% (v/v) 1M Tris pH 9.0. Protein quantitation was performed by A280 nm using a spectrophotometer (NanoDrop™).

In cases where the designed chimeric Fabs and/or controls exhibited suboptimal binding profiles to IgG-CH1 CaptureSelect™, these Fabs were purified from clarified supernatant using kappa-select resin as follows. Proteins were purified using KappaSelect™ resin (GE Healthcare), either in batch mode or using packed 1 mL HiTrap columns using a Protein Maker instrument (Protein BioSolutions). Resin was equilibrated in DPBS and either the clarified supernatant applied to a pre-packed 1 mL HiTrap column with a residence time of 3 min/mL or for batch purification, resin added to clarified supernatants with overnight agitation at 4° C. Following protein binding to the resin, a wash step was performed with the equilibration buffer, which was followed with the elution step using 100 mM glycine HCl pH 2.6-2.7. Eluted samples were immediately pH adjusted to pH 6-7 using 10% (v/v) 1 M tris(hydroxymethyl)aminomethane, 2-Amino-2-(hydroxymethyl)-1,3-propanediol (Tris) base pH 9. Protein quantitation was performed by A280 nm using a spectrophotometer (NanoDrop™)

Mab Construct Purification

Clarified supernatant samples were applied to 1 mL HiTrap mAb Select SuRe columns (GE Healthcare) equilibrated in DPBS or incubated with mAb Select SuRe resin slurry (previously equilibrated in DPBS buffer) overnight at 2-8° C. (batch mode). Batch mixture was then transferred into a chromatography column and flow-through was collected. Columns were washed with DPBS and protein eluted with 100 mM sodium citrate buffer pH 3.0. The elutions were performed into 10% (v/v) 1M Tris pH 8 to yield a final pH of 6-7. Protein was quantitated based on A280 nm using a spectrophotometer (Nanodrop™).

Following purification, expression of both Fab and Mab constructs was assessed by non-reducing High Throughput Protein Express assay using Caliper LabChip GXII (Perkin Elmer #760499). Procedures were carried out according to HT Protein Express LabChip User Guide version2 LabChip GXII User Manual, with the following modifications. Fab/Mab samples, at either 2 µl or 5 µl (concentration range 5-2000 ng/µl), were added to separate wells in 96 well plates (BioRad #HSP9601) along with 7 µl of HT Protein Express Sample Buffer (Perkin Elmer #760328). Fab/Mab/bsAb samples were then denatured at 70° C. for 15 mins. The LabChip instrument was operated using the HT Protein Express Chip (Perkin Elmer #760499) and the Ab-200 assay setting.

Effect of Stability Optimization Designs on Protein Expression

Figure 5:
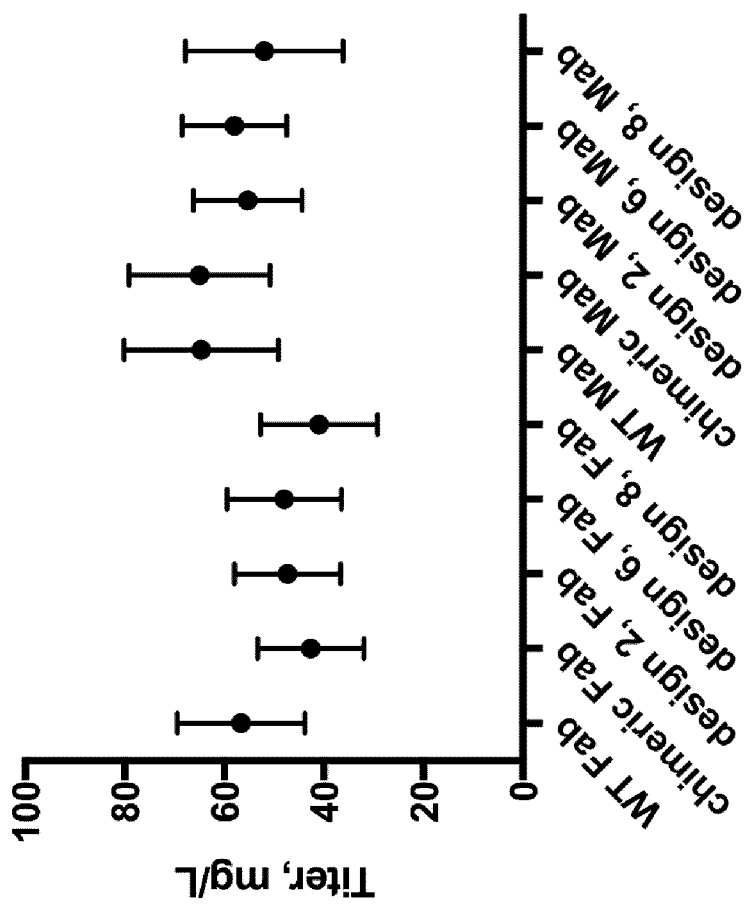
FIG. 5 provides comparison of protein-A titers for selected designed chimeric Fabs (the variable region of the CAT-2200 antibody heavy chain belongs to the VH3 germline subgroup and has the ability to bind protein-A), Mabs and respective wild-type formats in the CAT-2200 system. Average protein-A titers (mg/L) from three independent 50 ml transfections are plotted.

FIG. 5 compares the titer of Fab and Mab constructs for controls and selected designed chimeric Fabs or designed chimeric Mabs based on the parent CAT-2200 antibody. Expression of the chimeric Fab and designed chimeric Fabs was somewhat lower compared to expression of the wild-type lambda Fab. Expression of designed chimeric Mabs was somewhat lower compared to the wild-type lambda Mab and chimeric Mab. Inclusion of stability optimizing mutations in the chimeric format did not have a significant impact on protein expression (compare expression of designed chimeric Fabs with that of the wild-type lambda Fab, and expression of the designed chimeric Mab with that of the wild-type lambda Mab).

As noted in Example 3, some designed chimeric Fabs exhibited suboptimal purification efficiency with the IgG-CH1 CaptureSelect™ approach, however, when these same designed chimeric Fabs were purified by KappaSelect™ or the analogous designed chimeric Mabs were purified by protein-A, they behaved similarly to the other designed chimeric Fabs/designed chimeric Mabs. Some of these designed chimeric Fabs/designed chimeric Mabs belonged to the 83A or 83V themes. Without being limited in any way by the following, the observed variability in binding to IgG-CH1CaptureSelect™ resin may be due to variable conformational dynamics at the light: heavy chain interface or variable: constant interface (e.g. as a consequence of smaller amino acid substitution in the case of for example, the 83A theme vs. the 83F theme, for which purification efficiency was comparable to that of wild-type) rather than as a consequence of impaired structural integrity of these designed chimeric Fab constructs, for example. This hypothesis is supported by the comparable purification efficiency of such designed chimeric Fabs/designed chimeric Mabs to the rest of designed chimeric Fabs/designed chimeric Mabs purified by the two other alternative purification methods (described above) respectively.

Example 5: Preparative Size Exclusion Chromatography (SEC) of Designed Chimeric Fabs and Designed Chimeric Mabs for Biophysical Characterization Designed chimeric Fabs, designed chimeric Mabs and controls, prepared as described in Example 4, were subjected to preparative SEC to remove any impurities, prior to assessing their biophysical characteristics. Preparative SEC was carried out as follows. Antibody species in the samples were separated using a Superdex 200 10/300 or Superdex 200 10/300 Increase (GE Healthcare) column mounted on a GE Healthcare ÄKTA Avant 25 system equipped with an ALIAS Bio Cool autosampler (Spark-Holland) used to inject samples on the column. Samples in Fab or Mab formats (0.9 ml) in PBS pH 7.4 (Hyclone DPBS/modified, No Calcium, No Magnesium, Cat. No. SH-300028.02) were automatically loaded into a 2 ml loop filled with PBS. Samples were then automatically injected onto the column and resolved at 0.5 ml/min with a 1 CV elution volume (with some of the earlier purifications batches, sample loading was performed manually with 1 ml sample loop). Protein elution was monitored at OD280 and collected in 0.5 ml fractions. For each sample, fractions that comprised the main peak (fractions were assessed by Caliper) were pooled and further biophysically characterized as described in Examples 7-11.

Example 6: UltraPerformance Liquid Chromatography Size Exclusion Chromatography (UPLC-SEC) for Quality Assessment of Designed Chimeric Fabs and Designed Chimeric Mabs Designed chimeric Fab samples purified by the initial affinity chromatography step (IgG-CH1CaptureSelect™ or KappaSelect™) described in Example 4, as well as designed chimeric Mab samples purified by preparative SEC as described in Example 5, were subjected to UPLC-SEC in order to assess monodispersity of the samples after initial purification in the case of designed chimeric Fabs or during the course of the benchtop stability study in the case of designed chimeric Mabs (see Example 13).

UPLC-SEC was performed using a Waters™ Acquity BEH200 SEC column (2.5 mL, 4.6×150 mm, stainless steel, 1.7 μm particles) set to 30° C. and mounted on a Waters™ Acquity UPLC H-Class Bio system with a PDA detector. Run times consisted of 7 min and a total volume per injection of 2.8 mL with a running buffer of DPBS or DPBS with 0.02% polyethylene glycol sorbitan monolaurate (Tween® 20) pH 7.4 at 0.4 ml/min. Elution was monitored by UV absorbance in the range 210-500 nm, and chromatograms were extracted at 280 nm. Peak integration was performed using Empower 3 software.

UPLC-SEC analysis of designed chimeric Fab samples purified by IgG-CH1CaptureSelect™ was reflective of species homogeneity. UPLC-SEC profiles of designed chimeric Fabs purified by KappaSelect™ reflected impurities likely related to various light chain containing species most of which were subsequently removed by preparative SEC.

Example 7: Effect of Designs on Thermal Stability of Designed Chimeric Fabs

In order to determine the effectiveness of the stability optimization designs, the thermal stability of the designed chimeric Fabs and controls was assessed by differential scanning fluorescence (DSF) and/or differential scanning calorimetry (DSC) methods and compared to the thermal stability of the respective chimeric Fab. Designed chimeric Fabs and controls were purified as described in Example 5.

Measurement of Thermal Stability by DSC

The thermal stability of designed chimeric Fabs and controls was measured using DSC as follows. 400 μL of purified samples primarily at concentrations of 0.4 mg/mL (small subset of designed chimeric Fabs was at concentration of 0.175 mg/mL) in PBS were used for DSC analysis with a VP-Capillary DSC (GE Healthcare). At the start of each DSC run, 5 buffer blank injections were performed to stabilize the baseline, and a buffer injection was placed before each sample injection for referencing. Each sample was scanned from 20 to 100° C. at a 60° C./hr rate, with low feedback, 8 sec filter, 3 or 5 min pre-scan thermostat, and 70 psi nitrogen pressure. The resulting thermograms were referenced and analyzed using Origin 7 software to determine melting temperature (Tm) as an indicator of thermal stability.

Measurement of Thermal Stability by DSF

The thermal stability of designed chimeric Fabs and controls was measured using DSF as follows. Each purified designed chimeric Fab was diluted to 0.67 mg/mL in DPBS (Dulbecco's phosphate buffered saline, HyClone Cat #SH30028.02). A working stock of Sypro™ Orange gel stain (Life Technologies Cat #S-6650) was prepared by 1:1000 dilution in DPBS. The DSF samples were prepared by adding 15 μL of 0.67 mg/mL protein (10 μg) to 15 μL of the Sypro™ Orange gel stain working stock. However, for proteins that had a concentration less than 0.67 mg/mL, each DSF sample were prepared by adding 15 μL of 0.27 mg/ml (4 μg) protein or undiluted protein to 15 μL of a working stock of Sypro™ Orange dye. DSF analysis was then conducted on 30 μl aliquots using the Rotor-Gene® 6000 qPCR instrument (QiaGen Inc). Each sample was scanned from 30° C. to 94° C. using 1° C. intervals with a 10 second equilibrium between each step and a 30 second wait time at the start. An excitation filter of 470 nm and emission filter of 610 nm were used with the gain manually adjusted between 7-10 to ensure the samples were not saturating and were within the dynamic range of the detector. Data was analyzed with the Rotor-Gene® 6000 software using the maxima value from the first derivative of the denaturation curve as the Tm (melting temperature).

Results

Thermal Stability of Controls

As noted in Example 1, one of the criteria for selecting representative Fabs for testing the stability optimization designs was that a VL-CK chimeric Fab exhibited a decrease in thermal stability compared to a wild-type lambda Fab of the parent antibody. Table 4 shows the Tm values obtained for the wild-type lambda Fabs and the VL-CK chimeric Fabs (identified as "WT" and "chimera" in Table 4). Columns 8-13 show the Tm for these controls as measured by DSC, while columns 2 to 7 show the Tm for these controls as measured by DSF. In all cases, the VL-CK chimeric Fabs exhibited a decrease in Tm, with the amount of the decrease varying depending on the parent antibody. The mean Tm for the wild-type CAT-2200 lambda Fab construct was determined to be 78.8° C. and for the CAT-2200 chimeric Fab was determined to be 73.1° C. The mean Tm for the wild-type H3 lambda Fab construct was determined to be 80.9° C. and for the chimeric Fab was determined to be 76.0° C. The mean Tm for the wild-type lambda EP6b_B0I Fab construct was determined to be 85.4° C. and for the chimeric Fab was determined to be 80.5° C. These data demonstrate that conversion of wild-type lambda Fab to the Vlambda-Ckappa chimeric Fab is accompanied by the loss in thermal stability in the range of 4.9 to 5.7° C. as measured by DSF, while the decrease in Tm measured by DSC was between 3.7 and 4.6° C., suggesting this to be a likely trend in other systems as well.

Thermal Stability of Designed Chimeric Fabs

Based on the design strategy described in Example 1, an initial set of 8 designs (designs 1-8 as listed in Table 3) was tested in the single system CAT-2200 by DSC. Based on the results, a second set of designs (designs 9-39 in Table 3) were tested by DSF in the CAT-2200 and H3 systems in order to identify the amino acid substitutions that were most important in increasing the thermal stability of the VL-CK chimeric Fabs. Although DSF is known to be a less precise method for measuring melting temperatures, it was used here because it is a high throughput method of measuring thermal stability and is suitable for assessing the relative effect on stability compared to the controls.

DSC results for designed chimeric Fabs with designs 1-8 are reported in Table 4 (columns 8-13). Thermal stability data for the three systems are reported in columns 8 (CAT-2200), 10 (H3) and 12 (EP6b_B01). Comparisons of the designed chimeric Fab Tm values with respect to the Tm value of the respective Vlambda-Ckappa chimera system is reported in columns 9 (CAT-2200), 11 (H3) and 13 (EP6b_B01). For designed chimeric Fabs where repeats were conducted, the reported Tm value is the mean value.

DSF results for designed chimeric Fabs are reported in Table 4 (columns 2-7). Thermal stability data for three different test systems are reported in columns 2 (CAT-2200), 4 (H3) and 6 (EP6b_B01). For designed chimeric Fabs where repeats were conducted, the reported Tm value is the mean value Comparisons of the designed chimeric Fab Tm values with respect to the Tm value of the respective Vlambda-Ckappa chimera system is reported in columns 3 (CAT-2200), 5 (H3) and 7 (EP6b_B01).

The data in Table 4 demonstrate that with the chosen design strategy, wild-type stability was not only regained but also surpassed by up to 7.6° C. (design 39 in H3 system) as measured by DSF. Data based on two systems, CAT-2200 and H3, indicates that introduction of as few as a single amino acid substitution at residue 83X (where X=F/V/I/A, where these amino acid residues are the most conserved amino acid types in the kappa light chain, with F being the most conserved of all) can lead to sizable improvement in thermal stability compared to that of corresponding chimeric Fab, displaying an increase in stability between 1.8-7.4° C. (See FIG. 6A, FIG. 6B and Table 4: designs 14, 23, 30 and 35). Designs in which the amino acid at position 83 was substituted with V, I, or A have a Tm surpassing that of even the wild-type lambda Fab. Hence, the E83X was determined to be a core position for substitution. Substitution with amino acid L at this position was tested experimentally in the CAT-2200 system in chimeric Fab format (data not provided) and variants containing such substitution (for example: 83L_105E_106AK, and other combos including 85T and 106I) demonstrated similar behavior in terms of thermostability improvement as the hydrophobic amino acid substitutions for which data is provided herein.

Figure 6A:
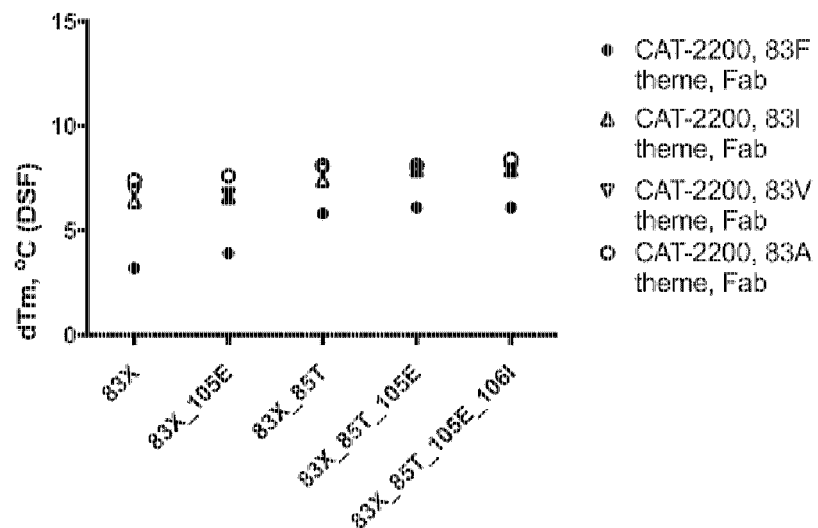
FIG. 6A-6B depicts the effect of stabilizing amino acid modifications within and across 83X design themes, where X=F, V, I, A, based on different parent chimeric Fabs.
Figure 6B:
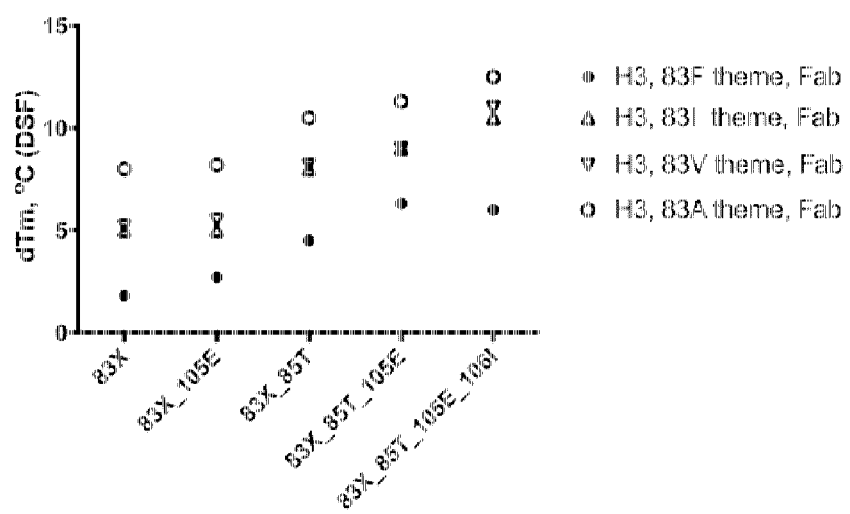

Introduction of an additional amino acid substitution at position 85 to obtain the 83X_85T design resulted in a further increase in thermal stability, the extent of which seemed to be system-dependent (FIG. 6A, FIG. 6B, and Table 4: designs 17, 26, 32 and 37). Further extension of the design to 83X_85T/V_105E or 83X_85T_105E_106I led to even further improvement in Tm, the extent of which was dependent on the system tested (FIG. 6A, FIG. 6B, and Table 4). Amino acid substitutions at position 85 with most conserved amino acid types in kappa light chain, namely T and V, in the context of the designs tested contributed to identical improvement in Tm.

Example 8: Transferability of the Effect of Stability Optimization Designs in Fab Format In order to further assess transferability of stability optimization designs, a subset of designs of type 83X_85T, 83X_85T_105E_106I, where X=V/I/A and 83F_85T_105E were selected for testing in a third Fab system, EP6b_B01, by DSF. Thermal stability measurements for this set of 7 designs, were also performed by DSC (as a more precise method of the two) in all three systems, CAT-2200, H3 and EP6b_B01.

These designs were selected for testing based on the following: a) the designs had a minimal number of amino acid substitutions while still exhibiting optimal performance: 83X_85T; or b) the designs performed the best (i.e. demonstrated maximal Tm gain) irrespective of the number of mutations: 83X_85T_105E_106I. As the 83F theme was less effective than the other 83X themes, only the 83F_85T_105E design was selected representing minimal set of mutations for the maximal Tm gain based on the two CAT-2200 and H3 systems data. The selected designs thus included designs 18, 26, 29, 32, 34, 37 and 39, as listed in Table 3.

DSF and DSC measurements were carried out as described in Example 7.

Figure 7:
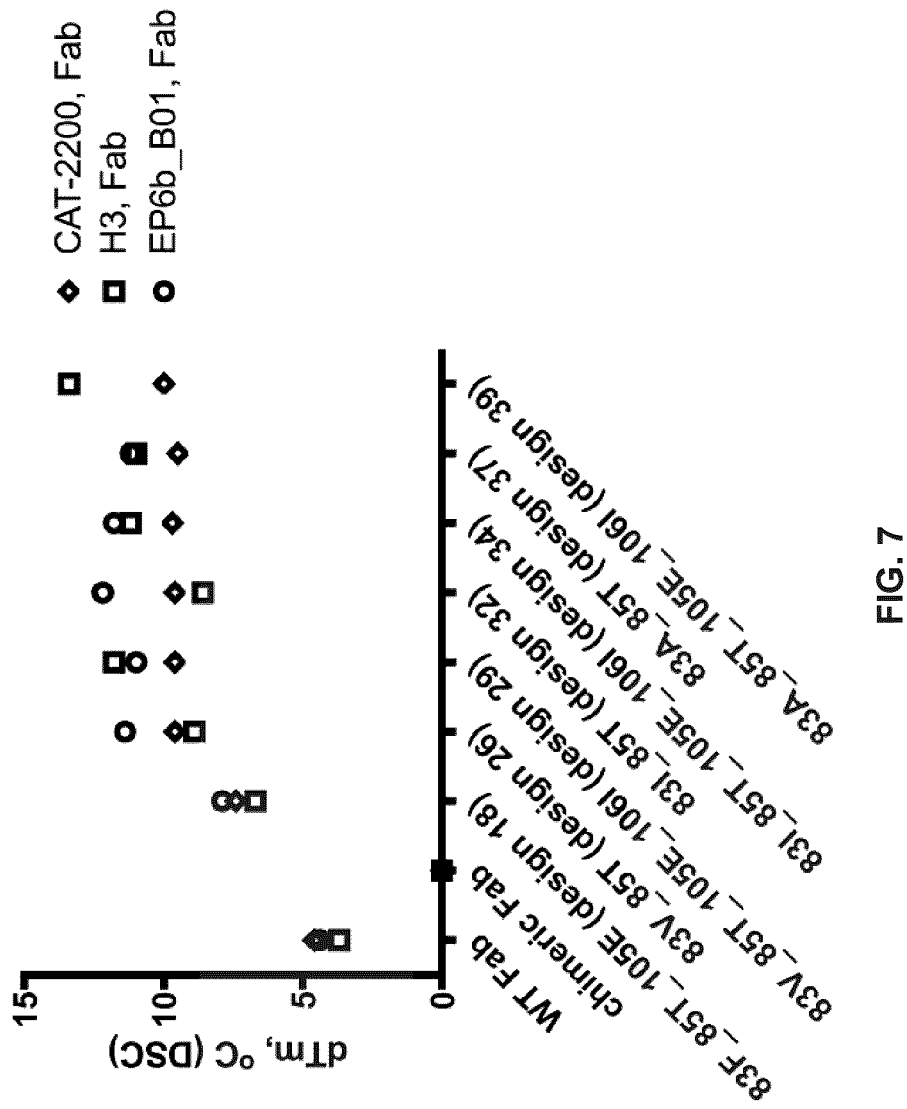
FIG. 7 depicts the extent of the increase in thermal stability across different Fab systems. The change in Tm (measured by DSC) of the designed chimeric Fab compared to that of the respective parent chimeric Fab is plotted for seven selected designs (covering all themes) in three test systems H3, CAT-2200 and EP6b_B01.

The data in Table 4 and FIG. 7 demonstrated that the tested designs transfer into the VL-CK chimeric Fab of a third system, EP6b_B01. Similar trends in the Tm of designs were observed to those observed in the other two systems. As previously noted, system-dependent variations in the extent of the Tm change compared to the starting chimera were observed here as well. Of note is that the Tm values determined by DSC are generally lower than those observed by DSF (described in Example 7), and hence there is a discrepancy in Tm values for the same design when measured by DSC or DSF (as shown in Table 4). However, the relative trends between designs and across systems hold.

Example 9: Transferability of the Effect of Stability Optimization Designs in Mab Format In Examples 7 and 8, the transferability of selected stability optimization designs was demonstrated in the Fab format. In order to test transferability into the Mab format, thermal stability measurements for the set of 7 designs described in Example 8 were performed in two systems, CAT-2200 and H3 by DSC.

Tested Mabs were purified by preparative-SEC as described in Example 5. DSC was performed as described in Example 7. As in Examples 7 and 8, the Tm values for the designed chimeric Mabs were compared to that of the respective chimeric Mab control (chimera) and wild-type lambda Mab (WT). DSC results for the designed chimeric Mabs are reported in Table 5, with Tm values for the two tested systems reported in columns 2 (CAT-2200) and 4 (H3). The change in Tm with respect to the Tm of the respective chimeric Mab is reported in columns 3 (CAT-2200) and 5 (H3).

Figure 8:
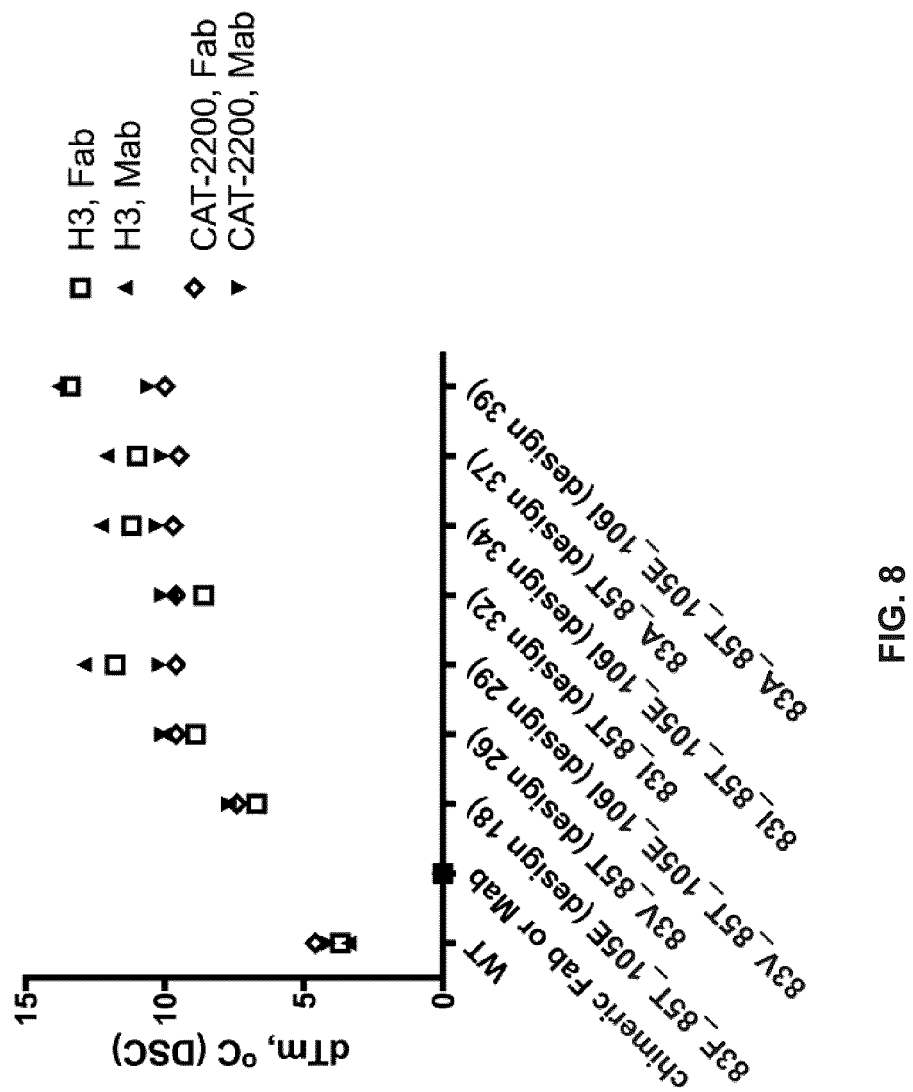
FIG. 8 demonstrates the transferability of the increase in stability from Fab to Mab format. The change in Tm (measured by DSC) of seven selected designed chimeric Fabs and Mabs compared to that of the respective chimeric Fab or Mab, is plotted for two test systems H3 and CAT-2200.
Figure 9A:
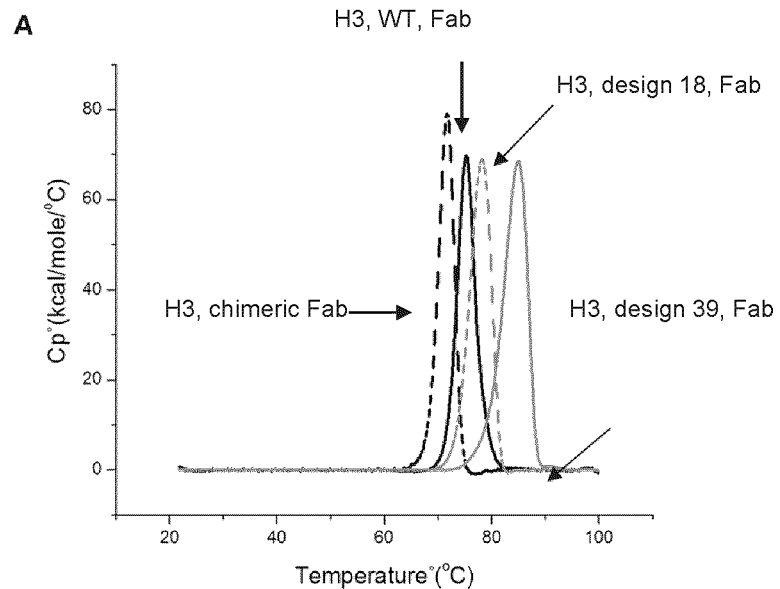
FIG. 9A-9B depicts typical DSC profiles of designed chimeric Fabs (FIG. 9A) and Mabs (FIG. 9B) on a subset of two designs (designs 18 and 39) in the H3 antibody system. The DSC profiles for the respective wild-type and chimeric Fabs and Mabs are included for reference.
Figure 9B:
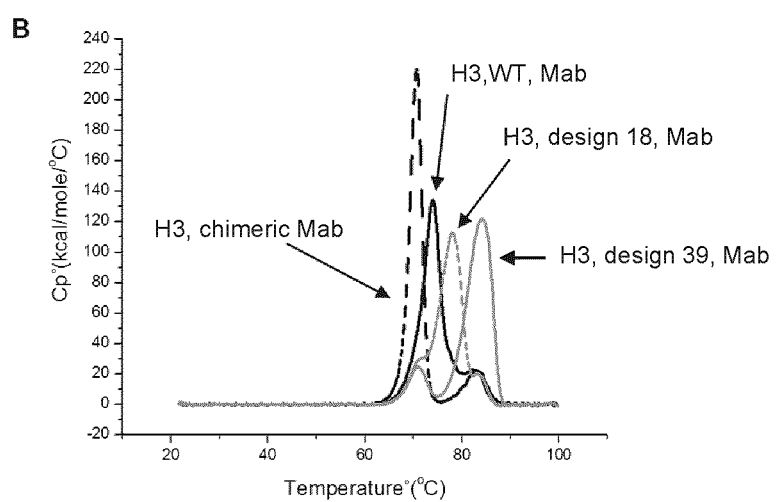
Figure 10A:
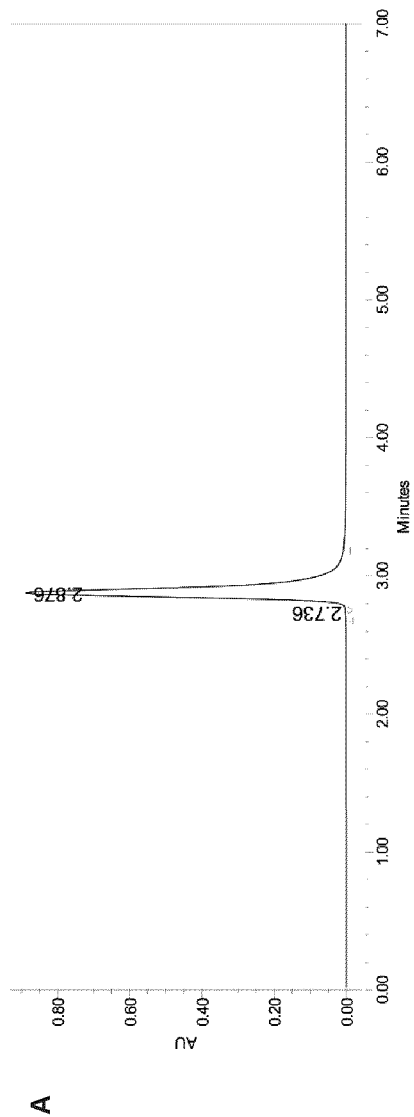
FIG. 10A-10F depicts typical monodisperse UPLC-SEC profiles of designed chimeric Mabs based on the H3 system, at different time points of the benchtop stability study. This study was carried out at 37° C. and at a concentration of 5 mg/ml in PBS buffer pH 7.4.
Figure 10B:
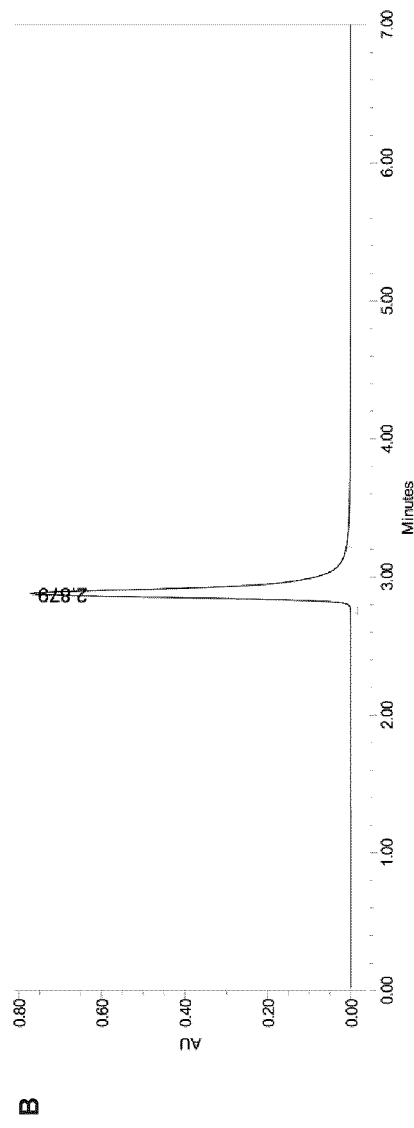
Figure 10C:
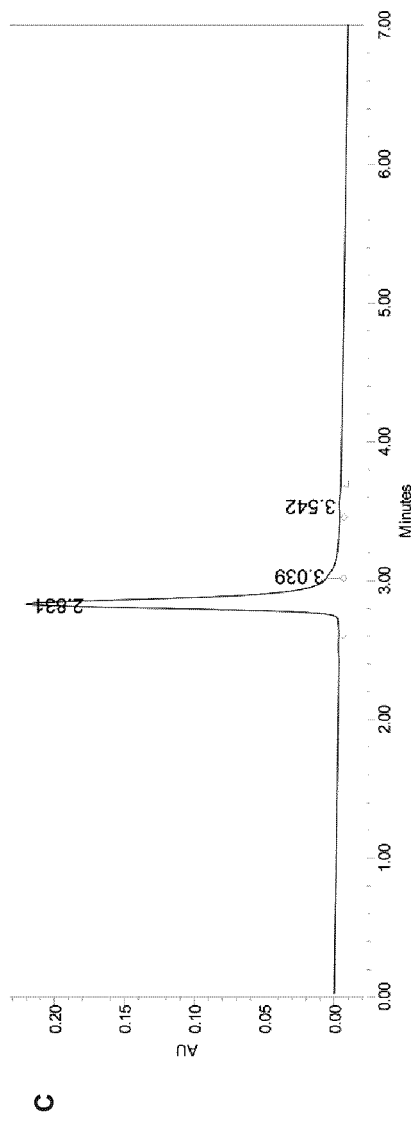
Figure 10D:
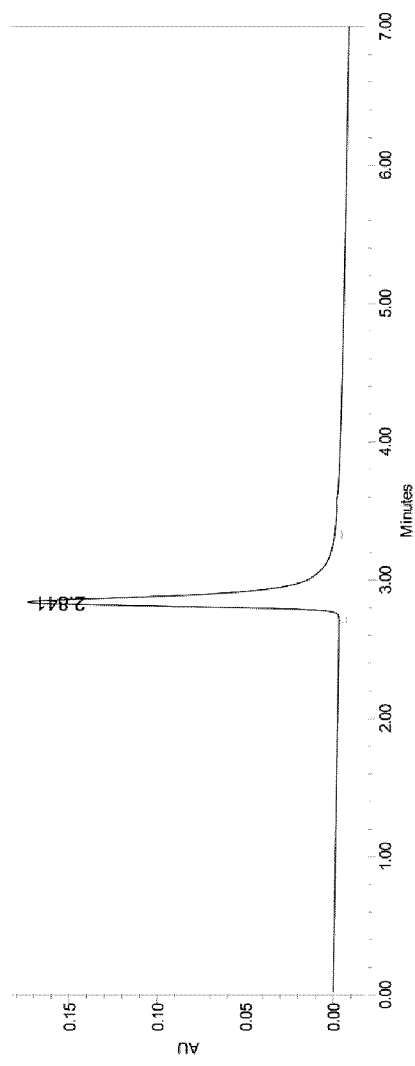
Figure 10E:
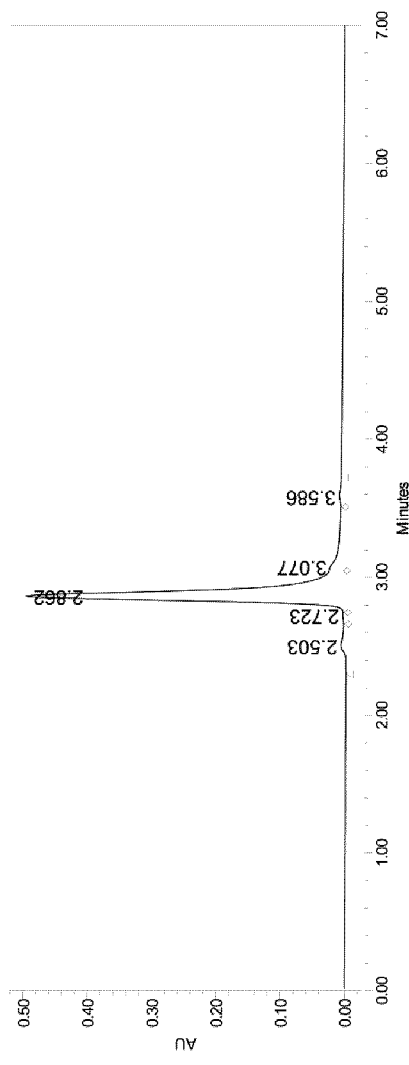
Figure 10F:
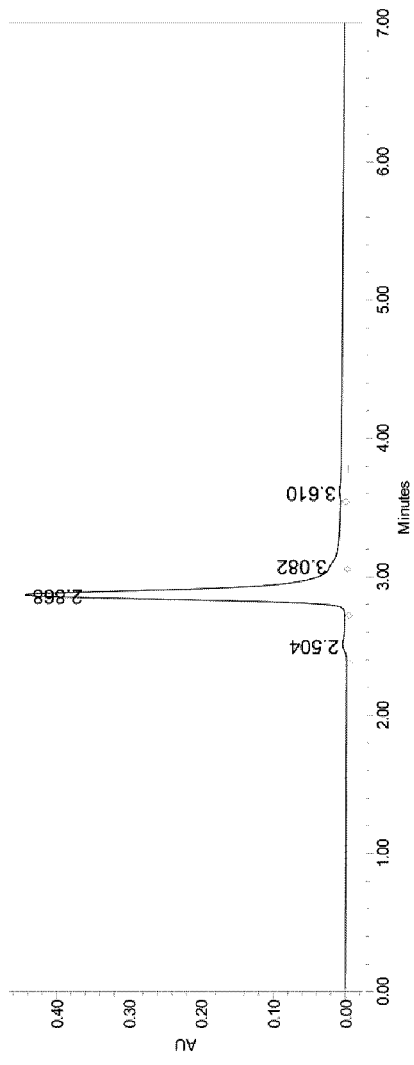

All of the 7 selected designs were able to increase the Tm of the designed chimeric Mabs compared to the respective chimeric Mab, as shown in Table 5. FIG. 8 provides a comparison of the Tm values obtained for designed chimeric Fabs and Mabs in the two systems tested. Identical trends between designs, as far as very similar Tm values, were observed for the tested designs in Fab and Mab formats. Typical DSC thermograms obtained for designed chimeric Fabs (single transition) and designed chimeric Mabs (single prominent Fab transition and CH2 or/and CH3 transitions are observed where not masked by Fab transition) are provided in FIG. 9. These thermograms showed the expected transitions.

The results shown in Examples 7, 8 and 9, demonstrate the transferability of the stability optimization designs across systems and antibody formats.

Example 10: Antigen-Binding Affinity Measurements of Designed Chimeric Fabs and Designed Chimeric Mabs The ability of the designed chimeric Fabs (designed chimeric Fabs of E83X themes, bearing designs 14 to 39) and designed chimeric Mabs (bearing designs 18, 26, 29, 32, 34, 37, and 39, the same 7 designed chimeric Mabs tested in the Examples 8 and 9) to bind the appropriate antigens was assessed in order to determine whether the amino acid substitutions of the stability optimization designs had any effect on antigen-binding affinity. The designed chimeric Fabs and Mabs were purified as described in Example 5. The antigen-binding affinity was determined by SPR in the CAT-2200, H3, and EP6b_B01 systems for designed chimeric Fabs and in the CAT-2200 and H3 systems for designed chimeric Mabs, as follows.

SPR Biosensor Assays

For studies on surface plasmon resonance system (Biacore™ T200): CM5 Series S sensor chip, Biacore™ amine coupling kit (NHS, EDC and 1 M ethanolamine), and 10 mM sodium acetate buffers were purchased from GE Healthcare Life Science (Mississauga, ON, Canada). For studies on Biorad ProteOn™: GLC sensorchips, the Biorad ProteOn™ amine coupling kit (EDC, sNHS and ethanolamine), and 10 mM sodium acetate buffers were purchased from Bio-Rad Laboratories (Canada) Ltd. (Mississauga, ON). PBS running buffer with 0.05% Tween® 20 (PBST) was purchased from Teknova Inc. (Hollister, CA). Goat polyclonal anti-human Fc antibody was purchased from Jackson Immuno Research Laboratories Inc. (West Grove, PA). Antigens: recombinant human HER3 was purchased from ACRObiosystems (Newark,DE), recombinant human sFas receptor was purchased from Pepro Tech Inc. (Rocky Hill, NJ) and recombinant human IL-17A was purchased from R&D Systems (Mineapolis, MN).

Surface plasmon resonance (SPR) assays with antigens HER3 (Fabs) and Fas were carried out using a Biacore™ T200 instrument (GE Healthcare) with PBS-T (PBS+0.05% (v/v) Tween® 20) running buffer (with 0.5 M EDTA stock solution added to 3.4 mM final concentration) at a temperature of 25° C. Surface plasmon resonance assays with IL-17 and HER3 (Mabs) antigens were carried out using BioRad ProteOn™ XPR36 instrument (Bio-Rad Laboratories (Canada) Ltd. (Mississauga, ON)) with PBST running buffer at a temperature of 25° C.

H3: HER3 Affinity Determination in Fabs

HER3 affinity determination in Fabs was carried out as follows. The screening of Fabs (preparative SEC purified) for binding to HER3 antigen occurred in two steps: an indirect capture of HER3 onto the anti-His antibody, followed by the injection of five concentrations of Fabs, for kinetic analysis using single cycle kinetics. The anti-His antibody capture surface was prepared on a CM5 Series S sensor chip by amine coupling approximately 10000 RUs of anti-His antibody (GE Healthcare) onto the active and reference flow cells, according to the manufacturer's instructions. HER3 was injected at 4-8 µg/mL over the active flow cell for 60 s at a flow rate of 10 µL/min. In general, this resulted in the capture of approximately 100-200 RUs of HER3 onto the anti-His antibody surface. HER3 was not captured on the reference (blank) flow cell. The capture step was followed by five concentrations of Fabs (200 nM and 2-fold dilutions) that were sequentially injected over both the active and reference flow cells at 50 µL/min for 90 s with a dissociation phase of 300 s. The captured HER3 surfaces were regenerated by 10 mM glycine pH 1.5 for 120 s at 30 µL/min to prepare the surfaces for the next injection cycle. At least two mock-buffer injections were performed for each analyte injection and used for referencing. The resulting single cycle kinetics sensorgrams were analyzed using Biacore™ T200 BiaEvaluation software version 3.0 and fit to the 1:1 binding model.

H3:HER3 Affinity Determination in Mabs

HER3 affinity determination in Mabs was carried out as follows. The screening of Mabs for binding to HER3 antigen occurred in two steps: an indirect capture of Mabs onto the anti-human Fc-specific polyclonal antibody surface, followed by the injection of five concentrations of HER3. The anti-human Fc surface was prepared on a GLC sensorchip by amine coupling. GLC sensorchip surface was activated by a 1:10 dilution of the standard BioRad sNHS/EDC solutions injected for 140 s at 100 1.1 L/min in the analyte (horizontal) direction. Immediately after the activation, 25 microg/mL solution of anti-human Fc in 10 mM NaOAc pH 4.5 was injected in the ligand (vertical) direction at a flow rate of 25 microL/min for 240 s until approximately 3000 resonance units (RUs) were immobilized. Remaining active groups were quenched by a 140 s injection of 1M ethanolamine at 100 µL/min also in the analyte direction. Mabs for analysis were indirectly captured onto the anti-Fc surface by injecting 20 microg/mL solutions in the ligand (vertical) direction at a flow rate of 25 microL/min for 240 s. HER3 was subsequently injected in the analyte (horizontal) direction. Firstly, two buffer injections for 30 s at 100 microL/min in the analyte (horizontal) direction were used to stabilize the baseline. Five concentrations of a three-fold dilution series of each H3 Mab starting at 180 nM with a blank buffer control were then simultaneously injected at 25 microL/min for 120 s with a 10 minute dissociation phase, resulting in a set of binding sensorgrams with a buffer reference. The anti-human Fc surfaces were regenerated to prepare for the next injection cycle by two pulses of 0.85% phosphoric acid for 18 s at 100 microL/min. Sensorgrams were aligned and double-referenced using the buffer blank injection and interspots, and the resulting sensorgrams were analyzed using ProteOn™ Manager™ software v3.1. The double-referenced sensorgrams were fit to the Langmuir binding model.

EP6b_B01: Fas Affinity Determination

Fas affinity determination was carried out as follows. Fas was diluted in 10 mM acetate buffer pH 5.5 and directly immobilized via amine coupling onto a CM5 Series S sensor chip. This resulted in approximately 100 RUs of immobilized Fas. The reference flow cell was left empty (ethanolamine blocked) to use as a blank control. Fabs were injected over both the ethanolamine-blocked reference surface and the Fas surface for kinetic analysis using single cycle kinetics. Specifically, five concentrations (5 nM and 2-fold dilutions) of purified Fabs (preparative SEC purified) were sequentially injected over both the active and reference flow cells at 30 µL/min for 600 s with a dissociation phase of 3600 s. Fas surfaces were regenerated using 2 cycles of 10 mM glycine pH 1.5 for 120 s at 30 µL/min to prepare the surfaces for the next injection cycle. At least two mock-buffer injections were performed for each analyte injection to be used for referencing. The resulting single cycle kinetics sensorgrams were analyzed using Biacore™ T200 BiaEvaluation software version 3.0 and fit to the 1:1 binding model.

CAT-2200:IL-17 Affinity Determination

IL-17 affinity determination was carried out as follows. The IL-17A surface was generated using a GLC sensorchip activated by a 1:10 dilution of the standard BioRad sNHS/EDC solutions injected for 140 s at 100 µL/min in the ligand (vertical) direction. Immediately after the activation, 1 to 4 microg/mL solution of IL-17A in 10 mM NaOAc pH 4.5 was injected in the ligand (vertical) direction at a flow rate of 25 or 100 microL/min until approximately 75-200 resonance units (RUs) were immobilized. Remaining active groups were quenched by a 140 s injection of 1M ethanolamine at 100 µL/min also in the ligand direction. The screening of the Fabs/Mabs for binding to IL-17A was performed by injection of purified CAT-2200 Fabs/Mabs in the analyte (horizontal) direction. Firstly, two buffer injections for 30 s at 100 microL/min in the analyte (horizontal) direction were used to stabilize the baseline. Five concentrations of a three-fold dilution series of each CAT-2200 Fab/Mab (60 nM, 20 nM, 6.7 nM, 2.2 nM, 0.74 nM) with a blank buffer control were simultaneously injected at 50 microL/min for 120 s with a 10 or 15 minute dissociation phase, resulting in a set of binding sensorgrams with a buffer reference. CAT-2200:IL-17A complexes on the SPR surface are dissociated and the IL-17A surface regenerated to prepare for the next injection cycle by two pulses of 0.85% phosphoric acid for 18 s at 100 microL/min. Sensorgrams were aligned and double-referenced using the buffer blank injection and interspots, and the resulting sensorgrams were analyzed using ProteOn™ Manager™ software v3.1. The double-referenced sensorgrams were fit to the Langmuir binding model.

Results

For designed chimeric Fabs/Mabs where repeats were conducted, the reported KD value is the mean value.

Antigen-binding affinities of the designed chimeric Fabs were assessed with reference to the respective wild-type lambda Fab and chimeric Fab. SPR results for designed chimeric Fabs are reported in Table 6, where the determined KD values for the three tested systems are reported in columns 2, (CAT-2200), 3 (H3) and 4 (EP6b_B01). In all systems tested, the antigen-binding affinity of the chimeric Fab control (chimera) was very similar to the wild-type lambda Fab control (WT). The data in Table 6 shows that the antigen-binding affinity of the designed chimeric Fabs based on the CAT-2200 parent antibody was within about 2-fold that of the wild-type lambda Fab and of the chimeric Fab. The antigen-binding affinity of the designed chimeric Fabs based on the H3 parent antibody was also within about 2-fold that of the wild-type lambda Fab and of the chimeric Fab. Although fewer designed chimeric Fabs were tested in the EP6bB01 system, the same trend was observed.

Antigen-binding affinities of the designed chimeric Mabs were assessed with reference to the respective wild-type lambda Mab and chimeric Mab. SPR results for designed chimeric Mabs are reported in Table 7, where the KD values for the two tested systems are reported in columns 2 (CAT-2200) and 3 (H3). In both systems tested, the antigen-binding affinities of the wild-type lambda Mab control (WT) and corresponding chimeric Mab control were within 1.5 fold of each other. The designed chimeric Mabs were able to bind antigen with a KD very similar to the controls above.

As can be seen from Tables 6 and 7, designed chimeric Mabs or Fabs bearing amino acid substitutions corresponding to stability optimization designs were able to bind to antigen with KD values comparable to those of wild-type lambda Fabs and Mabs respectively.

Example 11: Effect of Stability Optimization Designs on FcγR Binding

Wild-type IgG1 antibodies are able to bind to Fc gamma R receptors (FcγR) to mediate effector functions such as ADCC and ADCP. In order to determine whether the amino acid substitutions of the stability optimization designs would have any effect on the ability of designed chimeric Mabs to bind to FcγR, the affinity of a selected set of designed chimeric Mabs (bearing designs 29, 37 and 39) for FcγR was measured. Binding affinities of designed chimeric Mabs to four different types of FcγR receptors, CD16aV, CD32bF, CD32aR, and CD32aH were assessed. The designed chimeric Mabs were purified as described in Example 5. The binding affinities were determined by SPR as follows.

Surface plasmon resonance assays were carried out using BioRad ProteOn™ XPR36 instrument (Bio-Rad Laboratories (Canada) Ltd. (Mississauga, ON)) with PBST running buffer at a temperature of 25C. GLC sensorchips, the Biorad ProteOn™ amine coupling kit (EDC, sNHS and ethanolamine), and 10 mM sodium acetate buffers were purchased from Bio-Rad Laboratories (Canada) Ltd. (Mississauga, ON). PBS running buffer with 0.05% Tween® 20 (PBST) was purchased from Teknova Inc. (Hollister, CA). Goat polyclonal anti-human Fc antibody was purchased from Jackson Immuno Research Laboratories Inc. (West Grove, PA). Antigens: human recombinant FcRn was produced in house. Human recombinant FcγR receptors: CD16aV, CD32bF, CD32aR, and CD32aH were expressed as constructs containing a His10-tag at the C-terminus and purified by Ni-affinity chromatography followed by His-tag removal and SEC purification.

Mab: FcγR Affinity Determination

FcγR affinity determination was carried out as follows. The screening of Mabs for binding to various FcγR receptors occurred in two steps: an indirect capture of Mab samples onto the anti-human Fc-specific polyclonal antibody surface, followed by the injection of five concentrations of each of FcγR receptors. The anti-human Fc surface was prepared on a GLC sensorchip by amine coupling. GLC sensorchip surface was activated by a 1:10 dilution of the standard BioRad sNHS/EDC solutions injected for 140 s at 100 µL/min in the analyte (horizontal) direction. Immediately after the activation, 25 microg/mL solution of anti-human Fc in 10 mM NaOAc pH 4.5 was injected in the analyte direction at a flow rate of 25 microL/min for 240 s until approximately 4500 or 2500 resonance units (RUs) were immobilized. Remaining active groups were quenched by a 300 s injection of 1M ethanolamine at 301.1 L/min also in the analyte direction. Mabs for analysis were indirectly captured onto the anti-human Fc surface by injecting 10 microg/ml solutions in the ligand (vertical) direction at a flow rate of 25 microL/min for 240 s. Each of the FcγR receptors was subsequently injected in the analyte (horizontal) direction. Firstly, two buffer injections for 30 s at 100 microL/min in the analyte (horizontal) direction were used to stabilize the baseline. Five concentrations of a three-fold dilution series of each of the four FcγR receptors starting at 101.1M with a blank buffer control were then simultaneously injected at 50 microL/min for 120 s with a 3 minute dissociation phase, resulting in a set of binding sensorgrams with a buffer reference. The anti-human Fc surfaces were regenerated to prepare for the next injection cycle by two pulses of 0.85% phosphoric acid for 18 s at 100 microL/min. Sensorgrams were aligned and double-referenced using the buffer blank injection and interspots, and the resulting sensorgrams were analyzed using ProteOn™ Manager™ software v3.1. The double-referenced sensorgrams were fit to the Langmuir binding model or were fit to the equilibrium binding model for steady-state KD determination.

Results

Table 8 shows the SPR results for designed chimeric Mabs in two systems (CAT-2200 and H3). Determined KD values for binding to the CD16aV receptor are reported in column 2, for CD32bF in column 3, for CD32aR in column 4, for CD32aH in column 5. For tested designed chimeric Mabs where repeats were conducted, the reported KD value is the mean value As can be seen from Table 8, the KD values measured for the designed chimeric Mabs were comparable to those for the respective wild-type lambda Mab controls (WT) for the FcγR receptors tested.

Example 12: Effect of Stability Optimization Designs on FcRn Binding

Wild-type IgG1 antibodies are able to bind to FcRn receptors (neonatal receptors) resulting in their long half-life. In order to determine whether the amino acid substitutions of the stability optimization designs had any effect on the ability of the designed chimeric Mabs to bind to FcRn, the affinity of a selected set of designed chimeric Mabs (bearing designs 29, 37 and 39) for FcRn was measured. The designed chimeric Mabs were purified as described in Example 5 and the binding affinities were determined by SPR as follows.

Mab: FcRn Affinity Determination

FcRn affinity determination was carried out as follows. FcRn surface was generated using a GLC sensorchip activated by a 1:10 dilution of the standard BioRad sNHS/EDC solutions injected for 140 s at 100 µL/min in the ligand (vertical) direction. Immediately after the activation, 10 microg/mL solution of FcRn in 10 mM NaOAc pH 4.5 was injected in the ligand (vertical) direction at a flow rate of 25 microL/min for 120 s until approximately 2000 resonance units (RUs) were immobilized. Remaining active groups were quenched by a 140 s injection of 1M ethanolamine at 30 µL/min also in the ligand direction. The running buffer used on the FcRn surface was PBST pH 5.8. The screening of the Mabs for binding to FcRn was performed by injection of purified Mabs in the analyte (horizontal) direction. Firstly, two buffer injections for 30 s at 100 microL/min in the analyte (horizontal) direction were used to stabilize the baseline. Five concentrations of a three-fold dilution series of each Mab starting at 100 nM with a blank buffer control were simultaneously injected at 50 microL/min for 120 s with a 10 minute dissociation phase, resulting in a set of binding sensorgrams with a buffer reference. Mab:FcRn complexes on the SPR surface are dissociated and the FcRn surface regenerated to prepare for the next injection cycle by two pulses of PBST pH 7.4, for 18 s at 100 microL/min. Sensorgrams were aligned and double-referenced using the buffer blank injection and interspots, and the resulting sensorgrams were analyzed using ProteOn™ Manager™ software v3.1. The double-referenced sensorgrams were fit to the Langmuir binding model.

Table 8 shows the SPR results for designed chimeric Mabs in two systems (CAT-2200 and H3). Determined KD values for binding to FcRn are reported in column 6. For tested designed chimeric Mabs where repeats were conducted, the reported KD value is the mean value. As can be seen from Table 8, the binding affinity of tested designed chimeric Mabs, both CAT-2200 and H3, for FcRn is within 1.5 to 2-fold that of respective wild-type lambda Mab controls (WT).

Example 13: Effect of Stability Optimization Designs on Benchtop Stability of Selected Designed Chimeric Mabs The stability of designed chimeric Mabs over time was measured for designed chimeric Mabs bearing stability optimization designs 29, 37 and 39, as described below. Designed chimeric Mabs were tested based on the CAT-2200 and H3 parent antibodies.

The designed chimeric Mabs were concentrated to 5 mg/ml in PBS pH7.4 and incubated at 37° C. for 30 days. Samples were taken at 0, 6, 10, 20 and 30 day time points. Each sample was centrifuged and the supernatant assessed by UPLC-SEC and Caliper analysis. UPLC-SEC and Caliper analysis of samples at days 0, 6, 10, 20 and 30 was performed as well as protein quantitation by A280 nm using a spectrophotometer (NanoDrop™) in order to assess any changes to the monodispersity of the samples. UPLC-SEC was carried out as described in Example 6.

FIG. 10 depicts typical UPLC-SEC profiles observed at days 0, 20 and 30 of incubation at 37° C. for these designed chimeric Mabs, on an example of H3 wild-type lambda Mab and an H3 designed chimeric Mab with amino acid substitutions corresponding to design 37. Panels A and B contrast UPLC-SEC profiles at days 0, panels C and D at day 20 and E and F at day 30, for wild-type lambda Mab control and design 37 in H3 system, respectively. The UPLC-SEC profiles observed demonstrated the absence of any change in the monodispersity of Mab molecules during the incubation period. Measurement of protein concentration reflected no loss of protein to any potential aggregation (data not provided).

Example 14: Assessment of Preferential Pairing Between Heavy and Light Chains in Designed Chimeric Bispecific Antibodies Chimeric light chains can be useful in the preparation of bispecific antibodies, particularly in cases where one or both parent antibodies have a lambda light chain. This example describes the use of stability optimization designs to prepare bispecific antibodies where one parent antibody of the bispecific antibody has a lambda light chain.

The stability optimization designs used were those corresponding to designs 29 and 39, described in Table 3. Two bispecific antibody systems were tested. The first was a CAT-2200/D3H44 bispecific antibody, where the CAT-2200 parent antibody has a lambda light chain and the D3H44 antibody has a kappa light chain. The second system was an H3/pertuzumab bispecific antibody, where the H3 antibody has a lambda light chain and the pertuzumab antibody has a kappa light chain. CAT-2200 and H3 are human antibodies, while pertuzumab and D3H44 are humanized antibodies. In these system, the light chains of the CAT-2200 and H3 antibodies were constructed as VL-CK chimeric light chains as described in Example 3.

Figure 11:
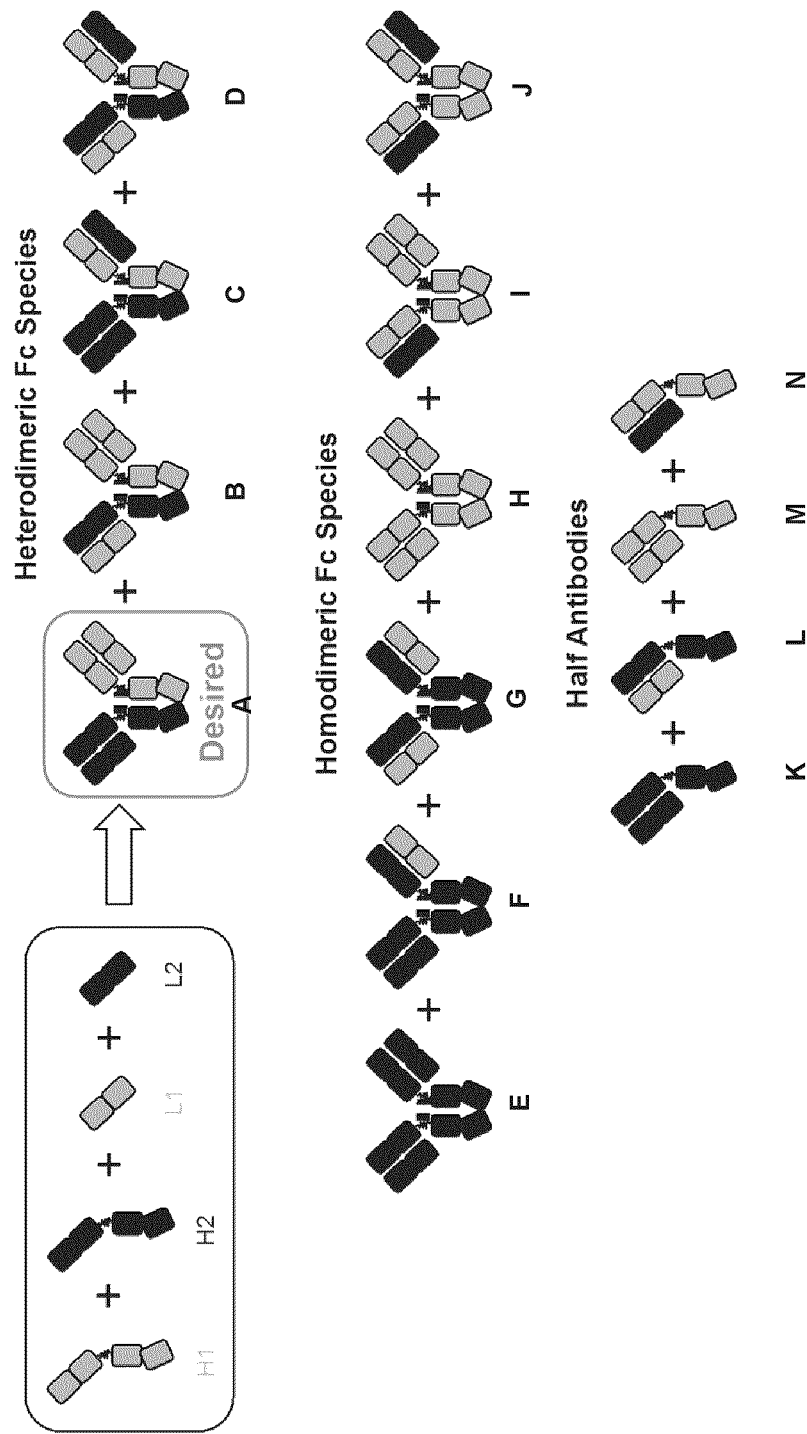
FIG. 11 depicts the potential heavy chain-associated products that can be expected when two different light chains are co-expressed with two different heavy chains in a cell. Preferential pairing is assessed using an SMCA (monoclonal antibody competition assay).

The bispecific antibodies were prepared using amino acid substitutions in the Fab regions (light chain pairing designs) of the parent antibodies to drive pairing. Such amino acid substitutions are known in the art and described in a number of publications, including International Patent Publication Nos. WO 2014/082179 and WO 2015/181805. Two such designs were tested in this example, as shown in Table A2 below:

H1L1_H2L1, H1L2_H2L2, H1L2_H2L1 and H1L1_H2L2. The H1L1_H2L2 species is the correctly paired bispecific antibody (FIG. 11, species A). Four types of half-antibody (half-Ab) species are also possible, as shown in FIG. 11. When modifications are introduced into the Fc region to promote heterodimerization of the unique heavy chains, the number of potential antibody species decreases (i.e. less of species E to J are observed). The relative pairing specificity in terms of amount of correctly paired bispecific antibody species H1L1_H2L2 vs. other species was determined using LC-MS after protein A (pA) purification and deglycosylation. When possible, chains were left untagged, provided that all antibody species and half-Ab species differed from each other by at least 50 Da. When mass differences precluded this possibility, N-terminal FLAG tag was added to the light chains in order to provide sufficient mass differentiation between species.

TABLE A

Kappa-kappa light chain pairing designs (amino acid numbering according to Kabat)

| Design | Antibody 1 | | Antibody 2 | |
|---|---|---|---|---|
| | H1 | L1 | H2 | L2 |
| 9060-9756 | A139W_L143E_K145T_Q179E | F116A_Q124R_L135V_T178R | Q179K | Q124E_L135W_Q160E_T180E |
| 9820-9823 | Q39R_H172R_Q179K | Q38E_Q124E_Q160E_T180E | Q39E_L143E_K145T_Q179E | Q38R_Q124R_Q160K_T178R |

Amino acid substitutions were also introduced into the CH3 domains of the heavy chains in order to promote heterodimerization of the heavy chains (heavy chain pairing designs). These amino acid substitutions have also been described in the art, including in International Patent Publication Nos. WO 2012/058768 and WO2013/063702. One exemplary design was tested in this example, as shown in Table B1 below:

TABLE B

Heavy chain pairing designs (amino acid positions numbered according to the EU numbering system)

| Heavy Chain A | T350V | L351Y | F405A | Y407V |
| Heavy Chain B | T350V | T366L | K392L | T394W |

The four polypeptide chains of each bispecific antibody were co-expressed and the increase in the amount of desired bispecific antibody determined in the SMCA assay described below.

Assay Format (SMCA)

The assay is based on co-expressing the four chains of the two parent antibodies (the heavy and light chains of parent antibody 1, H1 and L1, respectively, with the heavy and light chains of parent antibody 2, H2 and L2, respectively) and detecting the presence of correctly formed bispecific antibody using mass spectrometry (LC-MS). FIG. 11 provides a schematic depicting the four starting polypeptide chains and the potential products resulting from co-expression of these starting polypeptide chains in the absence of preferential pairing between heavy and light chains (in both Fab and Fc regions) of the heterodimer pairs. Two unique full-length heavy chain constructs were co-expressed with two unique light chain constructs, yielding ten possible antibody species (also referred to as Ab species): H1L1_H1L1, H1L2_H1L2, H1L1_H1L2, H2L1_H2L1, H2L2_H2L2, H2L1_H2L2, Polypeptide Sequences The protein sequences of the CAT-2200 and H3 heavy chains and VL-CK chimeric light chains were obtained as described in Example 3.

The protein sequences of the D3H44 light chain (SEQ ID NO:13) and heavy chain (SEQ ID NO:12) corresponded to those in the PDB entry 1JPT, and were reverse translated to DNA, codon optimized for mammalian expression, and gene synthesized (SEQ ID NO:28 and 27, respectively). The protein sequences of the pertuzumab light chain (GenBank Accession No. HC359025.1, SEQ ID NO:11) and heavy chain (GenBank Accession No. HC359024.1, SEQ ID NO:10) were reverse translated to DNA, codon optimized for mammalian expression, and gene synthesized (SEQ ID NOs: 26 and 25, respectively). The polypeptide and DNA sequences of these antibody heavy and light chains are shown in Table 2.

The following sets of bispecific chimeric antibody control constructs were prepared to assess the amount of light chain pairing intrinsic to each bispecific system.

A. A set of constructs encoding the control H3/pertuzumab chimeric bispecific antibody were prepared (corresponding to bispecific antibody (1) in Table 9):

A construct encoding full-length H3 heavy chain (H1) including the heavy chain pairing designs for chain A or B, and a construct encoding the H3 VL-CK chimeric light chain (L1).

A construct encoding full-length pertuzumab heavy chain (H2), with heavy chain pairing designs for the complementary chain to H1, and a construct encoding the pertuzumab kappa light chain (L2).

B. A set of constructs encoding the control CAT-2200/D3H44 chimeric bispecific antibody were prepared (corresponding to bispecific antibodies (2) and (3) in Table 9):

A construct encoding full-length CAT-2200 heavy chain (H1) including the heavy chain pairing designs for chain A or B, and a construct encoding the CAT-2200 VL-CK chimeric light chain (L1).

A construct encoding full-length D3H44 heavy chain (H2), with heavy chain pairing designs for the complementary chain to H1, and a construct encoding the D3H44 kappa light chain (L2).

The following additional constructs were prepared based on the bispecific chimeric antibody controls described above:

a. Stability optimization design controls—these constructs are similar to the bispecific chimeric antibody controls, but include a stability optimization design. These controls correspond to bispecific antibodies (4) to (7) in Table 9.

b. designed bispecific chimeric antibodies—these constructs are similar to the bispecific chimeric antibody controls, but include a stability optimization design and a light chain pairing design. These constructs correspond to bispecific antibodies (8) to (15) in Table 9.

Figure 12:
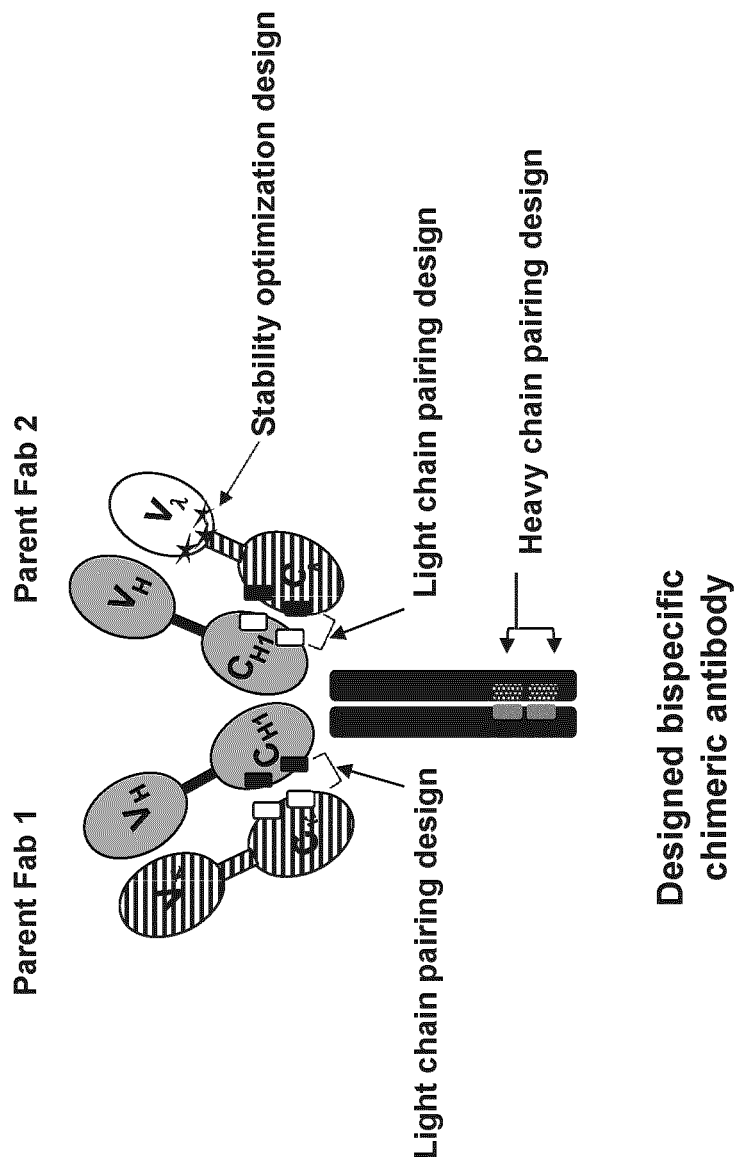
FIG. 12 depicts a schematic representation of an exemplary designed bispecific chimeric antibody composed of the parental Fab 1 (kappa Fab) and parental Fab 2 (designed Vlambda-Ckappa chimeric Fab), where star symbols denote stability optimization designs and rectangular symbols denote light chain pairing designs or heavy chain pairing designs.

FIG. 12 provides a representative bispecific chimeric antibody structure, showing the different types of modifications included in a designed bispecific chimeric antibody.

Constructs encoding the CAT-2200 and H3 Vlambda-Ckappa chimeric light chains, D3H44 and pertuzumab kappa light chains and respective IgG heavy chains, comprising amino acid modifications according to the designs were prepared as follows. The CAT-2200, H3, D3H44 and pertuzumab light chain sequences were prepared as described in Example 3 with amino acid modifications according to the stability optimization design and/or the kappa-kappa light chain pairing design for promoting heterodimerization of light chains. The full-length heavy chain sequences for these antibodies were created as described in Example 3 with amino acid modifications to promote heterodimerization of the heavy chains. Of note, the canonical C-terminal heavy chain lysine residue was removed in order to prevent LC-MS signal heterogeneity due to C-terminal lysine clipping (Lawrence W. Dick Jr. et al., Biotechnol. Bioeng. (2008) 100:1132-43). In some cases, a FLAG tag was added to the light chain in order to attain 50 Da difference between all antibody and half-Ab species, in which case the light chain vector inserts consisted of a 5'-EcoRI cutsite—HLA-A signal peptide—FLAG tag—Light chain Ig clone—'TGA or TAA stop'—BamH1 cut site-3'.

Chimeric bispecific antibodies with stability optimization designs only were also prepared in order to be able to assess whether such designs have any effect on the preferential pairing exerted by the introduced light chain pairing design.

Transfection, Expression and Purification of Bispecific Chimeric Antibody Constructs Constructs encoding the two heavy chains and two light chains of each bispecific antibody system, in which light chain sets are either Vlambda-Ckappa chimera light chain and kappa light chain, or Vlambda-Ckappa chimera light chain with stability optimization design and kappa light chain with or without introduced kappa-kappa design, were transfected into CHO-3E7 cells as previously described in Example 4, where a total volume of 50 ml was transfected with a total of 50 µg DNA at 15:15:35:35 ratio of H1:H2:L1:L2.

Culture media was harvested by centrifugation and vacuum filtered using a Stericup® 0.22 µm filter (Millipore Cat #SCGPU05RE). The filtered culture media was then purified using protein A MabSelect™ SuRe™ resin (GE Healthcare #17-5438-02) that was previously equilibrated with PBS pH 7.4. The antibody species bound to the resin were then washed with PBS pH 7.4 and eluted with 100 mM sodium citrate buffer pH 3.6. Eluted antibody species were concentrated and buffer exchanged in PBS pH 7.4 by centrifugation using Amicon® ultra 15 centrifuge filter Ultracel 10K (Millipore #UFC901024). Part of the expressed bispecific antibody samples was alternatively purified according to the procedure described in Example 3 for the Mab construct purification (batch mode). The resulting protein A-purified SMCA samples containing the antibody species were assessed by Caliper prior to deglycosylation and LC-MS.

Mass Spectrometry Method

The degree of preferential pairing of heterodimers driven by the kappa-kappa designs in the context of a bispecific antibody was assessed using mass spectrometry after protein A purification and non-denaturating deglycosylation. As the bispecific antibody contained Fc N-linked glycans only, the SMCA samples were treated with only one enzyme, N-glycosidase F (PNGase-F). The purified samples were deglycosylated with PNGaseF as follows: 0.2U PNGaseF/µg of antibody in 50 mM 2-amino-2-(hydroxymethyl)propane-1,3-diol (Tris)-HCl pH 7.0, overnight incubation at 37° C., final protein concentration of 0.5 mg/mL. After deglycosylation, the samples were stored at 4° C. prior to LC-MS analysis.

The deglycosylated protein samples were analyzed by intact LC-MS using an Agilent 1100 HPLC system coupled to an LTQ-Orbitrap™ XL mass spectrometer (ThermoFisher Scientific) via an Ion Max electrospray source (ThermoFisher). The samples (5 µg) were injected onto a 2.1×30 mm Poros™ R2 reverse phase column (Applied Biosystems) and resolved using the following gradient conditions: 0-3 min: 20% solvent B; 3-6 min: 20-90% solvent B; 6-7 min: 90-20% Solvent B; 7-9 min: 20% solvent B. Solvent A was degassed 0.1% formic acid aq. and solvent B was degassed acetonitrile. The flow rate was 3 mL/min. The flow was split post-column to direct 100 µL/mL into the electrospray interface. The column was heated to 82.5° C. and solvents were heated pre-column to 80° C. to improve protein peak shape. Prior to analysis, the LTQ-Orbitrap™ XL was calibrated using ThermoFisher Scientific's LTQ Positive Ion ESI calibration solution (caffeine, MRFA and Ultramark 1621), and tuned using a 10 mg/mL solutions of CsI. The cone voltage (source fragmentation) was approximately 48 V, the FT resolution was 7,500 and the scan range was m/z 400-4,000. The LTQ-Orbitrap™ XL was tuned for optimal detection of larger proteins (>50 kDa). The LC-MS system was evaluated for IgG sample analysis using a deglycosylated IgG standard (Waters™ IgG standard) as well as a deglycosyated mAb standard mix (25:75 half:full sized mAb).

The ranges containing the multiply charged ions from the full-sized antibodies and the half-antibodies (typically m/z 2000-3800 and m/z 1400-2000, respectively) were separately deconvoluted into molecular weight profiles using MaxEnt 1 module of MassLynx, the instrument control and data analysis software (Waters™). Briefly, the raw protein LC-MS data were first opened in QualBrowser, the spectrum viewing module of Xcalibur (Thermo Scientific) and converted to be compatible with MassLynx using Databridge, a file conversion program provided by Waters™. The converted protein spectra were viewed in the Spectrum module of MassLynx and deconvoluted using MaxEnt 1. The apparent amount of each antibody species in each sample was determined from their peak heights in the resulting molecular weight profiles.

Results

Overall, in most cases, the deglycosylation treatments resulted in the ability to identify all of the possible different antibody species identified by LC-MS. In many cases, each antibody species was represented by a single LC-MS peak. Exceptions included side peaks that likely also correspond to the desired bispecific species (possibly adducts or heterogeneity in the cleavage of leader peptides); however, because identity of the species resulting in the side peaks was not clear, these side peaks were not considered in the contributions to the bispecific species. The desired bispecific species, H1L1_H2L2, cannot generally be distinguished experimentally from the mispaired type, H1L2_H2L1, on the basis of LC-MS. As such, when bispecific antibody content is reported in the tables, it cannot be completely excluded that it does not contain this type of mispaired species. However, the very low content observed for species such as H1L2_H1L2 and H2L1_H2L1, as well as H1L2 and H2L1 half antibodies is indicative that only minor, if any, contamination of the bispecific species with mispaired species occurred.

LC-MS analysis results are reported in Table 9. In column 8, calculations on the amount of correctly paired bispecific antibody (H1L1_H2L2 and H1L2_H2L1) as a percentage of all antibody species present (FIG. 11 depicts all possible species upon co-expression of four chains: H1, L1 H2, L2, species A-J). In column 6, calculations of the amount of correctly paired bispecific antibody (H1L1_H2L2 and H1L2_H2L1**) as a percentage of all full-size antibody species only are provided, to measure pairing excluding half-antibody species. Comparison of the amount of correctly paired chimeric bispecific antibodies, with stability optimization designs alone or with stability optimization design in combination with kappa-kappa light chain pairing designs (designed chimeric bispecific antibody), to that of the chimeric bispecific antibody control is reported in columns 7 and 9 respectively. In the case of H3/pertuzumab system, the equivalent comparison was not possible, because the FLAG tag was required on the light chain of pertuzumab in order to attain 50 Da difference between all antibody and half-Ab species. For this system, a comparison was performed to a similar construct (i.e. a chimeric bispecific antibody control containing a FLAG tag on the pertuzumab light chain) indicated by '*' next to the values reported. The predominant mispaired species present in the analyzed bispecific samples was H1H2L1L1, the amount of which as a percentage of all antibody species present in the sample is reported in column 10.

In both systems, H3/pertuzumab and CAT-2200/D3H44, bispecific antibody content decreased to a small degree upon introduction of the stability optimization design in the bispecific chimeric antibody (column 9) compared to the bispecific chimeric Ab control. In the H3/pertuzumab and CAT-2200/D3H44 systems, bispecific antibody content of the designed bispecific chimeric antibody, i.e. with a kappa-kappa light chain pairing design along with a stability optimization design, as defined in column 8, was largely comparable across 2 sets of stability optimization designs tested and 2 sets of kappa-kappa light chain pairing designs and was in the range of 64.6-86.4%. This translated into a desired bispecific species content increase compared to that of bispecific chimeric control of 25.3-36% in H3/pertuzumab system and 46.3-80.4% in CAT-2200/D3H44 system (column 9). The specific type of kappa-kappa design (i.e. either design 9060-9756 or 9820-9823) was predominantly responsible for the observed variation (range) of values in the CAT-2200/D3H44 system. A similar range of improvement in bispecific content of these designs, as indicated in column 7, reflects low content of half antibody species in tested samples.

The data in Table 9 demonstrates that the tested kappa-kappa light chain pairing designs were able to promote a substantial increase in bispecific antibody content of designed bispecific chimeric antibodies compared to that of the bispecific chimeric antibody control. This indicates that the stability optimization designs in the Vlambda-Ckappa chimeric light chain are compatible with the kappa-kappa light chain pairing designs tested here.

All references, issued patents, patent applications, and sequence accession numbers (e.g., GenBank accession numbers) cited within the body of the instant specification are hereby incorporated by reference in their entirety, for all purposes.

TABLE 1

Kabat numbering of the light chain variable domain amino acid sequences of H3, EP6b_B01 and CAT-2200 Light chain origin

| KABAT numbering | H3 (SEQ ID No. 3) | EP6b_B01 (SEQ ID No. 6) | CAT-2200 (SEQ ID No. 9) |
|---|---|---|---|
| 1 | Q | Q | N |
| 2 | S | S | F |
| 3 | A | V | M |
| 4 | L | L | L |
| 5 | T | T | T |
| 6 | Q | Q | Q |
| 7 | P | P | P |
| 8 | A | P | H |
| 9 | S | S | S |
| 10 | — | — | — |
| 11 | V | V | V |
| 12 | S | S | S |
| 13 | G | E | E |
| 14 | S | A | S |
| 15 | P | P | P |
| 16 | G | R | G |
| 17 | Q | Q | K |
| 18 | S | T | T |
| 19 | I | V | V |
| 20 | T | T | T |
| 21 | I | I | I |
| 22 | S | S | S |
| 23 | C | C | C |
| 24 | T | S | T |
| 25 | G | G | R |
| 26 | T | N | S |

TABLE 1 -continued

Kabat numbering of the light chain variable domain amino acid sequences of H3, EP6b_B01 and CAT-2200 Light chain origin

| KABAT numbering | H3 (SEQ ID No. 3) | EP6b_B01 (SEQ ID No. 6) | CAT-2200 (SEQ ID No. 9) |
|---|---|---|---|
| 27 | S | S | S |
| 27A | S | S | G |
| 27B | D | N | S |
| 27C | V | — | — |
| 28 | G | I | L |
| 29 | G | G | A |
| 30 | Y | R | N |
| 31 | N | Y | Y |
| 32 | F | P | Y |
| 33 | V | V | V |
| 34 | S | N | Q |
| 35 | W | W | W |
| 36 | Y | Y | Y |
| 37 | Q | Q | Q |
| 38 | Q | Q | Q |
| 39 | H | L | R |
| 40 | P | P | P |
| 41 | G | G | G |
| 42 | K | K | S |
| 43 | A | A | S |
| 44 | P | P | P |
| 45 | K | K | T |
| 46 | L | L | I |
| 47 | M | L | V |
| 48 | I | I | I |
| 49 | Y | Y | F |
| 50 | D | S | A |
| 51 | V | D | N |
| 52 | S | N | N |
| 53 | D | L | Q |
| 54 | R | R | R |
| 55 | P | F | P |
| 56 | S | S | S |
| 57 | G | G | G |
| 58 | V | V | V |
| 59 | S | P | P |
| 60 | D | D | D |
| 61 | R | R | R |
| 62 | F | F | F |
| 63 | S | S | S |
| 64 | G | G | G |
| 65 | S | S | S |
| 66 | K | K | I |
| 66A | — | — | D |
| 66B | — | — | S |
| 67 | S | S | S |
| 68 | G | G | S |
| 69 | N | T | N |
| 70 | T | T | S |
| 71 | A | A | A |
| 72 | S | S | S |
| 73 | L | L | L |
| 74 | I | A | T |
| 75 | I | I | I |
| 76 | S | R | S |
| 77 | G | D | G |
| 78 | L | L | L |
| 79 | Q | L | K |
| 80 | A | S | T |
| 81 | D | E | E |
| 82 | D | D | D |
| 83 | E | E | E |
| 84 | A | A | A |
| 85 | D | D | D |
| 86 | Y | Y | Y |
| 87 | Y | Y | Y |
| 88 | C | C | C |
| 89 | S | S | Q |
| 90 | S | T | T |
| 91 | Y | W | Y |
| 92 | G | D | D |
| 93 | S | D | P |

TABLE 1-continued

Kabat numbering of the light chain variable domain amino acid sequences of H3, EP6b_B01 and CAT-2200 Light chain origin

| KABAT numbering | H3 (SEQ ID No. 3) | EP6b_B01 (SEQ ID No. 6) | CAT-2200 (SEQ ID No. 9) |
|---|---|---|---|
| 94 | S | T | Y |
| 95 | S | L | S |
| 95A | T | E | — |
| 95B | H | G | — |
| 96 | V | W | V |
| 97 | I | V | V |
| 98 | F | F | F |
| 99 | G | G | G |
| 100 | G | G | G |
| 101 | G | G | G |
| 102 | T | T | T |
| 103 | K | K | K |
| 104 | V | V | L |
| 105 | T | T | T |
| 106 | V | V | V |
| 106A | L | L | L |
| 107 | — | — | — |
| 108 | R | R | R |
| 109 | T | T | T |

"—" indicates no corresponding residue

TABLE 2

Amino acid and DNA sequences of wild-type heavy, light and Vλ-Cκ chimeric light chain constructs of H3, EP6b_B01 and CAT-2200

| SEQ ID NO | DESCRIPTION | SEQUENCE |
|---|---|---|
| 1 | H3 heavy chain Fab (Domain boundaries: VH; Q1-S118; CH1; A119-V216, Hinge (partial); E217-T226) | QVQLQESGGGLVKPGGSLRLSCAASGFTFSSYWMSWVRQAPGKGLEWVANINRDGSASYY VDSVKGRFTISRDDAKNSLYLQMNSLRAEDTAVYYCARDRGVGYFDLWGRGTLVTVSSAS TKGPSVFPLAPSSKSTSGGTAALGCLVKDYFPEPVTVSWNSGALTSGVHTFPAVLQSSG LYSLSSWTVPSSSLGTQTYICNVNHKPSNTKVDKKVEPKSCDKTHT |
| 2 | H3 light chain (lambda) (Domain boundaries: VL; Q1-L111, CL; G112-S217) | QSALTQPASVSGSPGQSITISCTGTSSDVGGYNFVSWYQQHPGKAPKLMIYDVSDRPSGVS YDRFSGSKSGNTASLIISGLQADDEADYYCSSGSSSTHVIFGGGTKVTVLGQPKAAPSVTL FPPSSEELQANKATLVCLISDFYPGAVTVAWKADSSPVKAGVETTTPSKQSNNKYAASSYL SLTPEQWKSHRSYSCQVTHEGSTVEKTVAPTECS |
| 3 | H3 Vλ-Cκ chimeric light chain (Domain boundaries: VL; Q1-L111, CL; R112-C218) | QSALTQPASVSGSPGQSITISCTGTSSDVGGYNFVSWYQQHPGKAPKLMIYDVSDRPSGVSD RFSGSKSGNTASLIISGLQADDEADYYCSSYGSSSTHVIFGGGTKVTVLRTVAAPSVFIFPP SDEQLKSGTASWCLLNNFYPREAKVQWKVDNALQSGNSQESVTEQDSKDSTYSLSSTLTLSK ADYEKHKVYACEVTHQGLSSPVTKSFNRGEC |
| 4 | EP6b_B01 heavy chain Fab (Domain boundaries: VH; Q1-S132; | QLQLQESGPGLVKPSETLSLTCTVSGASISANSYYGVWVRQSPGKGLEWVGSIAYRGNSNSG STYYNPSLKSRATVSVDSSKNQVSLRLTSVTAADTALYYCARRQLLDDGTGYQWAAFDVWGQ GTMVTVSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHT |

TABLE 2 -continued

Amino acid and DNA sequences of wild-type heavy, light and Vλ-Cκ chimeric light chain constructs of H3, EP6b_B01 and CAT-2200

| SEQ ID NO | DESCRIPTION | SEQUENCE |
|---|---|---|
| | CH1; A133-V230, Hinge (partial); E231-T240) | |
| 5 | EP6b_B01 light chain (lambda) (Domain boundaries: VL; Q1-L110, CL; G111-S216) | QSVLTQPPSVSEAPRQTVTISCSGNSSNIGRYPVNWYQQLPGKAPKLLIYSDNLRFSGVPDRF SGSKSGTTASLAIRDLLSEDEADYYCSTWDDTLEGWVFGGGTKVTVLGQPKAAPSVTLFPPSS EELQANKATLVCLISDFYPGAVTVAWKADSSPVKAGVETTTPSKQSNNKYAASSYLSLTPEQW KSHRSYSCQVTHEGSTVEKTVAPTECS |
| 6 | EP6b_B01 Vλ-Cκ chimeric light chain (Domain boundaries: VL; Q1-L110, CL; R111-C217) | QSVLTQPPSVSEAPRQTVTISCSGNSSNIGRYPVNWYQQLPGKAPKLLIYSDNLRFSGVPDRF SGSKSGTTASLAIRDLLSEDEADYYCSTWDDTLEGWVFGGGTKVTVLRTVAAPSVFIFPPSDE QLKSGTASVVCLLNNFYPREAKVQWKVDNALQSGNSQESVTEQDSKDSTYSLSSTLTLSKADY EKHKVYACEVTHQGLSSPVTKSFNRGEC |
| 7 | CAT-2200 heavy chain Fab (domain boundaries: VH; E1-S118, CH1; A119-V216, Hinge (partial); E217-T226) | EVQLLESGGGLVQPGGSLRLSCAASGFTFSSYAMSWVRQAPGKGLEWVSAISGSGGSTYYADS VKGRFTISRDNSKNTLYLQMNSLRAEDTAVYYCARDLIHGVTRNWGQGTLVTVSSASTKGPSV FPLAPSSKSTSGGTAALGCLVKDYFPQPVTVSWNSGALTSGVHTFPAVLQSSGLYSLSSWTVP SSSLGTQTYICNVNHKPSNTKVDKKVEPKSCDKTHT |
| 8 | CAT-2200 light chain (lambda) (Domain boundaries: VL; N1-L110, CL; G111-S216) | NFMLTQPHSVSESPGKTVTISCTRSSGSLANYYVQWYQQRPGSSPTIVIFANNQRPSGVPDRFS GSIDSSSNSASLTISGLKTEDEADYYCQTYDPYSWFGGGTKLTVLGQPKAAPSVTLFPPSSEEL QANKATLVCLISDFYPGAVTVAWKADSSPVKAGVETTTPSKQSNNKYAASSYLSLTPEQWKSHR SYSCQVTHEGSTVEKTVAPTECS |
| 9 | CAT-2200 Vλ-Cκ chimeric light chain (domain boundaries: VL; N1-L110, CL; R111-C217) | NFMLTQPHSVSESPGKTVTISCTRSSGSLANYYVQWYQQRPGSSPTIVIFANNQRPSGVPDRFS GSIDSSSNSASLTISGLKTEDEADYYCQTYDPYSWFGGGTKLTVLRTVAAPSVFIFPPSDEQLK SGTASVVCLLNNFYPREAKVQWKVDNALQSGNSQESVTEQDSKDSTYSLSSTLTLSKADYEKHKV YACEVTHQGLSSPVTKSFNRGEC |
| 10 | Pertuzumab heavy chain Fab (Domain boundaries: VH; E1-S119, CH1; A120-V217, Hinge (partial); E218-T227) | EVQLVESGGGLVQPGGSLRLSCAASGFTFTDYTMDWVRQAPGKGLEWVADVNPNSGGSIYNQRF KGRFTLSVDRSKNTLYLQMNSLRAEDTAVYYCARNLGPSFYFDYWGQGTLVTVSSASTKGPSVF PLAPSSKSTSGGTAALGCLVKDYFPEPVTVSWNSGALTSGVHTFPAVLQSSGLYSLSSVVTVPS SSLGTQTYICNVNHKPSNTKVDKKVEPKSCDKTHT |

TABLE 2 -continued

Amino acid and DNA sequences of wild-type heavy, light and Vλ-Cκ chimeric light chain constructs of H3, EP6b_B01 and CAT-2200

| SEQ ID NO | DESCRIPTION | SEQUENCE |
| --- | --- | --- |
| 11 | Pertuzumab light chain (kappa) (Domain boundaries: VL; D1-K107, CL; R108-C214) | DIQMTQSPSSLSASVGDRVTITCKASQDVSIGVAWYQQKPGKAPKLLIYSASYRYTGVPSRFSG SGSGTDFTLTISSLQPEDFATYYCQQYYIYPYTFGQGTKVEIKRTVAAPSVFIFPPSDEQLKSG TASVVCLLNNFYPREAKVQWKVDNALQSGNSQESVTEQDSKDSTYSLSSTLTLSKADYEKHKVYA CEVTHQGLSSPVTKSFNRGEC |
| 12 | D3H44 heavy chain Fab (Domain boundaries: VH; E1-S117, CH1; A118-V215, Hinge (partial); E216-T225) | EVQLVESGGGLVQPGGSLRLSCAASGFNIKEYYMHWVRQAPGKGLEWVGLIDPEQGNTIYDPKF QDRATISADNSKNTAYLQMNSLRAEDTAVYYCARDTAAYFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHT |
| 13 | D3H44 light (chain (kappa) Domain boundaries: VL; D1-K107, C; R108-C214) | DIQMTQSPSSLSASVGDRVTITCRASRDIKSYLNWYQQKPGKAPKVLIYYATSLAEGVPSRFSG SGSGTDYTLTISSLQPEDFATYYCLQHGESPWTFGQGTKVEIKRTVAAPSVFIFPPSDEQLKSG TASVVCLLNNFYPREAKVQWKVDNALQSGNSQESVTEQDSKDSTYSLSSTLTLSKADYEKHKVY ACEVTHQGLSSPVTKSFNRGEC |
| 14 | IgG1 Fc (Domain boundaries: Hinge (partial); D1-P10, CH2; A11-K120, CH3; G121-K227) | DKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGK |
| 15 | IgG1 Fc | GATAAGACCCACACCTGCCCTCCCTGTCCAGCTCCAGAACTGCTGGGAGGACCTAGCGTGTTCC TGTTTCCCCCTAAGCCAAAAGACACTCTGATGATTTCCAGGACTCCCGAGGTGACCTGCGTGGT GGTGGACGTGTCTCACGAGGACCCCGAAGTGAAGTTCAACTGGTACGTGGATGGCGTGGAAGTG CATAATGCTAAGACAAAACCAAGAGAGGAACAGTACAACTCCACTTATCGCGTCGTGAGCGTG TGACCGTGCTGCACCAGGACTGGCTGAACGGGAAGGAGTATAAGTGCAAAGTCAGTAATAAGGC CCTGCCTGCTCCAATCGAAAAAACCATCTCTAAGGCCAAAGGCCAGCCAAGGGAGCCCCAGGTG TACACACTGCCACCCAGCAGAGACGAACTGACCAAGAACCAGGTGTCCCTGACATGTCTGGTGA AAGGCTTCTATCCTAGTGATATTGCTGTGGAGTGGGAATCAAATGGACAGCCAGAGAACAATTA CAAGACCACACCTCCAGTGCTGGACAGCGATGGCAGCTTCTTCCTGTATTCCAAGCTGACAGTG GATAAATCTCGATGGCAGCAGGGGAACGTGTTTAGTTGTTCAGTGATGCATGAAGCCCTGCACA ATCATTACACTCAGAAGAGCCTGTCCCTGTCTCCCGGCAAA |
| 16 | H3 heavy chain Fab | CAGGTCCAGCTGCAGGAATCTGGCGGAGGACTGGTCAAACCTGGAGGCTCTCTGAGACTGTCAT GTGCTGCTAGTGGCTTTACTTTCAGCTCCTACTGGATGTCTTGGGTGCGACAGGCCCCCGGCAA GGGACTGGAGTGGGTCGCAAACATCAATAGAGACGGATCTGCCAGTTACTATGTGGATAGCGTC AAGGGCCGGTTCACCATTTCAAGAGACGATGCTAAAAACAGCCTGTATCTGCAGATGAACAGCCT GAGGGCCGAAGACACAGCTGTGTACTATTGCGCACGCGATCGCGGCGTGGGATATTTCGATCTGT GGGGCCGCGGAACCCTGGTGACCGTCTCATCTGCTAGCACTAAGGGGCCTTCCGTGTTTCCACTG GCTCCCTCTAGTAAATCCACCTCTGGAGGCACAGCTGCACTGGGATGTCTGGTGAAGGATTACTT CCCTGAACCAGTCACAGTGAGTTGGAACTCAGGGGCTCTGACAAGTGGAGTCCATACTTTTCCG CAGTGCTGCAGTCAAGCGGACTGTACTCCCTGTCCTCTGTGGTCACCGTGCCTAGTTCAAGCCTG GGCACCCAGACATATATCTGCAACGTGAATCACAAGCCATCAAATACAAAAGTCGACAAGAAGGT GGAACCAAAAAGCTGCGATAAAACCCATACA |
| 17 | H3 light chain (lambda) | CAGAGCGCACTGACTCAGCCTGCTTCCGTGTCCGGCTCCCCTGGGCAGAGTATTACAATCTCATG CACTGGCACCTCATCCGACGTGGGCGGGTACAACTTTGTCAGCTGGTATCAGCAGCACCCAGGCA AGGCCCCCAAACTGATGATCTACGACGTGTCCGATCGGCCTTCCGGGGTCTCTGACAGATTCTCC GGATCTAAGAGTGGCAATACCGCCAGCCTGATCATTTCCGGGCTGCAGGCAGACGATGAGGCCGA TTACTATTGCAGCTCCTATGGGATCTAGTTCAACACATGTGATCTTCGGAGGCGGGACCAAGGTGA CAGTCCTGGGGCAGCCTAAAGCGGCGCCCTCTGTGACTCTGTTTCCCCCTAGCTCCGAGGAACTG |

TABLE 2 -continued

Amino acid and DNA sequences of wild-type heavy, light and Vλ-Cκ chimeric light chain constructs of H3, EP6b_B01 and CAT-2200

| SEQ ID NO | DESCRIPTION | SEQUENCE |
|---|---|---|
| | | CAGGCTAACAAGGCAACTCTGGTGTGTCTGATTAGCGACTTCTACCCAGGAGCTGTGACCGTCGC<br>CTGGAAGGCTGATTCTAGTCCCGTGAAAGCAGGCGTCGAGACCACAACTCCTAGTAAGCAGTCAA<br>CAACAAGTACGCAGCCTCAAGCTATCTGTCTCTGACACCCGAACAGTGGAAAAGTCACAGGTCA<br>TATAGCTGCCAGGTGACTCACGAGGGCTCAACTGTGGAGAAAACCGTCGCACCAACCGAATGTTCC |
| 18 | H3 Vλ-Cκ chimeric light chain | CAGAGCGCACTGACTCAGCCTGCATCCGTGTCCGGGTCCCCTGGGCAGAGCATTACTATTTCATGT<br>ACTGGAACTTCTTCAGACGTGGGCGGGTACAACTTCGTGTCCTGGTATCAGCAGCACCCCGGCAA<br>GGCACCTAAACTGATGATCTACGACGTGAGCGATCGACCAAGCGGGGTCTCCGACAGATTTTCTG<br>GAAGTAAATCAGGCAATACCGCCTCTCTGATCATTAGTGGGCTGCAGGCCGACGATGAGGCTGAT<br>TACTATTGCAGCTCCTATGGATCTAGTAGCACCCATGTCATTTTCGGAGGCGGAACAAAGGTCAC<br>CGTCCTGAGAACCGTGGCGGCGCCCAGTGTCTTCATTTTTCCCCCTAGCGACGAACAGCTGAAGT<br>CTGGGACAGCCAGTGTGGTCTGTCTGCTGAACAACTTCTACCCTCGCGAGGCTAAAGTGCAGTGG<br>AAGGTCGATAACGCACTGCAGTCCGGAAATTCTCAGGAGAGTGTGACTGAACAGGACTCAAAAGA<br>TAGCACCTATTCCCTGTCAAGCACACTGACTCTGAGCAAGGCCGACTACGAGAAGCATAAAGTGT<br>ATGCTTGTGAAGTCACCCACCAGGGGCTGAGTTCACCAGTCACAAAATCATTCAACAGAGGGGAGT<br>GC |
| 19 | EP6b_B01 heavy chain Fab | CAGCTGCAGCTGCAGGAAAGCGGGCCTGGGCTGGTGAAACCTTCCGAAACACTGTCCCTGACTTGT<br>ACTGTGAGCGGGGCATCAATTAGTGCCAACTCATACTATGGCGTGTGGGTCCGACAGAGTCCAGGA<br>AAGGGACTGGAGTGGGTGGGGTCCATCGCCTACAGAGGAAACAGTAATTCAGGCAGCACATACTAT<br>AACCCCTAGCCTGAAGTCCAGGGCTACTGTGAGCGTGGACAGCTCCAAAAATCAGGTGTCACTGCGC<br>CTGACTAGCGTCACCGCCGCTGATACCGCCCTGTCTATTGCGCTGGAGACAGCTGCTGGACGAT<br>GGGACAGGATACCAGTGGGCAGCCTTCGACGTGTGGGACAGGGGACAATGGTGACTGTCTCTAGT<br>GCTAGCACCAAGGGGCCAAGCGTGTTCCCACTGGCACCCTCAAGCAAATCCACCTCTGGAGGAACA<br>GCTGCACTGGGATGCCTGGTGAAGGATTATTTCCCCGAACCTGTGACTGTCTCTTGGAATAGTGGG<br>GCACTGACTTCTGGAGTGCACACCTTTCCCGCCGTCCTGCAGTCCTCTGGACTGTACTCCTGAGT<br>TCAGTGGTCACAGTGCCTAGCTCCTCTCTGGGCACCCAGACATACATCTGTAACGTGAACCATAAG<br>CCATCAAACACTAAAGTCGACAAGAAGGTGGAGCCAAAGTCCTGTGACAAGACCCATACA |
| 20 | EP6b_B01 light chain (lambda) | CAGAGCGTCCTGACTCAGCCTCCCTCCGTGTCCGAAGCACCTCGGCAGACTGTGACTATCTCATGT<br>TCTGGCAACTCATCAAATATCGGAAGGTACCCAGTGAACTGGTATCAGCAGCTGCCCGGCAAGGCA<br>CCTAAACTGCTGATCTACAGTGACAATCTGCGGTTCTCAGGGGTCCCCGATCGGTTCAGCGGCTCC<br>AAGTCTGGGACCACAGCCAGCCTGGCTATTGGGACCTGCTGTCCGAGGACGAAGCCGATTACTAT<br>TGCAGTACCTGGGACGATACCCTGGAAGGATGGGTCTTCGGCGGCGGCACAAAAGTCACCGTCCTG<br>GGGCAGCCAAAGGCGGCGCCCAGTGTCACACTGTTTCCCCCTAGCTCCGAGGAACTGCAGGCTAAC<br>AAAGCAACACTGGTGTGTCTGATCAGCGACTTCTACCCTGGAGCTGTGACTGTCGCCTGGAAGGCT<br>GATTCTAGTCCAGTGAAAGCAGGCGTCGAGACCACAACTCCCTCTAAGCAGAGTAACAACAAGTAC<br>GCAGCCTCAAGCTATCTGTCACTGACCCCAGAACAGTGGAAGAGCCACCGGAGCTATTCCTGCCAG<br>GTCACTCACGAAGGCTCCACTGTCGAGAAAACCGTCGCTCCCACCGAATGTTCA |
| 21 | EP6b_B01 Vλ-Cκ chimeric light chain | CAGAGCGTCCTGACTCAGCCTCCTTCCGTGTCCGAGGCACCCCGCCAGACCGTGACTATCTCATGT<br>TCCGGCAACTCCTCAAATATCGGAAGGTACCCAGTGAACTGGTATCAGCAGCTGCCCGGCAAGGCA<br>CCTAAACTGCTGATCTACAGTGACAATCTGCGGTTCTCAGGGGTCCCCGATCGGTTCAGCGGCTCC<br>AAGTCTGGGACCACAGCCAGCCTGGCTATTGGGACCTGCTGTCCGAGGACGAAGCCGATTACTAT<br>TGCAGTACCTGGGATGATACCCTGGAAGGATGGGTCTTTGGAGGAGGAACTAAAGTCACCGTGCTG<br>AGAACCGTGGCGGCGCCCAGTGTCTTCATTTTTCCCCCTAGCGACGAACAGCTGAAGTCTGGGACA<br>GCCAGTGTGGTCTGTCTGCTGAACAACTTCTACCCTAGAGAGGCTAAAGTGCAGTGGAAGGTCGAT<br>AACGCACTGCAGTCCGGAAATTCTCAGGAGAGTGTGACTGAACAGGACTCAAAAGATAGCACCTAT<br>TCCCTGTCAAGCACACTGACTCTGAGCAAGGCCGACTACGAGAAGCATAAAGTGTATGCTTGTGAA<br>GTCACCCACCAGGGGCTGAGTTCACCAGTCACAAAATCATTCAACAGAGGGGAGTGC |
| 22 | CAT-2200 heavy chain Fab | GAGGTGCAGCTGCTGGAATCTGGGGGGGGCCTGGTGCAGCCTGGGGGGTCCCTGAGACTGTCATGT<br>GCTGCCAGCGGGTTTACTTTCAGCTCCTACGCTATGTCCTGGGTGCGACAGGCACCCGGGAAGGGA<br>CTGGAGTGGGTCTCTGCAATCAGTGGGTCAGGCGGGAGTACTTACTATGCCGACAGCGTGAAGGGA<br>CGGTTCACTATCTCAAGAGATAACAGCAAGAACACCCTGTATCTGCAGATGAACAGCCTGAGAGCA<br>GAAGACACAGCCGTGTACTATTGCGCCAGGGATCTGATCCACGGAGTCACTCACAGCCAATTGGGGCCAG<br>GGGACTCTGGTGACCGTCTCTAGTGCTAGCACAAAGGGGCCCTCTGTGTTTCCACTGGCCCCCTCA<br>AGCAAAAGCACATCCGGAGGAACTGCAGCTCTGGGATGTCTGGTGAAGGACTACTTCCCCCAGCCT<br>GTGACCGTCTCTTGGAACAGTGGAGCCCTGACCAGCGGCGTGCACACATTTCCTGCTGTCCTGCAGT<br>CCTCTGGCCTGTACTCCCTGAGTTCAGTGGTCACAGTGCCTAGCTCCTCTCTGGGGACCCAGACATA<br>TATTTGCAACGTGAATCATAAACCAAGCAACACTAAGGTCGACAAGAAAGTGGAGCCCAAGAGCTGT<br>GATAAAACTCATACC |
| 23 | CAT-2200 light chain (lambda) | AACTTTATGCTGACTCAGCCCCACTCCGTGTCCGAGAGCCCTGGCAAAACTGTGACTATTTCATGTA<br>CCCGATCATCTGGAAGCCTGGCCAACTACTATGTGCAGTGGTACCAGCAGAGGCCAGGCAGCTCCCC<br>CACTATCGTGATTTTCGCTAACAATCAGCGGCCTTCCGGCGTCCCAGACAGATTTTCCGGGTCTATC<br>GATTCTAGTTCAAATAGTGCATCACTGACTATTTCCGGGCTGAAGACCGAGGACGAAGCCGATTACT<br>ATTGCAGCACCTACGACCCCTATTCTGTGGTCTTCGGCGGGGGAACCAAGCTGACAGTGCTGGGAA<br>GCCAAAAGCGGCGCCCAGTGTCACACTGTTTCCCCCTAGCTCCGAGGAACTGCAGGCTAACAAAGCA<br>ACACTGGTGTGTCTGATCAGCGACTTCTACCCCTGGAGCTGTGACTGTCGCCTGGAAGGCTGATTCTA<br>GTCCAGTGAAAGCAGGCGTCGAGACCACAACTCCCTCTAAGCAGAGTAACAACAAGTACGCAGCCTC<br>AAGCTATCTGTCACTGACCCCAGAACAGTGGAAGAGCCACCGGAGCTATTCCTGCCAGGTCACTCAC<br>GAAGGCTCCACTGTCGAGAAAACCGTCGCTCCCACCGAATGTTCA |

TABLE 2 -continued

Amino acid and DNA sequences of wild-type heavy, light and Vλ-Cκ chimeric light chain constructs of H3, EP6b_B01 and CAT-2200

| SEQ ID NO | DESCRIPTION | SEQUENCE |
|---|---|---|
| 24 | CAT-2200 Vλ-Cκ chimeric light chain | AACTTTATGCTGACACAGCCTCACTCTGTGAGTGAGTCACCCGGAAAGACCGTCACAATCTCTTGCA CTAGGAGCTCCGGCAGCCTGGCAAACTACTATGTGCAGTGGTACCAGCAGCGGCCCGGGTCTAGTCC TACCATCGTGATTTTCGCCAACAATCAGCGACCATCCGGAGTCCCAGACCGGTTCAGCGGGTCCATC GATTCAAGCTCCAATTCTGCCAGTCTGACTATTAGCGGCCTGAAAACCGAGGACGAAGCTGATTACT ATTGTCAGACATACGATCATATATTGGTCTTTGGCGGAGGAACTAAGCTGACCGTGCTGACAA CGTGGCGGCGCCCAGTGTCTTCATTTTTCCCCCTAGCGACGAACAGCTGAAGTCTGGGACAGCCAGT GTGGTCTGTCTGCTGAACAACTTCTACCCTAGAGAGGCTAAAGTGCAGTGGAAGGTCGATAACGCAC TGCAGTCCGGAAATTCTCAGGAGAGTGTGACTGAACAGGACTCAAAAGATAGCACCTATTCCCTGTC AAGCACACTGACTCTGAGCAAGGCCGACTACGAGAAGCATAAAGTGTATGCTTGTGAAGTCACCCAC CAGGGGCTGAGTTCACCAGTCACAAAATCATTCAACAGAGGGGAGTGC |
| 25 | Pertuzumab heavy chain Fab | GAAGTGCAGCTGGTCGAATCTGGAGGAGGACTGGTGCAGCCAGGAGGGTCCCTGCGCCTGTCTTGCGC CGCTAGTGGCTTCACTTTTACCGACTACACCATGGATTGGGTGCGACAGGCACCTGGAAAGGGCCTGG AGTGGGTCGCCGATGTGAACCCAAATAGCGGAGGCTCCATCTACAACCAGCGGTTCAAGGGCCGGTTC ACCCTGTCAGTGGACCGGAGCAAAAACACCCTGTATCTGCAGATGAATAGCCTGCGAGCCGAAGATAC TGCTGTGTACTATTGCGCCCGGAATCTGGGGCCCTCCTTCTACTTTGACTATGGGGGCAGGGAACTC TGGTCACCGTGAGCTCCGCCTCCACCAAGGGACCTTCTGTGTTCCCACTGGCTCCCTCTAGTAAATCC ACATCTGGGGGAACTGCAGCCCTGGGCTGTCTGGTGAAGGACTACTTCCCAGAGCCCGTCACAGTGTC TTGGAACAGTGGCGCTCTGACTTCTGGGGTCCACACCTTTCCTGCAGTGCTGCAGTCAAGCGGGCTGT ACAGCCTGTCCTCTGTGGTCACCGTGCCAAGTTCAAGCCTGGGAACACAGACTTATATCTGCAACGTG AATCACAAGCCATCCAATACAAAAGTCGACAAGAAAGTGGAACCCAAGTCTTGTGATAAAACCCATACA |
| 26 | Pertuzumab light chain (kappa) | GATATTCAGATGACCCAGTCCCCAAGCTCCCTGAGTGCCTCAGTGGGCGACCGAGTCACCATCACATGC AAGGCTTCCCAGGATGTGTCTATTGGAGTCGCATGGTACCAGCAGAAGCCAGGCAAAGCACCCAAGCTG CTGATCTATAGCGCCTCCTACCGGTATACCGGCGTGCCCTCTAGATTCTCTGGCAGTGGTCAGGAACA GACTTTACTCTGACCATCTCTAGTCTGCAGCCTGAGGATTTCGCTACCTACTATTGCCAGCAGTACTAT ATCTACCCATATACCTTTGGCCAGGGACAAAAGTGGAGATCAAGAGGACTGTGGCCGCTCCTCCGTC TTCATTTTTCCCCCTTCTGACGAACAGCTGAAAAGTGGCACAGCCAGCGTGGTCTGTCTGCTGAACAAT TTCTACCCTCGCGAAGCCAAAGTGCAGTGGAAGGTCGATAACGCTCTGCAGAGCGGCAACAGCCAGGA GTCTGTGACTGAACAGGACAGTAAAGATTCAACCTATAGCCTGTCAAGCACACTGACTCTGAGCAAGGCA GACTACGAGAAGCACAAAGTGTATGCCTGCGAAGTCACACATCAGGGGCGTGTCCTCTCCTGTGACTAAG AGCTTTAACAGAGGAGAGTGT |
| 27 | D3H44 heavy chain Fab | GAGGTCCAGCTGGTCGAGTCTGGAGGAGGACTGGTGCAGCCAGGAGGGAGCCTGCGACTGTCCTGCGCC GCTTCTGGCTTCAACATCAAGGAATACTATATGCACTGGGTGAGACAGGCACCAGGCAAAGGACTGGAG TGGGTCGGGCCTGATCGACCCTGAACAGGGGAACACCATCTACGACCCAAAGTTTCAGGATCGGGCCACT ATTAGTGCTGACAACTCAAAAAATACCGCATATCTGCAGATGAACAGCCTGAGGGCAGAGGATACAGCC GTGTACTATTGCGCCCGGGACACTGCAGCCTACTTCGATTATTGGGGACAGGGCACACTGGTCACTGTG AGCTCCGCTAGCACTAAGGGGCCTTCCGTGTTTCCACTGGCTCCCTCTAGTAAATCCACCTCTGGAGGC ACAGCTGCACTGGGATGTCTGGTGAAGGATTACTTCCCTGAACCAGTCACAGTGAGTTGGAACTCAGGG GCTCTGACAAGTGGAGTCCATACTTTTCCCGCAGTGCTGCAGTCAAGCGGACTGTACTCCCTGTCCTCT GTGGTCACCGTGCCTAGTTCAAGCCTGGGCACCCAGACATATATCTGCAACGTGAATCACAAGCCATCA AATACAAAAGTCGACAAGAAAGTGGACCCAAGAGCTGTGATAAAACTCATACCTGCCCACCTTGTCCG GCGCCAGAAC |
| 28 | D3H44 light chain (kappa) | GACATCCAGATGACCCAGTCCCCTAGCTCCCTGTCCGCCTCTGTGGGCGACAGGGTGACCATCACATGC CGGGCCAGCAGAGATATCAAGTCCTACCTGAACTGGTATCAGCAGAAGCCCGGCAAGGCCCCTAAGGTG CTGATCTACTATGCCACATCTCTGGCCGAGGGAGTGCCAAGCCGCTTCAGCGGCTCCGGCTCTGGAACC GACTACACCCTGACAATCTCTAGCCTGCAGCCAGAGGATTTCGCCACATACTATTGTCTGCAGCACGGC GAGTCTCCCTGGACCTTTGGCCAGGGACAAAAGGTGGAGATCAAGCGGACCGTGGCGGCCGCCAGTGTC TTCATTTTTCCCCCTAGCGACGAACAGCTGAAGTCTGGGACAGCCAGTGTGGTCTGTCTGCTGAACAAC TTCTACCCTAGAGAGGCTAAAGTGCAGTGGAAGGTCGATAACGCACTGCAGTCCGGAAATTCTCAGGAG CAGTGTGACTGAACAGGACTCAAAAGATAGCACCTATTCCCTGTCAAGCACACTGACTCTGAGCAAGGCC GACTACGAGAAGCATAAAGTGTATGCTTGTGAAGTCACCCACCAGGGGCTGAGTTCACCAGTCACAAAA TCATTCAACAGAGGGGAGTGC |
| 29 | IgG1 Fc sequence 231-447 (EU-numbering), without hinge | APELLGGPSVFLFPPKPKDTLMISRTPEVTCVWDVSHEDPEVKFNWYVDGVEVHNAKTKPREEQYNSTY RVVSVITVLHQDWLNGKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNVFSCSVMHEALHNHYTQ KSLSLSPGK |
| 30 | Upper IgG1 hinge | EPKSCDKTHT |
| 31 | Ckappa (CH1) domain of IGKC*01 | RTVAAPSVFIFPPSDEQLKSGTASVVCLLNNFYPREAKVQWKVDNALQSGNSQESVTEQDSKDSTYSLSS TLTLSKADYEKHKVYACEVTHQGLSSPVTKSFNRGEC |

TABLE 2 -continued

Amino acid and DNA sequences of wild-type heavy, light and Vλ-Cκ chimeric light chain constructs of H3, EP6b_B01 and CAT-2200

| SEQ ID NO | DESCRIPTION | SEQUENCE |
|---|---|---|
| 32 | Lower IgG1 hinge | CPPCP |

TABLE 3

Stability optimization design library

| Design identifier | Vλ-Cκ chimeric light chain mutation (Kabat) |
|---|---|
| 1 | T105E_L106AK |
| 2 | E83F_T105E_L106AK |
| 3 | E83F_T105E_V106I_L106AK |
| 4 | T80A_E83F_T105E_L106AK |
| 5 | T80A_E83F_T105E_V106I_L106AK |
| 6 | T80A_E83F_D85T_T105E_L106AK |
| 7 | T80A_E83F_D85T_T105E_V106I_L106AK |
| 8 | T80P_E83F_D85T_T105E_V106I_L106AK |
| 9 | D85T |
| 10 | D85V |
| 11 | T105E |
| 12 | L106AK |
| 13 | V106I |
| 14 | E83F |
| 15 | E83F_T105E |
| 16 | E83F_V106I |
| 17 | E83F_D85T |
| 18 | E83F_D85T_T105E |
| 19 | E83F_D85V_T105E |
| 20 | E83F_D85T_T105E_V106I |
| 21 | E83F_D85V_T105E_V106I |
| 22 | E83F_D85T_T105E_V106I_L106AK |
| 23 | E83V |
| 24 | E83V_T105E |
| 25 | E83V_V106I |
| 26 | E83V_D85T |
| 27 | E83V_D85T_T105E |
| 28 | E83V_D85V_T105E |
| 29 | E83V_D85T_T105E_V106I |
| 30 | E83I |
| 31 | E83I_T105E |
| 32 | E83I_D85T |
| 33 | E83I_D85T_T105E |
| 34 | E83I_D85T_T105E_V106I |
| 35 | E83A |
| 36 | E83A_T105E |
| 37 | E83A_D85T |
| 38 | E83A_D85T_T105E |
| 39 | E83A_D85T_T105E_V106I |

TABLE 4

Thermal stability assessment of the designed Vλ-Cκ chimeric Fabs

| Column 1 Design identifier | Column 2 Tm (° C.) of designed CAT-2200, by DSF | Column 3 Change in Tm (DSF) of designed CAT-2200 vs chimera | Column 5 Tm (° C.) of designed H3, by DSF | Column 6 Change in Tm (DSF) of designed H3 vs chimera | Column 7 Tm (° C.) of designed EP6b_B01, by DSF | Column 8 Change in Tm (DSF) of designed EP6b_B01 vs chimera | Column 9 Tm (° C.) of designed CAT-2200, by DSC | Column 10 Change in Tm (DSC) of designed CAT-2200 vs chimera | Column 11 Tm (° C.) of designed H3, by DSC | Column 12 Change in Tm (DSC) of designed H3 vs chimera | Column 13 Tm (° C.) of designed EP6b_B01, by DSC | Column 14 Change in Tm (DSC) of designed EP6b_B01 vs chimera |
|---|---|---|---|---|---|---|---|---|---|---|---|---|
| WT | *78.8 | 5.7 | *80.9 | 4.9 | *85.4 | 4.9 | 72.6 | 4.6 | 75.3 | 3.7 | 81.1 | 4.4 |
| chimera | 73.1 | N/A | 76.0 | N/A | 80.5 | N/A | 68.0 | N/A | 71.6 | N/A | 76.7 | N/A |
| 1 | / | / | / | / | / | / | *68.2 | 0.2 | / | / | / | / |
| 2 | / | / | / | / | / | / | *73.0 | 5.0 | / | / | / | / |
| 3 | / | / | / | / | / | / | *73.3 | 5.3 | / | / | / | / |
| 4 | / | / | / | / | / | / | *73.1 | 5.1 | / | / | / | / |
| 5 | / | / | / | / | / | / | *73.1 | 5.1 | / | / | / | / |
| 6 | / | / | / | / | / | / | *75.8 | 7.8 | / | / | / | / |
| 7 | / | / | / | / | / | / | *76.0 | 8.0 | / | / | / | / |
| 8 | / | / | / | / | / | / | *76.3 | 8.3 | / | / | / | / |
| 9 | 74.8 | 1.7 | 77.7 | 1.7 | / | / | / | / | / | / | / | / |
| 10 | 74.5 | 1.4 | 77.5 | 1.5 | / | / | / | / | / | / | / | / |
| 11 | 73.3 | 0.2 | 76.0 | 0 | / | / | / | / | / | / | / | / |
| 12 | 73.0 | 0 | 76.0 | 0 | / | / | / | / | / | / | / | / |
| 13 | 73.2 | 0.1 | 76.2 | 0.2 | / | / | / | / | / | / | / | / |
| 14 | 76.25 | 3.2 | 77.8 | 1.8 | / | / | / | / | / | / | / | / |
| 15 | 77.0 | 3.9 | 78.7 | 2.7 | / | / | / | / | / | / | / | / |
| 16 | 76.2 | 3.1 | 77.5 | 1.5 | / | / | / | / | / | / | / | / |
| 17 | 78.9 | 5.8 | 80.5 | 4.5 | / | / | / | / | / | / | / | / |
| 18 | 79.2 | 6.1 | 82.3 | 6.3 | *88.7 | 8.2 | 75.4 | 7.4 | 78.3 | 6.7 | 84.6 | 7.9 |
| 19 | 79.3 | 6.2 | 82.2 | 6.2 | / | / | / | / | / | / | / | / |
| 20 | 79.2 | 6.1 | 82.0 | 6.0 | / | / | / | / | / | / | / | / |
| 21 | 79.5 | 6.4 | 81.5 | 5.5 | / | / | / | / | / | / | / | / |
| 22 | / | / | 81.5 | 5.5 | / | / | / | / | / | / | / | / |

TABLE 4-continued

Thermal stability assessment of the designed Vλ-Cκ chimeric Fabs

| Column 1 Design identifier | Column 2 Tm (° C.) of designed CAT-2200, by DSF | Column 3 Change in Tm (DSF) of designed CAT-2200 vs chimera | Column 5 Tm (° C.) of designed H3, by DSF | Column 6 Change in Tm (DSF) of designed H3 vs chimera | Column 7 Tm (° C.) of designed EP6b_B01, by DSF | Column 8 Change in Tm (DSF) of designed EP6b_B01 vs chimera | Column 9 Tm (° C.) of designed CAT-2200, by DSC | Column 10 Change in Tm (DSC) of designed CAT-2200 vs chimera | Column 11 Tm (° C.) of designed H3, by DSC | Column 12 Change in Tm (DSC) of designed H3 vs chimera | Column 13 Tm (° C.) of designed EP6b_B01, by DSC | Column 14 Change in Tm (DSC) of designed EP6b_B01 vs chimera |
|---|---|---|---|---|---|---|---|---|---|---|---|---|
| 23 | 80.0 | 6.9 | 81.2 | 5.2 | / | / | / | / | / | / | / | / |
| 24 | 79.8 | 6.7 | 81.5 | 5.5 | / | / | / | / | / | / | / | / |
| 25 | 80.3 | 7.2 | 82.8 | 6.8 | / | / | / | / | / | / | / | / |
| 26 | 81.0 | 7.9 | 84.2 | 8.2 | #90.8 | 10.3 | 77.6 | 9.6 | 80.5 | 8.9 | 88.2 | 11.4 |
| 27 | 81.0 | 7.9 | 85.0 | 9.0 | / | / | / | / | / | / | / | / |
| 28 | 81.3 | 8.2 | 85.0 | 9.0 | / | / | / | / | / | / | / | / |
| 29 | 81.0 | 7.9 | 87.0 | 11.0 | #90.3 | 9.8 | 77.6 | 9.6 | 83.4 | 11.8 | 87.7 | 11 |
| 30 | 79.5 | 6.4 | 81.0 | 5.0 | / | / | / | / | / | / | / | / |
| 31 | 79.7 | 6.6 | 81.0 | 5.0 | / | / | / | / | / | / | / | / |
| 32 | 80.5 | 7.4 | 84.0 | 8.0 | #91.9 | 11.4 | 77.6 | 9.6 | 80.2 | 8.6 | 88.9 | 12.2 |
| 33 | 81.0 | 7.9 | 85.0 | 9.0 | / | / | / | / | / | / | / | / |
| 34 | 81.0 | 7.9 | 86.5 | 10.5 | #91.1 | 10.6 | 77.7 | 9.7 | 82.8 | 11.2 | 88.5 | 11.8 |
| 35 | 80.5 | 7.4 | 84.0 | 8.0 | / | / | / | / | / | / | / | / |
| 36 | 80.7 | 7.6 | 84.2 | 8.2 | / | / | / | / | / | / | / | / |
| 37 | 81.2 | 8.1 | 86.5 | 10.5 | #90.6 | 10.1 | 77.5 | 9.5 | 82.6 | 11.0 | 87.9 | 11.2 |
| 38 | 81.2 | 8.1 | 87.3 | 11.3 | / | / | / | / | / | / | / | / |
| 39 | 81.5 | 8.4 | 88.5 | 12.5 | 92.0 | 11.5 | 78.0 | 10.0 | 85.0 | 13.4 | / | / |

*Average of 2 measurements;
Average of 4 measurements;
/-not determined;

TABLE 5

Thermal stability assessment of the selected designed Vλ-Cκ chimeric Mabs

| Column 1 Design identifier | Column 2 Tm (° C.) of designed CAT-2200, by DSC* | Column 3 Change in Tm (DSC) of designed CAT-2200 vs chimera | Column 4 Tm (° C.) of designed H3, by DSC* | Column 5 Change in Tm (DSC) of designed H3 vs chimera |
|---|---|---|---|---|
| WT | 71.2 | 4.1 | 73.8 | 3.4 |
| chimera | 67.1 | N/A | 70.4 | N/A |
| 18 | 74.8 | 7.7 | 78.1 | 7.7 |
| 26 | 77.2 | 10.1 | 80.4 | 10.0 |
| 29 | 77.3 | 10.2 | 83.3 | 12.9 |
| 32 | 77.2 | 10.1 | 80.2 | 9.8 |
| 34 | 77.4 | 10.3 | 82.7 | 12.3 |
| 37 | 77.2 | 10.1 | 82.5 | 12.1 |
| 39 | 77.7 | 10.6 | 84.2 | 13.8 |

*Measurements are average of n = 3

TABLE 6

Antigen binding assessment of the selected designed Vλ-Cκ chimera Fabs

| Column 1 Design identifier | Column 2 KD (nM) of designed CAT-2200 | Column 3 KD (nM) of designed H3 | Column 4 KD (pM) of designed EP6b_B01 |
|---|---|---|---|
| WT | #0.3 | #92.4 | 54.6 |
| chimera | #0.2 | #92.7 | 51.2 |
| 14 | 0.3 | 92.6 | */ |
| 15 | 0.3 | 90.8 | */ |
| 16 | 0.3 | 88.5 | */ |
| 17 | 0.3 | 83.1 | */ |
| 18 | 0.3 | 90.5 | 44.9 |
| 19 | 0.3 | 83.0 | */ |
| 20 | 0.3 | 85.8 | */ |
| 21 | 0.3 | 82.6 | */ |
| 22 | */ | 80.5 | */ |
| 23 | 0.2 | 95.7 | */ |
| 24 | 0.3 | 102.0 | */ |
| 25 | 0.4 | 80.6 | */ |
| 26 | 0.3 | 82.1 | 48.6 |
| 27 | 0.2 | 84.1 | */ |
| 28 | 0.2 | 89.2 | */ |
| 29 | 0.3 | 77.0 | 47.9 |
| 30 | 0.3 | 95.1 | */ |
| 31 | 0.3 | 82.7 | */ |
| 32 | 0.3 | 83.8 | 47.1 |
| 33 | 0.3 | 89.0 | */ |
| 34 | 0.2 | 75.4 | 48.4 |
| 35 | 0.2 | 59.1 | */ |
| 36 | 0.3 | 66.4 | */ |
| 37 | 0.2 | 83.5 | 49.2 |
| 38 | 0.2 | 72.2 | */ |
| 39 | 0.2 | 89.6 | */ |

*/Not determined;
Measurements are average of n = 3;

TABLE 7

Antigen binding assessment of the selected designed Vλ-Cκ chimera Mabs

| Column 1 Design identifier | Column 2 KD (pM) of designed CAT-2200 | Column 3 KD (nM) of designed H3 |
|---|---|---|
| WT | 27.0 | 85.0 |
| chimera | 42.0 | 63.0 |

TABLE 7-continued

Antigen binding assessment of the selected designed Vλ-Cκ chimera Mabs

| Column 1 Design identifier | Column 2 KD (pM) of designed CAT-2200 | Column 3 KD (nM) of designed H3 |
|---|---|---|
| 18 | 48.0 | 66.0 |
| 26 | 48.0 | 56.0 |
| 29 | 49.0 | 64.0 |
| 32 | 50.0 | 67.0 |
| 34 | 53.0 | 60.0 |
| 37 | 48.0 | 67.0 |
| 39 | 44.0 | 61.0 |

TABLE 8

FcγR and FcRn affinity assessment of the selected designed Vλ-Cκ chimera Mabs

| Column 1 Design identifier | Column 2 KD (μM) of designed Mab:CD16aV[#] | Column 3 KD (μM) of designed Mab:CD32bF[#] | Column 4 KD (μM) of designed Mab:CD32aR | Column 5 KD (μM) of designed Mab:CD32aH | Column 6 KD (nM) of designed Mab:FcRn | Column 7 Mab |
|---|---|---|---|---|---|---|
| WT | 1.2 | 2.9 | 2.4 | 0.7 | 14.2 | CAT-2200 |
| chimera | */ | */ | 2.5 | 0.6 | 14.3 | CAT-2200 |
| 29 | 1.3 | 2.9 | 2.3 | 0.6 | 27.9 | CAT-2200 |
| 37 | 1.4 | 3.1 | 2.4 | 0.6 | 23.4 | CAT-2200 |
| 39 | 1.3 | 3.0 | 2.4 | 0.7 | 24.7 | CAT-2200 |
| WT | 1.1 | 3.3 | 3.4 | 0.6 | 48.6 | H3 |
| chimera | 1.2 | 3.4 | 4.1 | 0.6 | 74.6 | H3 |
| 29 | 1.1 | 3.2 | 4.9 | 0.6 | 86.1 | H3 |
| 37 | 1.3 | 3.3 | 3.4 | 0.6 | 80.2 | H3 |
| 39 | 1.4 | 3.4 | 3.1 | 0.7 | 96.7 | H3 |

*Not determined;
[#]Measurements are average of n = 2;

TABLE 9

LC-MS pairing data for designed bispecific chimeric Abs

| Column 1 Vλ-Cκ chimera stability optimization design | Column 2 [#]Kappa-kappa design | Column 3 (Antibody #) System, H1L1/H2L2 | Column 4 H1L1 Tag | Column 5 H2L2 Tag | Column 6 H1H2_L1L2 and H1H2_L2L1** | Column 7 Change in H1H2_L1L2 and H1H2_L2L1** from kappa-chimera | Column 8 H1H2_L1L2 and H1H2_L2L1 | Column 9 Change in H1H2_L1L2 and H1H2_L2L1 from kappa-chimera | Column 10 H1H2_L1L1 |
|---|---|---|---|---|---|---|---|---|---|
| / | / | (1) H3/Pertuzumab (bispecific chimeric Ab control) | / | FLAG | 53.6 | 0 | 44.2 | 0 | 23.8 |
| / | / | (2) CAT-2200/D3H44 (bispecific chimeric Ab control) | / | / | 7.6 | 0 | 6.0 | 0 | 67.2 |
| / | / | (3) CAT-2200/D3H44 (bispecific chimeric Ab control) | FLAG | / | 22.4 | 0 | 18.3 | 0 | 57.4 |
| 39 | / | (4) H3/Pertuzumab (stability optimization design control) | / | FLAG | 29.1 | −24.5 | 20.7 | −23.5 | 45 |
| 29 | / | (5) H3/Pertuzumab (stability optimization design control) | / | FLAG | 40.4 | −13.3 | 31.6 | −12.6 | 40.5 |
| 39 | / | (6) CAT-2200/D3H44 (stability optimization design control) | / | / | 1.9 | −5.8 | 1.4 | −4.6 | 70.3 |
| 29 | / | (7) CAT-2200/D3H44 (stability optimization designc ontrol) | / | / | 4.9 | −2.6 | 4.0 | −2.0 | 69.8 |
| 39 | 9060-9756 | (8) H3/Pertuzumab (designed bispecific chimeric Ab) | / | / | 86.4 | *32.8 | 77.9 | *33.8 | 6.8 |
| 39 | 9820-9823 | (9) H3/Pertuzumab (designed bispecific chimeric Ab) | / | / | 76.4 | *22.8 | 69.4 | *25.3 | 1.1 |

TABLE 9-continued

LC-MS pairing data for designed bispecific chimeric Abs

| Column 1 Vλ-Cκ chimera stability optimization design | Column 2 #Kappa-kappa design | Column 3 (Antibody #) System, H1L1/H2L2 | Column 4 H1L1 Tag | Column 5 H2L2 Tag | Column 6 H1H2_L1L2 and H1H2_L2L1** | Column 7 Change in H1H2_L1L2 and H1H2_L2L1** from kappa-chimera | Column 8 H1H2_L1L2 and H1H2_L2L1 | Column 9 Change in H1H2_L1L2 and H1H2_L2L1 from kappa-chimera | Column 10 H1H2_L1L1 |
|---|---|---|---|---|---|---|---|---|---|
| 29 | 9060-9756 | (10) H3/Pertuuzmab (designed bispecific chimeric Ab) | / | / | 88.4 | *34.8 | 80.2 | *36.0 | 1.7 |
| 29 | 9820-9823 | (11) H3/Pertuzumab (designed bispecific chimeric Ab) | / | / | 86.3 | *32.6 | 76.9 | *32.8 | 0.2 |
| 39 | 9060-9756 | (12) CAT-2200/D3H44 (designed bispecific chimeric Ab) | FLAG | / | 76.2 | 53.8 | 64.6 | 46.3 | 15.4 |
| 39 | 9820-9823 | (13) CAT-2200/D3H44 (designed bispecific chimeric Ab) | / | / | 96.0 | 88.4 | 86.4 | 80.4 | 0.5 |
| 29 | 9060-9756 | (14) CAT-2200/D3H44 (designed bispecific chimeric Ab) | FLAG | / | 77.4 | 55.0 | 65.7 | 47.4 | 15.5 |
| 29 | 9820-9823 | (15) CAT-2200/D3H44 (designed bispecific chimeric Ab) | / | / | 92.6 | 85.0 | 84.3 | 78.3 | 1.9 |

*Estimated change with respect to bispecific chimeric Ab control;
**Full Ab species considered only

What is claimed is:

1. A chimeric heterodimer comprising:
   a) a first immunoglobulin heavy chain polypeptide construct (H1) comprising a human heavy chain constant domain 1 (CH1) sequence and a human or mouse heavy chain variable domain (VH) sequence, and
   b) a first chimeric immunoglobulin light chain polypeptide construct (L1) comprising a human kappa light chain constant domain (Ckappa) IGKC*01 sequence having the amino acid sequence set forth in SEQ ID NO: 31 and a human or mouse lambda light chain variable domain (Vlambda) sequence,
   the Vlambda sequence comprising one or more stabilizing amino acid modifications that increase the melting temperature of the chimeric heterodimer compared to a corresponding wild-type chimeric heterodimer without the stabilizing amino acid modifications, as measured by differential scanning calorimetry (DSC) or differential scanning fluorimetry (DSF),
   wherein H1 and L1 form a first Fab region that binds to a first epitope,
   wherein the melting temperature of the first Fab region without the stabilizing amino acid modifications is decreased compared to the Fab region of a corresponding parental wild-type antibody,
   wherein the one or more stabilizing amino acid modifications comprise a substitution at residue 83, residue 85, or at both residues, wherein residue 83 is substituted with F, V, I, or A, and residue 85 is substituted with T or V; and
   wherein the numbering of amino acid residues is according to Kabat.

2. The chimeric heterodimer according to claim 1, wherein the Vlambda sequence further comprises stabilizing amino acid modifications at one or more amino acid residues at the interface between the Ckappa sequence and the Vlambda sequence, wherein the one or more amino acid residues are selected from the group consisting of residues 80, 105, and 106, wherein residue 80 is substituted with A or P, residue 105 is substituted with E, and residue 106 is substituted with I.

3. The chimeric heterodimer according to claim 1, wherein the Vlambda sequence of the chimeric heterodimer comprises
   a) 83F and 85T;
   b) 83V and 85T;
   c) 83I and 85T;
   d) 83A and 85T;
   e) 85T;
   f) 85V;
   g) 83F;
   h) 83V;
   i) 83I; or
   j) 83A.

4. The chimeric heterodimer according to claim 2, wherein the Vlambda sequence of the chimeric heterodimer comprises:
   a) 83F and 105E;
   b) 83F and 106I;
   c) 83F, 85T and 105E;
   d) 83F, 85V and 105E;
   e) 83F, 85T, 105E and 106I;
   f) 83F, 85V, 105E and 106I;
   g) 83V and 105E;
   h) 83V and 106I;
   i) 83V, 85T and 105E;
   j) 83V, 85V and 105E;
   k) 83V, 85T, 105E and 106I;
   l) 83I and 105E;
   m) 83I, 85T and 105E;
   n) 83I, 85T, 105E and 106I;
   o) 83A and 105E;
   p) 83A, 85T and 105E, or
   q) 83A, 85T, 105E and 106I.

5. An antibody construct comprising:
   a) a first heterodimer, wherein the first heterodimer is the chimeric heterodimer according to claim 1, and
   b) a scaffold
   wherein at least one of H1 and L1 of said first heterodimer is linked with or without a linker to the scaffold.

6. The antibody construct according to claim 5, further comprising a second heterodimer, said second heterodimer comprising:
   i) a second immunoglobulin heavy chain polypeptide construct (H2) comprising a heavy chain constant domain 1 (CH1) sequence, and a heavy chain variable domain (VH) sequence, and
   ii) a second immunoglobulin light chain polypeptide construct (L2) comprising a light chain constant domain (CL) sequence and a light chain variable domain (VL) sequence,
   wherein H2 and L2 form a second Fab region that binds to a second epitope, and at least one of H2 and L2 is linked with or without linkers to the scaffold.

7. The antibody construct according to claim 6, wherein the first epitope and the second epitope are the same.

8. The antibody construct according to claim 6, wherein the first epitope and the second epitope are different from each other.

9. The antibody construct according to claim 6, wherein the first heterodimer, the second heterodimer, or both heterodimers, further comprise one or more amino acid substitutions that promote light chain pairing.

10. The antibody construct according to claim 5, wherein the scaffold is an Fc region comprising a first heavy chain constant domain 3 (CH3) sequence and a second CH3 sequence.

11. The antibody construct according to claim 10, wherein the first CH3 sequence and the second CH3 sequence each comprise one or more amino acid modifications that promote formation of a heterodimeric CH3 domain compared to a homodimeric CH3 domain.

12. The antibody construct according to claim 10, wherein the Fc region further comprises a first constant domain 2 (CH2) sequence and a second CH2 sequence.

13. The antibody construct according to claim 10, wherein the Fc region is a human Fc, a human IgG1 Fc, a human IgA Fc, a human IgG Fc, a human IgD Fc, a human IgE Fc, a human IgM Fc, a human IgG2 Fc, a human IgG3 Fc, or a human IgG4 Fc.

14. The antibody construct of claim 5, wherein the linkers are one or more polypeptide linkers.

15. The antibody construct of claim 14, wherein the linkers comprise one or more antibody hinge regions.

16. The antibody construct of claim 15, wherein the linkers comprise one or more IgG1 hinge regions.

17. The antibody construct according to claim 5, wherein the antibody construct is conjugated to a drug.

18. The antibody construct according to claim 6, wherein the first heterodimer comprises:
  a) 83F, 85T and 105E;
  b) 83V and 85T;
  c) 83V, 85T, 105E and 106I;
  d) 83I and 85T;
  e) 83I, 85T, 105E and 106I;
  f) 83A and 85T; or
  g) 83A, 85T, 105E and 106I.

19. A pharmaceutical composition comprising the chimeric heterodimer of claim 1, and a pharmaceutically acceptable carrier.

20. A polynucleotide or set of polynucleotides encoding the chimeric heterodimer of claim 1.

21. A vector or set of vectors comprising one or more of the polynucleotides or sets of polynucleotides according to claim 20.

22. An isolated cell comprising the polynucleotide or set of polynucleotides according to claim 20.

23. A method of preparing a chimeric heterodimer of claim 1, comprising the steps of: (a) obtaining a host cell comprising a polynucleotide or set of polynucleotides encoding the chimeric heterodimer; (b) culturing the host cell in a host cell culture under conditions that allow expression of the chimeric heterodimer, and (c) collecting the chimeric heterodimer from the host cell culture.

24. A chimeric heterodimer comprising:
  a) a first immunoglobulin heavy chain polypeptide construct (H1) comprising a human heavy chain constant domain 1 (CH1) sequence and a human or mouse heavy chain variable domain (VH) sequence, and
  b) a first chimeric immunoglobulin light chain polypeptide construct (L1) comprising a human kappa light chain constant domain (Ckappa) IGKC*01 sequence having the amino acid sequence set forth in SEQ ID NO: 31 and a human or mouse lambda light chain variable domain (Vlambda) sequence,
  the Vlambda sequence comprising one or more stabilizing amino acid modifications that increase the melting temperature of the chimeric heterodimer compared to a corresponding wild-type chimeric heterodimer without the stabilizing amino acid modifications, as measured by differential scanning calorimetry (DSC) or differential scanning fluorimetry (DSF),
  wherein H1 and L1 form a first Fab region that binds to a first epitope,
  wherein the melting temperature of the first Fab region without the stabilizing amino acid modifications is decreased compared to the Fab region of a corresponding parental wild-type antibody, and wherein the stabilizing amino acid modifications comprise:
  a) 83F, 105E and 106AK;
  b) 83F, 105E, 106I and 106AK;
  c) 80A, 83F, 105E and 106AK;
  d) 80A, 83F, 105E, 106I and 106AK;
  e) 80A, 83F, 85T, 105E and 106AK;
  f) 80A, 83F, 85T, 105E, 106I and 106AK;
  g) 80P, 83F, 85T, 105E, 106I and 106AK; or
  h) 83F, 85T, 105E, 106I and 106AK.

25. A method of preparing an antibody construct of claim 5, comprising the steps of: (a) obtaining a host cell comprising a polynucleotide or set of polynucleotides encoding the antibody construct; (b) culturing the host cell in a host cell culture under conditions that allow expression of the antibody construct, and (c) collecting the antibody construct from the host cell culture.

* * * * *